(12) United States Patent
Borchert et al.

(10) Patent No.: US 8,703,465 B2
(45) Date of Patent: Apr. 22, 2014

(54) PULLULANASE VARIANTS AND USES THEREOF

(75) Inventors: Martin Borchert, Alleroed (DK); Morten Gjermansen, Greve (DK); Suzanne Clark, Youngsville, NC (US); Bernard Henrissat, Marseille cedex (FR); Maria B. Silow, Lund (SE); Peter F. Hallin, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/515,635

(22) PCT Filed: Dec. 22, 2010

(86) PCT No.: PCT/US2010/061761
§ 371 (c)(1),
(2), (4) Date: Aug. 29, 2012

(87) PCT Pub. No.: WO2011/087836
PCT Pub. Date: Jul. 21, 2011

(65) Prior Publication Data
US 2013/0017571 A1    Jan. 17, 2013

Related U.S. Application Data

(60) Provisional application No. 61/289,040, filed on Dec. 22, 2009.

(51) Int. Cl.
*C12N 9/26* (2006.01)
*C07K 1/00* (2006.01)

(52) U.S. Cl.
USPC .......................................... 435/201; 530/350

(58) Field of Classification Search
USPC .......................... 435/69.1, 183, 201; 530/350
See application file for complete search history.

(56) References Cited

U.S. PATENT DOCUMENTS

2011/0097779 A1*    4/2011   Soong et al. .................. 435/161

FOREIGN PATENT DOCUMENTS

WO            95/23852 A1      9/1995
WO            98/26058 A1      6/1998

OTHER PUBLICATIONS

Erra-Pujada et al., Journal of Bacteriology, vol. 181, No. 10, pp. 3284-3287 (1999).
Erra-Pujada et al., Uniprot Accession No. Q9Y818 (1999).
Imamura et al., Uniprot Accession No. Q8NKS8 (2002).
Janecek, Biologia, Bratislava, vol. 60, Supp. 16, pp. 177-184 (2005).
Jiao et al., Current Microbiology, vol. 62, No. 1, pp. 222-228 (2010).
Lin et al., Extremophiles, vol. 12, No. 5, pp. 641-650 (2008).
Tan et al., Journal of Molecular Biology, vol. 378, No. 4, pp. 852-870 (2008).
Chang-Pi-Hin et al, 2002, Biologia, 57(11), 155-162.
Pujada et al, 2001, Biotechnol Lett 23, 1273-1277.

* cited by examiner

*Primary Examiner* — Maryam Monshipouri
(74) *Attorney, Agent, or Firm* — Michael W. Krenicky

(57) ABSTRACT

A truncated pullulanase variant of a parent pullulanase belonging to family GH57 comprising an X47 domain and the use thereof.

7 Claims, 7 Drawing Sheets

SEQUENCE LISTING

<160> NUMBER OF SEQ ID NOS: 38

<210> SEQ ID NO 1
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: sig_peptide
<222> LOCATION: (1)..(81)
<220> FEATURE:
<221> NAME/KEY: mat_peptide
<222> LOCATION: (82)..(4011)

<400> SEQUENCE: 1

```
atg agg cgg gtg gtt gcc ctc ttc att gca att ttg atg ctt gga agc      48
Met Arg Arg Val Val Ala Leu Phe Ile Ala Ile Leu Met Leu Gly Ser
        -25                 -20                 -15 atc gtt gga gcg aac gtt aag agc gtt ggc gcg gcg gag ccg aag ccg      96
Ile Val Gly Ala Asn Val Lys Ser Val Gly Ala Ala Glu Pro Lys Pro
    -10                  -5                  -1   1               5 ctc aac gtc ata ata gtc tgg cac cag cac cag ccc tac tac tac gac     144
Leu Asn Val Ile Ile Val Trp His Gln His Gln Pro Tyr Tyr Tyr Asp
             10                  15                  20 cct gtc cag gac gtc tac acc agg ccc tgg gtc agg ctc cac gcg gcg     192
Pro Val Gln Asp Val Tyr Thr Arg Pro Trp Val Arg Leu His Ala Ala
         25                  30                  35 aac aac tac tgg aag atg gcc cac tac ctg agc cag tac ccg gag gtt     240
Asn Asn Tyr Trp Lys Met Ala His Tyr Leu Ser Gln Tyr Pro Glu Val
     40                  45                  50 cac gcc acc att gac ctc tcg ggt tcg ctg ata gcc cag ctt gcc gac     288
His Ala Thr Ile Asp Leu Ser Gly Ser Leu Ile Ala Gln Leu Ala Asp
 55                  60                  65 tac atg aac ggc aag aag gac acc tac cag ata atc acc gag aag ata     336
Tyr Met Asn Gly Lys Lys Asp Thr Tyr Gln Ile Ile Thr Glu Lys Ile
 70                  75                  80                  85 gcc aac ggg gaa ccc ctc acc gtc gac gag aag tgg ttc atg ctc cag     384
Ala Asn Gly Glu Pro Leu Thr Val Asp Glu Lys Trp Phe Met Leu Gln
                 90                  95                 100 gca ccg gga ggg ttc ttc gac aac acc atc ccc tgg aac ggt gaa ccg     432
Ala Pro Gly Gly Phe Phe Asp Asn Thr Ile Pro Trp Asn Gly Glu Pro
             105                 110                 115 ata acc gac ccc aac ggc aac ccg ata agg gac ttc tgg gac cgc tac     480
Ile Thr Asp Pro Asn Gly Asn Pro Ile Arg Asp Phe Trp Asp Arg Tyr
         120                 125                 130 acg gag ctg aag aac aag atg ctc agc gca aag gcc aag tac gca aac     528
Thr Glu Leu Lys Asn Lys Met Leu Ser Ala Lys Ala Lys Tyr Ala Asn
     135                 140                 145 ttc gtg act gag agc cag aag gtc gct gtg acg aac gag ttc aca gag     576
Phe Val Thr Glu Ser Gln Lys Val Ala Val Thr Asn Glu Phe Thr Glu
150                 155                 160                 165 cag gac tac ata gac cta gcg gtt ctc ttc aat ctc gct tgg att gac     624
Gln Asp Tyr Ile Asp Leu Ala Val Leu Phe Asn Leu Ala Trp Ile Asp
                 170                 175                 180 tac aat tac atc acg agc acg ccg gag ttc aag gcc ctc tac gac aag     672
Tyr Asn Tyr Ile Thr Ser Thr Pro Glu Phe Lys Ala Leu Tyr Asp Lys
             185                 190                 195 gtt gac gag ggc ggc tat aca agg gcg gac gtc aaa acc gtt ctc gac     720
Val Asp Glu Gly Gly Tyr Thr Arg Ala Asp Val Lys Thr Val Leu Asp
```

-continued

```
                200                 205                 210
gcc cag atc tgg ctt ctc aac cac acc ttc gag gag cac gag aag ata    768
Ala Gln Ile Trp Leu Leu Asn His Thr Phe Glu Glu His Glu Lys Ile
215                 220                 225 aac ctc ctc ctc gga aac ggc aac gtc gag gtc acg gtc gtt ccc tac    816
Asn Leu Leu Leu Gly Asn Gly Asn Val Glu Val Thr Val Val Pro Tyr
230                 235                 240                 245 gcc cac ccg ata ggc ccg ata ctc aac gac ttc ggc tgg gac agc gac    864
Ala His Pro Ile Gly Pro Ile Leu Asn Asp Phe Gly Trp Asp Ser Asp
                250                 255                 260 ttc aac gac cag gtc aag aag gcc gac gaa ctg tac aag ccg tac ctc    912
Phe Asn Asp Gln Val Lys Lys Ala Asp Glu Leu Tyr Lys Pro Tyr Leu
            265                 270                 275 ggc ggc ggc acc gcg gtt cca aaa ggc gga tgg gcg gct gag agc gcc    960
Gly Gly Gly Thr Ala Val Pro Lys Gly Gly Trp Ala Ala Glu Ser Ala
        280                 285                 290 ctc aac gac aaa act ctg gag atc ctc gcc gag aac ggc tgg gag tgg   1008
Leu Asn Asp Lys Thr Leu Glu Ile Leu Ala Glu Asn Gly Trp Glu Trp
    295                 300                 305 gtc atg acc gac cag atg gtt ctc gga aag ctc ggc att gag gga acc   1056
Val Met Thr Asp Gln Met Val Leu Gly Lys Leu Gly Ile Glu Gly Thr
310                 315                 320                 325 gtc gag aac tac cac aag ccc tgg gtg gcc gag ttc aac gga aag aag   1104
Val Glu Asn Tyr His Lys Pro Trp Val Ala Glu Phe Asn Gly Lys Lys
                330                 335                 340 ata tac ctc ttc cca aga aat cac gat cta agt gac aga gtt ggc ttt   1152
Ile Tyr Leu Phe Pro Arg Asn His Asp Leu Ser Asp Arg Val Gly Phe
            345                 350                 355 acc tac agc gga atg aac cag cag cag gcc gtt gag gac ttc gtc aac   1200
Thr Tyr Ser Gly Met Asn Gln Gln Gln Ala Val Glu Asp Phe Val Asn
        360                 365                 370 gag ctc ctc aag ctc cag aag cag aac tac gat ggc tcg ctg gtt tac   1248
Glu Leu Leu Lys Leu Gln Lys Gln Asn Tyr Asp Gly Ser Leu Val Tyr
    375                 380                 385 gtg gtc acg ctc gac ggc gag aac ccc gtg gag aac tac ccc tac gac   1296
Val Val Thr Leu Asp Gly Glu Asn Pro Val Glu Asn Tyr Pro Tyr Asp
390                 395                 400                 405 ggg gag ctc ttc ctc acc gaa ctc tac aag aag ctg acc gaa ctc cag   1344
Gly Glu Leu Phe Leu Thr Glu Leu Tyr Lys Lys Leu Thr Glu Leu Gln
                410                 415                 420 gag cag ggt ctc ata aga acc ctc acc ccg agc gag tac atc cag ctc   1392
Glu Gln Gly Leu Ile Arg Thr Leu Thr Pro Ser Glu Tyr Ile Gln Leu
            425                 430                 435 tac ggc gac aag gcc aac aag ctc aca cct cgg atg atg gag cgc ctt   1440
Tyr Gly Asp Lys Ala Asn Lys Leu Thr Pro Arg Met Met Glu Arg Leu
        440                 445                 450 gac ctc acc gga gac aac gtt aac gcc ctc ctc aag gcc cag agc ctc   1488
Asp Leu Thr Gly Asp Asn Val Asn Ala Leu Leu Lys Ala Gln Ser Leu
    455                 460                 465 ggc gaa ctc tac gac atg acc ggc gtt aag gag gag atg cag tgg ccc   1536
Gly Glu Leu Tyr Asp Met Thr Gly Val Lys Glu Glu Met Gln Trp Pro
470                 475                 480                 485 gag agc agc tgg ata gac gga acc ctc tcc acg tgg ata ggc gag ccc   1584
Glu Ser Ser Trp Ile Asp Gly Thr Leu Ser Thr Trp Ile Gly Glu Pro
                490                 495                 500 cag gag aac tac ggc tgg tac tgg ctc tac atg gcc agg aag gcc ctt   1632
Gln Glu Asn Tyr Gly Trp Tyr Trp Leu Tyr Met Ala Arg Lys Ala Leu
            505                 510                 515 atg gag aac aag gat aaa atg agc cag gcg gac tgg gag aag gcc tac   1680
Met Glu Asn Lys Asp Lys Met Ser Gln Ala Asp Trp Glu Lys Ala Tyr
```

-continued

```
                 520                  525                  530
gag tac ctg ctc cgc gcc gag gca agc gac tgg ttc tgg tgg tac gga    1728
Glu Tyr Leu Leu Arg Ala Glu Ala Ser Asp Trp Phe Trp Trp Tyr Gly
    535                  540                  545 agc gac cag gac agc ggc cag gac tac acc ttc gac cgc tac ctg aag    1776
Ser Asp Gln Asp Ser Gly Gln Asp Tyr Thr Phe Asp Arg Tyr Leu Lys
550                  555                  560                  565 acc tac ctc tac gag atg tac aag ctg gca gga gtc gag ccg ccg agc    1824
Thr Tyr Leu Tyr Glu Met Tyr Lys Leu Ala Gly Val Glu Pro Pro Ser
                570                  575                  580 tac ctc ttc ggc aac tac ttc ccg gac gga gag ccc tac acc acg agg    1872
Tyr Leu Phe Gly Asn Tyr Phe Pro Asp Gly Glu Pro Tyr Thr Thr Arg
            585                  590                  595 ggc ctg gtc gga ctc aag gac ggc gag atg aag aac ttc tcc agc atg    1920
Gly Leu Val Gly Leu Lys Asp Gly Glu Met Lys Asn Phe Ser Ser Met
        600                  605                  610 tcc ccg ctg gca aag ggc gtg agc gtc tat ttc gac ggc gag ggg ata    1968
Ser Pro Leu Ala Lys Gly Val Ser Val Tyr Phe Asp Gly Glu Gly Ile
    615                  620                  625 cac ttc ata gtg aaa ggg aac ctg gac agg ttc gag gtg agc atc tgg    2016
His Phe Ile Val Lys Gly Asn Leu Asp Arg Phe Glu Val Ser Ile Trp
630                  635                  640                  645 gag aag gat gag cgc gtt ggc aac acg ttc acc cgc ctc caa gag aag    2064
Glu Lys Asp Glu Arg Val Gly Asn Thr Phe Thr Arg Leu Gln Glu Lys
                650                  655                  660 ccg gac gag ttg agc tat ttc atg ttc cca ttc tca agg gac agc gtt    2112
Pro Asp Glu Leu Ser Tyr Phe Met Phe Pro Phe Ser Arg Asp Ser Val
            665                  670                  675 ggt ctc ctc ata acc aag cac gtc gtg tac gag aac gga aag gcc gag    2160
Gly Leu Leu Ile Thr Lys His Val Val Tyr Glu Asn Gly Lys Ala Glu
        680                  685                  690 ata tac ggc gcc acc gac tac gag aag agc gag aag ctt ggg gaa gcc    2208
Ile Tyr Gly Ala Thr Asp Tyr Glu Lys Ser Glu Lys Leu Gly Glu Ala
    695                  700                  705 acc gtc aag aac acg agc gaa gga atc gaa gtc gtc ctt ccc ttt gac    2256
Thr Val Lys Asn Thr Ser Glu Gly Ile Glu Val Val Leu Pro Phe Asp
710                  715                  720                  725 tac ata gaa aac ccc tcc gac ttc tac ttc gct gtc tcg acg gtc aaa    2304
Tyr Ile Glu Asn Pro Ser Asp Phe Tyr Phe Ala Val Ser Thr Val Lys
                730                  735                  740 gat gga gac ctt gag gtg ata agc act cct gtg gag ctc aag ctc ccg    2352
Asp Gly Asp Leu Glu Val Ile Ser Thr Pro Val Glu Leu Lys Leu Pro
            745                  750                  755 acc gag gtc aag gga gtc gtc ata gcc gat ata acc gac cca gaa ggc    2400
Thr Glu Val Lys Gly Val Val Ile Ala Asp Ile Thr Asp Pro Glu Gly
        760                  765                  770 gac gac cat ggg ccc gga aac tac act tat ccc acg gac aag gtc ttc    2448
Asp Asp His Gly Pro Gly Asn Tyr Thr Tyr Pro Thr Asp Lys Val Phe
    775                  780                  785 aag cca ggt gtt ttc gac ctc ctc cgc ttc agg atg ctc gaa cag acg    2496
Lys Pro Gly Val Phe Asp Leu Leu Arg Phe Arg Met Leu Glu Gln Thr
790                  795                  800                  805 gag agc tac gtc atg gag ttc tac ttc aag gac cta ggt ggt aac ccg    2544
Glu Ser Tyr Val Met Glu Phe Tyr Phe Lys Asp Leu Gly Gly Asn Pro
                810                  815                  820 tgg aac gga ccc aac ggc ttc agc ctc cag ata atc gag gtc tac ctc    2592
Trp Asn Gly Pro Asn Gly Phe Ser Leu Gln Ile Ile Glu Val Tyr Leu
            825                  830                  835 gac ttc aag gac ggt gga aac agt tcg gcc att aag atg ttc ccc gac    2640
Asp Phe Lys Asp Gly Gly Asn Ser Ser Ala Ile Lys Met Phe Pro Asp
```

-continued

```
              840                 845                 850
gga ccg gga gcc aac gtc aac ctc gac ccc gag cat cca tgg gac gtt    2688
Gly Pro Gly Ala Asn Val Asn Leu Asp Pro Glu His Pro Trp Asp Val
        855                 860                 865 gcc ttc agg ata gcg ggc tgg gac tac gga aac ctc atc atc ctg ccg    2736
Ala Phe Arg Ile Ala Gly Trp Asp Tyr Gly Asn Leu Ile Ile Leu Pro
870                 875                 880                 885 aac gga acg gcc atc cag ggc gag atg cag att tcc gca gat ccg gtt    2784
Asn Gly Thr Ala Ile Gln Gly Glu Met Gln Ile Ser Ala Asp Pro Val
                890                 895                 900 aag aac gcc ata ata gtc aag gtt cca aag aag tac atc gcc ata aac    2832
Lys Asn Ala Ile Ile Val Lys Val Pro Lys Lys Tyr Ile Ala Ile Asn
            905                 910                 915 gag gac tac ggc ctc tgg gga gac gtc ctc gtc ggc tcg cag gac ggc    2880
Glu Asp Tyr Gly Leu Trp Gly Asp Val Leu Val Gly Ser Gln Asp Gly
        920                 925                 930 tac ggc ccg gac aag tgg aga acg gcg gca gtg gat gcg gag cag tgg    2928
Tyr Gly Pro Asp Lys Trp Arg Thr Ala Ala Val Asp Ala Glu Gln Trp
935                 940                 945 aag ctt gga ggt gcg gac ccg cag gca gtc ata aac ggc gtg gcc ccg    2976
Lys Leu Gly Gly Ala Asp Pro Gln Ala Val Ile Asn Gly Val Ala Pro
950                 955                 960                 965 cgc gtc att gat gag ctg gtt ccg cag ggc ttt gaa ccg acc cag gag    3024
Arg Val Ile Asp Glu Leu Val Pro Gln Gly Phe Glu Pro Thr Gln Glu
                970                 975                 980 gag cag ctg agc agc tac gat gca aac gac atg aag ctc gcc act gtc    3072
Glu Gln Leu Ser Ser Tyr Asp Ala Asn Asp Met Lys Leu Ala Thr Val
            985                 990                 995 aag gcg ctg cta ctc ctc aag cag ggc atc gtt gtg acc gac ccg        3117
Lys Ala Leu Leu Leu Leu Lys Gln Gly Ile Val Val Thr Asp Pro
        1000                1005                1010 gag gga gac gac cac ggg ccg gga acg tac acc tat ccg acg gac        3162
Glu Gly Asp Asp His Gly Pro Gly Thr Tyr Thr Tyr Pro Thr Asp
        1015                1020                1025 aaa gtt ttc aag ccc ggt gtt ttc gac ctc ctc aag ttc aag gtg        3207
Lys Val Phe Lys Pro Gly Val Phe Asp Leu Leu Lys Phe Lys Val
        1030                1035                1040 acc gag gga agc gac gac tgg acg ctg gag ttc cac ttc aaa gac        3252
Thr Glu Gly Ser Asp Asp Trp Thr Leu Glu Phe His Phe Lys Asp
        1045                1050                1055 ctc ggt gga aac ccg tgg aac ggg ccg aac ggc ttc agc ctg cag        3297
Leu Gly Gly Asn Pro Trp Asn Gly Pro Asn Gly Phe Ser Leu Gln
        1060                1065                1070 ata atc gag gta tac ttc gac ttc aag gag ggc ggg aac gtc tcg        3342
Ile Ile Glu Val Tyr Phe Asp Phe Lys Glu Gly Gly Asn Val Ser
        1075                1080                1085 gcc att aag atg ttc ccg gat ggg ccc gga agc aac gtc cgt ctt        3387
Ala Ile Lys Met Phe Pro Asp Gly Pro Gly Ser Asn Val Arg Leu
        1090                1095                1100 gat cca aat cac cca tgg gac ctg gcg ctt agg ata gcc ggc tgg        3432
Asp Pro Asn His Pro Trp Asp Leu Ala Leu Arg Ile Ala Gly Trp
        1105                1110                1115 gac tac gga aac ctg ata att ctg ccc gac gga acc gcc tac caa        3477
Asp Tyr Gly Asn Leu Ile Ile Leu Pro Asp Gly Thr Ala Tyr Gln
        1120                1125                1130 ggc gag atg cag att tcc gca gat ccg gtt aag aac gcc ata ata        3522
Gly Glu Met Gln Ile Ser Ala Asp Pro Val Lys Asn Ala Ile Ile
        1135                1140                1145 gtc aag gtt cca aag aag tac ctg aac ata tcc gac tac gga ctc        3567
Val Lys Val Pro Lys Lys Tyr Leu Asn Ile Ser Asp Tyr Gly Leu
```

```
                 1150                 1155                 1160
tac acc gcc gtc atc gtg ggt tcc caa gac ggg tac ggc ccg gac      3612
Tyr Thr Ala Val Ile Val Gly Ser Gln Asp Gly Tyr Gly Pro Asp
            1165                 1170                 1175 aag tgg agg ccc gtg gcc gct gag gcc gag cag tgg aag ctc gga      3657
Lys Trp Arg Pro Val Ala Ala Glu Ala Glu Gln Trp Lys Leu Gly
            1180                 1185                 1190 ggc gca gac ccc cag gcg gtc ata gac aac ctc gta cca agg gtc      3702
Gly Ala Asp Pro Gln Ala Val Ile Asp Asn Leu Val Pro Arg Val
            1195                 1200                 1205 gtt gat gaa ctc gtg ccg gag ggc ttc aag cca acg cag gag gag      3747
Val Asp Glu Leu Val Pro Glu Gly Phe Lys Pro Thr Gln Glu Glu
            1210                 1215                 1220 cag ctg agc agc tac gac ctt gag aag aag acc ctg gcg acg gtg      3792
Gln Leu Ser Ser Tyr Asp Leu Glu Lys Lys Thr Leu Ala Thr Val
            1225                 1230                 1235 ctc atg gta ccg ctc gtc aat ggg act ggc ggc gag gaa cca acg      3837
Leu Met Val Pro Leu Val Asn Gly Thr Gly Gly Glu Glu Pro Thr
            1240                 1245                 1250 ccg acg gag agc cca acg gaa acg acg aca acc aca ccc agc gaa      3882
Pro Thr Glu Ser Pro Thr Glu Thr Thr Thr Thr Thr Pro Ser Glu
            1255                 1260                 1265 aca acc acc aca act tca acg acc acc ggc cca agc tca acg acc      3927
Thr Thr Thr Thr Thr Ser Thr Thr Thr Gly Pro Ser Ser Thr Thr
            1270                 1275                 1280 acc agc aca ccc ggc gga gga atc tgc ggc cca ggc att ata gcg      3972
Thr Ser Thr Pro Gly Gly Gly Ile Cys Gly Pro Gly Ile Ile Ala
            1285                 1290                 1295 ggc ctg gcc ctg ata ccg ctc ctc ctc aag agg agg aac tga           4014
Gly Leu Ala Leu Ile Pro Leu Leu Leu Lys Arg Arg Asn
            1300                 1305                 1310

<210> SEQ ID NO 2
<211> LENGTH: 1337
<212> TYPE: PRT
<213> ORGANISM: Thermococcus hydrothermalis

<400> SEQUENCE: 2

Met Arg Arg Val Val Ala Leu Phe Ile Ala Ile Leu Met Leu Gly Ser
            -25                 -20                 -15

Ile Val Gly Ala Asn Val Lys Ser Val Gly Ala Ala Glu Pro Lys Pro
        -10                  -5              -1   1               5

Leu Asn Val Ile Ile Val Trp His Gln His Gln Pro Tyr Tyr Tyr Asp
                    10                  15                  20

Pro Val Gln Asp Val Tyr Thr Arg Pro Trp Val Arg Leu His Ala Ala
                25                  30                  35

Asn Asn Tyr Trp Lys Met Ala His Tyr Leu Ser Gln Tyr Pro Glu Val
            40                  45                  50

His Ala Thr Ile Asp Leu Ser Gly Ser Leu Ile Ala Gln Leu Ala Asp
        55                  60                  65

Tyr Met Asn Gly Lys Lys Asp Thr Tyr Gln Ile Ile Thr Glu Lys Ile
70                  75                  80                  85

Ala Asn Gly Glu Pro Leu Thr Val Asp Glu Lys Trp Phe Met Leu Gln
                90                  95                  100

Ala Pro Gly Gly Phe Phe Asp Asn Thr Ile Pro Trp Asn Gly Glu Pro
            105                 110                 115

Ile Thr Asp Pro Asn Gly Asn Pro Ile Arg Asp Phe Trp Asp Arg Tyr
        120                 125                 130
```

-continued

```
Thr Glu Leu Lys Asn Lys Met Leu Ser Ala Lys Ala Lys Tyr Ala Asn
            135                 140                 145

Phe Val Thr Glu Ser Gln Lys Val Ala Val Thr Asn Glu Phe Thr Glu
150                 155                 160                 165

Gln Asp Tyr Ile Asp Leu Ala Val Leu Phe Asn Leu Ala Trp Ile Asp
                170                 175                 180

Tyr Asn Tyr Ile Thr Ser Thr Pro Glu Phe Lys Ala Leu Tyr Asp Lys
                185                 190                 195

Val Asp Glu Gly Gly Tyr Thr Arg Ala Asp Val Lys Thr Val Leu Asp
            200                 205                 210

Ala Gln Ile Trp Leu Leu Asn His Thr Phe Glu Glu His Glu Lys Ile
            215                 220                 225

Asn Leu Leu Leu Gly Asn Gly Asn Val Glu Val Thr Val Val Pro Tyr
230                 235                 240                 245

Ala His Pro Ile Gly Pro Ile Leu Asn Asp Phe Gly Trp Asp Ser Asp
                250                 255                 260

Phe Asn Asp Gln Val Lys Lys Ala Asp Glu Leu Tyr Lys Pro Tyr Leu
                265                 270                 275

Gly Gly Gly Thr Ala Val Pro Lys Gly Gly Trp Ala Ala Glu Ser Ala
            280                 285                 290

Leu Asn Asp Lys Thr Leu Glu Ile Leu Ala Glu Asn Gly Trp Glu Trp
295                 300                 305

Val Met Thr Asp Gln Met Val Leu Gly Lys Leu Gly Ile Glu Gly Thr
310                 315                 320                 325

Val Glu Asn Tyr His Lys Pro Trp Val Ala Glu Phe Asn Gly Lys Lys
                330                 335                 340

Ile Tyr Leu Phe Pro Arg Asn His Asp Leu Ser Asp Arg Val Gly Phe
                345                 350                 355

Thr Tyr Ser Gly Met Asn Gln Gln Ala Val Glu Asp Phe Val Asn
            360                 365                 370

Glu Leu Leu Lys Leu Gln Lys Gln Asn Tyr Asp Gly Ser Leu Val Tyr
            375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
                410                 415                 420

Glu Gln Gly Leu Ile Arg Thr Leu Thr Pro Ser Glu Tyr Ile Gln Leu
            425                 430                 435

Tyr Gly Asp Lys Ala Asn Lys Leu Thr Pro Arg Met Met Glu Arg Leu
            440                 445                 450

Asp Leu Thr Gly Asp Asn Val Asn Ala Leu Leu Lys Ala Gln Ser Leu
455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
                505                 510                 515

Met Glu Asn Lys Asp Lys Met Ser Gln Ala Asp Trp Glu Lys Ala Tyr
            520                 525                 530

Glu Tyr Leu Leu Arg Ala Glu Ala Ser Asp Trp Phe Trp Trp Tyr Gly
            535                 540                 545

Ser Asp Gln Asp Ser Gly Gln Asp Tyr Thr Phe Asp Arg Tyr Leu Lys
550                 555                 560                 565
```

-continued

Thr Tyr Leu Tyr Glu Met Tyr Lys Leu Ala Gly Val Glu Pro Pro Ser
            570                 575                 580

Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
            600                 605                 610

Ser Pro Leu Ala Lys Gly Val Ser Val Tyr Phe Asp Gly Glu Gly Ile
            615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
            650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
            680                 685                 690

Ile Tyr Gly Ala Thr Asp Tyr Glu Lys Ser Glu Lys Leu Gly Glu Ala
695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
            730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
            760                 765                 770

Asp Asp His Gly Pro Gly Asn Tyr Thr Tyr Pro Thr Asp Lys Val Phe
775                 780                 785

Lys Pro Gly Val Phe Asp Leu Leu Arg Phe Arg Met Leu Glu Gln Thr
790                 795                 800                 805

Glu Ser Tyr Val Met Glu Phe Tyr Phe Lys Asp Leu Gly Gly Asn Pro
            810                 815                 820

Trp Asn Gly Pro Asn Gly Phe Ser Leu Gln Ile Ile Glu Val Tyr Leu
            825                 830                 835

Asp Phe Lys Asp Gly Gly Asn Ser Ser Ala Ile Lys Met Phe Pro Asp
            840                 845                 850

Gly Pro Gly Ala Asn Val Asn Leu Asp Pro Glu His Pro Trp Asp Val
            855                 860                 865

Ala Phe Arg Ile Ala Gly Trp Asp Tyr Gly Asn Leu Ile Ile Leu Pro
870                 875                 880                 885

Asn Gly Thr Ala Ile Gln Gly Glu Met Gln Ile Ser Ala Asp Pro Val
            890                 895                 900

Lys Asn Ala Ile Ile Val Lys Val Pro Lys Lys Tyr Ile Ala Ile Asn
            905                 910                 915

Glu Asp Tyr Gly Leu Trp Gly Asp Val Leu Val Gly Ser Gln Asp Gly
            920                 925                 930

Tyr Gly Pro Asp Lys Trp Arg Thr Ala Ala Val Asp Ala Glu Gln Trp
            935                 940                 945

Lys Leu Gly Gly Ala Asp Pro Gln Ala Val Ile Asn Gly Val Ala Pro
950                 955                 960                 965

Arg Val Ile Asp Glu Leu Val Pro Gln Gly Phe Glu Pro Thr Gln Glu
            970                 975                 980

Glu Gln Leu Ser Ser Tyr Asp Ala Asn Asp Met Lys Leu Ala Thr Val

```
                    985               990               995
Lys Ala Leu  Leu Leu Leu Lys  Gln Gly Ile Val  Val Thr Asp Pro
        1000              1005              1010

Glu Gly Asp  Asp His Gly Pro  Gly Thr Tyr Thr  Tyr Pro Thr Asp
        1015              1020              1025

Lys Val Phe  Lys Pro Gly Val  Phe Asp Leu Leu  Lys Phe Lys Val
        1030              1035              1040

Thr Glu Gly  Ser Asp Asp Trp  Thr Leu Glu Phe  His Phe Lys Asp
        1045              1050              1055

Leu Gly Gly  Asn Pro Trp Asn  Gly Pro Asn Gly  Phe Ser Leu Gln
        1060              1065              1070

Ile Ile Glu  Val Tyr Phe Asp  Phe Lys Glu Gly  Gly Asn Val Ser
        1075              1080              1085

Ala Ile Lys  Met Phe Pro Asp  Gly Pro Gly Ser  Asn Val Arg Leu
        1090              1095              1100

Asp Pro Asn  His Pro Trp Asp  Leu Ala Leu Arg  Ile Ala Gly Trp
        1105              1110              1115

Asp Tyr Gly  Asn Leu Ile Ile  Leu Pro Asp Gly  Thr Ala Tyr Gln
        1120              1125              1130

Gly Glu Met  Gln Ile Ser Ala  Asp Pro Val Lys  Asn Ala Ile Ile
        1135              1140              1145

Val Lys Val  Pro Lys Lys Tyr  Leu Asn Ile Ser  Asp Tyr Gly Leu
        1150              1155              1160

Tyr Thr Ala  Val Ile Val Gly  Ser Gln Asp Gly  Tyr Gly Pro Asp
        1165              1170              1175

Lys Trp Arg  Pro Val Ala Ala  Glu Ala Glu Gln  Trp Lys Leu Gly
        1180              1185              1190

Gly Ala Asp  Pro Gln Ala Val  Ile Asp Asn Leu  Val Pro Arg Val
        1195              1200              1205

Val Asp Glu  Leu Val Pro Glu  Gly Phe Lys Pro  Thr Gln Glu Glu
        1210              1215              1220

Gln Leu Ser  Ser Tyr Asp Leu  Glu Lys Lys Thr  Leu Ala Thr Val
        1225              1230              1235

Leu Met Val  Pro Leu Val Asn  Gly Thr Gly Glu  Glu Pro Thr
        1240              1245              1250

Pro Thr Glu  Ser Pro Thr Glu  Thr Thr Thr Thr  Pro Ser Glu
        1255              1260              1265

Thr Thr Thr  Thr Thr Ser Thr  Thr Thr Gly Pro  Ser Ser Thr Thr
        1270              1275              1280

Thr Ser Thr  Pro Gly Gly Gly  Ile Cys Gly Pro  Gly Ile Ile Ala
        1285              1290              1295

Gly Leu Ala  Leu Ile Pro Leu  Leu Leu Lys Arg  Arg Asn
        1300              1305              1310

<210> SEQ ID NO 3
<211> LENGTH: 3270
<212> TYPE: DNA
<213> ORGANISM: Thermococcus litoralis
<220> FEATURE:
<221> NAME/KEY: CDS
<222> LOCATION: (1)..(3267)
<223> OTHER INFORMATION: Mature sequence
<220> FEATURE:
<221> NAME/KEY: misc_signal
<222> LOCATION: (1)..(72)
<220> FEATURE:
<221> NAME/KEY: mat_peptide
<222> LOCATION: (73)..(3267)
```

<400> SEQUENCE: 3

```
atg aag aaa ggc ttg gca atg ttt ctc ata ttt tta gtt gcc ttg agc      48
Met Lys Lys Gly Leu Ala Met Phe Leu Ile Phe Leu Val Ala Leu Ser
            -20              -15                  -10 att gct gaa gta ggg gtg aag gca gag gag cca aag cca ttg aac gtt      96
Ile Ala Glu Val Gly Val Lys Ala Glu Glu Pro Lys Pro Leu Asn Val
        -5               -1  1                   5 att att gtg tgg cat cag cac caa ccg tac tac tac gac cca atc cag     144
Ile Ile Val Trp His Gln His Gln Pro Tyr Tyr Tyr Asp Pro Ile Gln
        10              15                  20 gac atc tat act aga cct tgg gtt agg ctg cat gca gcc aat aat tac     192
Asp Ile Tyr Thr Arg Pro Trp Val Arg Leu His Ala Ala Asn Asn Tyr
25              30                  35                  40 tgg aag atg gca aac tat ctc agc aaa tac cca gat gtt cat gtt gct     240
Trp Lys Met Ala Asn Tyr Leu Ser Lys Tyr Pro Asp Val His Val Ala
                45                  50                  55 ata gat ttg tcg ggt tct tta att gcc cag ctt gcc gat tac atg aac     288
Ile Asp Leu Ser Gly Ser Leu Ile Ala Gln Leu Ala Asp Tyr Met Asn
            60                  65                  70 ggc aaa aaa gat aca tac cag atc gtc acg gag aaa ata gca aat ggg     336
Gly Lys Lys Asp Thr Tyr Gln Ile Val Thr Glu Lys Ile Ala Asn Gly
        75                  80                  85 gaa cca cta aca ctt gaa gac aaa tgg ttc atg ctc caa gct ccg ggg     384
Glu Pro Leu Thr Leu Glu Asp Lys Trp Phe Met Leu Gln Ala Pro Gly
    90                  95                  100 ggc ttt ttt gat cat act ata cct tgg aat gga gag cct gtt gca gat     432
Gly Phe Phe Asp His Thr Ile Pro Trp Asn Gly Glu Pro Val Ala Asp
105                 110                 115                 120 gaa aac ggc aac cct tac agg gaa caa tgg gat aga tat gca gaa ctc     480
Glu Asn Gly Asn Pro Tyr Arg Glu Gln Trp Asp Arg Tyr Ala Glu Leu
                125                 130                 135 aag gac aaa aga aat aat gcg ttt aaa aag tat gca aac tta cct tta     528
Lys Asp Lys Arg Asn Asn Ala Phe Lys Lys Tyr Ala Asn Leu Pro Leu
            140                 145                 150 aat gag cag aag gtg aaa ata acg gct gaa ttc acg gag cag gat tac     576
Asn Glu Gln Lys Val Lys Ile Thr Ala Glu Phe Thr Glu Gln Asp Tyr
        155                 160                 165 att gac tta gct gtc ttg ttc aac ttg gct tgg att gac tat aac tac     624
Ile Asp Leu Ala Val Leu Phe Asn Leu Ala Trp Ile Asp Tyr Asn Tyr
    170                 175                 180 ata atc aac act cca gag ctt aag gca ctt tac gac aaa gtt gat gta     672
Ile Ile Asn Thr Pro Glu Leu Lys Ala Leu Tyr Asp Lys Val Asp Val
185                 190                 195                 200 ggt ggg tac acc aag gaa gat gtg gca act gtc cta aaa cac cag atg     720
Gly Gly Tyr Thr Lys Glu Asp Val Ala Thr Val Leu Lys His Gln Met
                205                 210                 215 tgg ctt ctc aat cac acg ttt gaa gaa cat gag aag ata aac tac ctc     768
Trp Leu Leu Asn His Thr Phe Glu Glu His Glu Lys Ile Asn Tyr Leu
            220                 225                 230 ctt gga aac gga aat gtt gaa gtt act gta gtg cca tat gct cat cca     816
Leu Gly Asn Gly Asn Val Glu Val Thr Val Val Pro Tyr Ala His Pro
        235                 240                 245 att ggt cca ctg ctc aac gac ttt ggc tgg tac gag gat ttt gat gct     864
Ile Gly Pro Leu Leu Asn Asp Phe Gly Trp Tyr Glu Asp Phe Asp Ala
    250                 255                 260 cat gta aag aaa gcc cac gag ctc tat aag aag tat cta gga gat aac     912
His Val Lys Lys Ala His Glu Leu Tyr Lys Lys Tyr Leu Gly Asp Asn
265                 270                 275                 280 aga gtt gaa ccc caa gga gga tgg gct gca gaa agc gca tta aat gac     960
Arg Val Glu Pro Gln Gly Gly Trp Ala Ala Glu Ser Ala Leu Asn Asp
```

-continued

```
                Arg Val Glu Pro Gln Gly Gly Trp Ala Ala Glu Ser Ala Leu Asn Asp
                                285                 290                 295 aag acc ctt gag ata tta act aac aat gga tgg aaa tgg gta atg act        1008
Lys Thr Leu Glu Ile Leu Thr Asn Asn Gly Trp Lys Trp Val Met Thr
            300                 305                 310 gat cag atg gtt ctt gac atc ctt gga att ccc aac aca gtt gaa aat        1056
Asp Gln Met Val Leu Asp Ile Leu Gly Ile Pro Asn Thr Val Glu Asn
            315                 320                 325 tat tac aaa cct tgg gta gct gaa ttt aac ggc aag aaa atc tat ctc        1104
Tyr Tyr Lys Pro Trp Val Ala Glu Phe Asn Gly Lys Lys Ile Tyr Leu
        330                 335                 340 ttc cca aga aac cat gac tta agt gac aga gtt ggg ttt agg tat tca        1152
Phe Pro Arg Asn His Asp Leu Ser Asp Arg Val Gly Phe Arg Tyr Ser
345                 350                 355                 360 ggc atg aac caa tac caa gct gtt gag gac ttt gtc aat gag ctt ctc        1200
Gly Met Asn Gln Tyr Gln Ala Val Glu Asp Phe Val Asn Glu Leu Leu
                365                 370                 375 aag gta caa aaa gag aac tac gat gga agc ctt gtt tat gtt gta acc        1248
Lys Val Gln Lys Glu Asn Tyr Asp Gly Ser Leu Val Tyr Val Val Thr
            380                 385                 390 cta gac gga gag aac cca tgg gaa cac tac ccg ttt gat ggc aag ata        1296
Leu Asp Gly Glu Asn Pro Trp Glu His Tyr Pro Phe Asp Gly Lys Ile
        395                 400                 405 ttc ctt gag gag ctg tac aag aag ctt act gaa ctt caa aag cag ggc        1344
Phe Leu Glu Glu Leu Tyr Lys Lys Leu Thr Glu Leu Gln Lys Gln Gly
    410                 415                 420 tta ata agg acg gta acc ccg agt gaa tac atc cag atg tat gga gac        1392
Leu Ile Arg Thr Val Thr Pro Ser Glu Tyr Ile Gln Met Tyr Gly Asp
425                 430                 435                 440 aag gca aac aaa ctc act cca aag ctc atg aag agg ctt gat ttc aca        1440
Lys Ala Asn Lys Leu Thr Pro Lys Leu Met Lys Arg Leu Asp Phe Thr
                445                 450                 455 aca gaa gag aga gtt aat gcc cta tta aaa gct caa agc ctc ggc gag        1488
Thr Glu Glu Arg Val Asn Ala Leu Leu Lys Ala Gln Ser Leu Gly Glu
            460                 465                 470 ctt tac gac atg gct ggt gtt gaa gag aat atg caa tgg cca gaa tcc        1536
Leu Tyr Asp Met Ala Gly Val Glu Glu Asn Met Gln Trp Pro Glu Ser
        475                 480                 485 agt tgg gtt gat gga aca ctt tcg aca tgg att ggt gag ccc caa gag        1584
Ser Trp Val Asp Gly Thr Leu Ser Thr Trp Ile Gly Glu Pro Gln Glu
    490                 495                 500 aac ttg gga tgg tac tgg ctc tac ttg gga aga aaa gca tta ttt gaa        1632
Asn Leu Gly Trp Tyr Trp Leu Tyr Leu Gly Arg Lys Ala Leu Phe Glu
505                 510                 515                 520 aat aag aac aag gtt gta gac tgg aac acc gca tat gaa tat ctc tta        1680
Asn Lys Asn Lys Val Val Asp Trp Asn Thr Ala Tyr Glu Tyr Leu Leu
                525                 530                 535 aga gca gaa gca agt gac tgg ttc tgg tgg tat gga agc gac caa gac        1728
Arg Ala Glu Ala Ser Asp Trp Phe Trp Trp Tyr Gly Ser Asp Gln Asp
            540                 545                 550 agc ggg cag gac tat aca ttt gat cgc tat ctt aag acg tac ctc tat        1776
Ser Gly Gln Asp Tyr Thr Phe Asp Arg Tyr Leu Lys Thr Tyr Leu Tyr
        555                 560                 565 gag atg tat aag ttc gct ggg ctg gaa att ccg agc tat ctc ttc gga        1824
Glu Met Tyr Lys Phe Ala Gly Leu Glu Ile Pro Ser Tyr Leu Phe Gly
    570                 575                 580 aac tat ttc ccc aac gga gag cca tat gca ata aga gag ctc aca gga        1872
Asn Tyr Phe Pro Asn Gly Glu Pro Tyr Ala Ile Arg Glu Leu Thr Gly
585                 590                 595                 600 tta cca gaa gga gag aaa aag agc tgg tca agc tta tca ccc att gct        1920
```

```
                                          -continued

Leu Pro Glu Gly Glu Lys Lys Ser Trp Ser Ser Leu Ser Pro Ile Ala
            605                 610                 615 gag gga gta gag ctc tac ttt gat gag cag gga tta cat ttt gtt gtt      1968
Glu Gly Val Glu Leu Tyr Phe Asp Glu Gln Gly Leu His Phe Val Val
            620                 625                 630 aaa act aca aaa gag ttc gaa ata agc atc ttt gag ccc gga aag gtc      2016
Lys Thr Thr Lys Glu Phe Glu Ile Ser Ile Phe Glu Pro Gly Lys Val
            635                 640                 645 atg ggt aac aca ttt act ctt ctc cag acc aaa cca agt gaa cta aga      2064
Met Gly Asn Thr Phe Thr Leu Leu Gln Thr Lys Pro Ser Glu Leu Arg
650                 655                 660 tac gat atc ttc cca ttc agc aaa gat agt gtt ggt ctt atg ata acc      2112
Tyr Asp Ile Phe Pro Phe Ser Lys Asp Ser Val Gly Leu Met Ile Thr
665                 670                 675                 680 aaa cat ata att gtg aaa gaa ggc aaa gca gag gtt tac aag gca aca      2160
Lys His Ile Ile Val Lys Glu Gly Lys Ala Glu Val Tyr Lys Ala Thr
                685                 690                 695 gac tat gaa aac agc gag aaa gtt gga gaa gtg gat gta aaa gaa acc      2208
Asp Tyr Glu Asn Ser Glu Lys Val Gly Glu Val Asp Val Lys Glu Thr
                700                 705                 710 gac gga gga gtt gag gtt atc gtc ccg ttt gac tac ctg gac agc ccc      2256
Asp Gly Gly Val Glu Val Ile Val Pro Phe Asp Tyr Leu Asp Ser Pro
                715                 720                 725 tct gac ttc tac ttt gct gtc tct acg gtc aat gat caa gga gag ctt      2304
Ser Asp Phe Tyr Phe Ala Val Ser Thr Val Asn Asp Gln Gly Glu Leu
            730                 735                 740 gaa ata ata acg aac ccg ata gaa gta aaa ctt cca aag cag gtt gag      2352
Glu Ile Ile Thr Asn Pro Ile Glu Val Lys Leu Pro Lys Gln Val Glu
745                 750                 755                 760 ggg att gta gtt gca gag atc aag gac att gaa tgg gat gat cat ggt      2400
Gly Ile Val Val Ala Glu Ile Lys Asp Ile Glu Trp Asp Asp His Gly
                765                 770                 775 cct gga act tat acc tat gcc acc aac aag gtt ttc gtt cct gga cac      2448
Pro Gly Thr Tyr Thr Tyr Ala Thr Asn Lys Val Phe Val Pro Gly His
                780                 785                 790 cta gac tta ctt aag gtg aga ata ctc gaa aag cca agt tca tac gtc      2496
Leu Asp Leu Leu Lys Val Arg Ile Leu Glu Lys Pro Ser Ser Tyr Val
            795                 800                 805 ttt gag tac tac ttc aag gat ctt ggg gat aac tca tgg aat ggg cca      2544
Phe Glu Tyr Tyr Phe Lys Asp Leu Gly Asp Asn Ser Trp Asn Gly Pro
810                 815                 820 aat ggg ttc agt ttg cag ata att gag gca tac ttt gac ttc aaa gag      2592
Asn Gly Phe Ser Leu Gln Ile Ile Glu Ala Tyr Phe Asp Phe Lys Glu
825                 830                 835                 840 gga gga aat aca tca gca atc aaa atg ttc cct gat ggg cct gga agc      2640
Gly Gly Asn Thr Ser Ala Ile Lys Met Phe Pro Asp Gly Pro Gly Ser
                845                 850                 855 aac gta gac ctt gat cca gaa cat cca tgg gat gta gcc ctt aga ata      2688
Asn Val Asp Leu Asp Pro Glu His Pro Trp Asp Val Ala Leu Arg Ile
                860                 865                 870 gca ggt tgg gac tat gga aac atc att gtt ctc cca gat gga aca agc      2736
Ala Gly Trp Asp Tyr Gly Asn Ile Ile Val Leu Pro Asp Gly Thr Ser
            875                 880                 885 tat caa ggt gaa atg aaa atc tca gcg gat cct gtt aag aat gca att      2784
Tyr Gln Gly Glu Met Lys Ile Ser Ala Asp Pro Val Lys Asn Ala Ile
            890                 895                 900 gta gta gag gtt cca aag aag tat ctt gag att agc aaa gac tat ggg      2832
Val Val Glu Val Pro Lys Lys Tyr Leu Glu Ile Ser Lys Asp Tyr Gly
905                 910                 915                 920 cta tat gga gcg ata tta gtg ggc tcc caa gat ggt tat gag cct gat      2880
```

-continued

| | | | | | | | | | | | | |
|---|---|---|---|---|---|---|---|---|---|---|---|---|
| Leu | Tyr | Gly | Ala | Ile | Leu | Val | Gly | Ser | Gln | Asp | Gly | Tyr | Glu | Pro | Asp |
| | | | | 925 | | | | 930 | | | | 935 | | | |

```
aag tgg aga cct gtt gca gtt gat gct gag gag tgg aag ggt ggc gga        2928
Lys Trp Arg Pro Val Ala Val Asp Ala Glu Glu Trp Lys Gly Gly Gly
            940             945                 950 gct gac gtt aat gca gtt att gct gga gtt gca cca agg gtc tat gat        2976
Ala Asp Val Asn Ala Val Ile Ala Gly Val Ala Pro Arg Val Tyr Asp
            955             960                 965 ctt tta gtc cca gag gac ttt aag cca aca caa gag gag caa cta agc        3024
Leu Leu Val Pro Glu Asp Phe Lys Pro Thr Gln Glu Glu Gln Leu Ser
    970                 975                 980 agt tat gac gca gag aac gga aag aga gca ata gta aag atg ata cct        3072
Ser Tyr Asp Ala Glu Asn Gly Lys Arg Ala Ile Val Lys Met Ile Pro
985             990                 995                 1000 ctg ttc gga gtt gaa  gaa aag cca agt gaa  acc gag acc ccc act          3117
Leu Phe Gly Val Glu  Glu Lys Pro Ser Glu  Thr Glu Thr Pro Thr
                    1005                 1010                1015 gag act gaa agt cca  aca cca agc gag act  tct tca act gta tct          3162
Glu Thr Glu Ser Pro  Thr Pro Ser Glu Thr  Ser Ser Thr Val Ser
                1020                 1025                 1030 cca agt tca aca agc  tct cca agc cca aca  gaa act gga gga atc          3207
Pro Ser Ser Thr Ser  Ser Pro Ser Pro Thr  Glu Thr Gly Gly Ile
                1035                 1040                 1045 tgc gga cca gca gca  ctc gta gga cta gca  cta atc cca cta ctc          3252
Cys Gly Pro Ala Ala  Leu Val Gly Leu Ala  Leu Ile Pro Leu Leu
                1050                 1055                 1060 cta aga agg agg tgg tga                                                3270
Leu Arg Arg Arg Trp
                1065

<210> SEQ ID NO 4
<211> LENGTH: 1089
<212> TYPE: PRT
<213> ORGANISM: Thermococcus litoralis

<400> SEQUENCE: 4
```

| | | | | | | | | | | | | |
|---|---|---|---|---|---|---|---|---|---|---|---|---|
| Met | Lys | Lys | Gly | Leu | Ala | Met | Phe | Leu | Ile | Phe | Leu | Val | Ala | Leu | Ser |
| | | | | -20 | | | | -15 | | | | -10 | | | |
| Ile | Ala | Glu | Val | Gly | Val | Lys | Ala | Glu | Glu | Pro | Lys | Pro | Leu | Asn | Val |
| | | | -5 | | | | -1 | 1 | | | | 5 | | | |
| Ile | Ile | Val | Trp | His | Gln | His | Gln | Pro | Tyr | Tyr | Asp | Pro | Ile | Gln |
| | 10 | | | | 15 | | | | 20 | | | | | |
| Asp | Ile | Tyr | Thr | Arg | Pro | Trp | Val | Arg | Leu | His | Ala | Ala | Asn | Asn | Tyr |
| 25 | | | | 30 | | | | 35 | | | | 40 | | | |
| Trp | Lys | Met | Ala | Asn | Tyr | Leu | Ser | Lys | Tyr | Pro | Asp | Val | His | Val | Ala |
| | | | 45 | | | | 50 | | | | 55 | | | | |
| Ile | Asp | Leu | Ser | Gly | Ser | Leu | Ile | Ala | Gln | Leu | Ala | Asp | Tyr | Met | Asn |
| | | 60 | | | | 65 | | | | 70 | | | | | |
| Gly | Lys | Lys | Asp | Thr | Tyr | Gln | Ile | Val | Thr | Glu | Lys | Ile | Ala | Asn | Gly |
| | 75 | | | | 80 | | | | 85 | | | | | | |
| Glu | Pro | Leu | Thr | Leu | Glu | Asp | Lys | Trp | Phe | Met | Leu | Gln | Ala | Pro | Gly |
| | 90 | | | | 95 | | | | 100 | | | | | | |
| Gly | Phe | Phe | Asp | His | Thr | Ile | Pro | Trp | Asn | Gly | Glu | Pro | Val | Ala | Asp |
| 105 | | | | 110 | | | | 115 | | | | 120 | | | |
| Glu | Asn | Gly | Asn | Pro | Tyr | Arg | Glu | Gln | Trp | Asp | Arg | Tyr | Ala | Glu | Leu |
| | | | 125 | | | | 130 | | | | 135 | | | | |
| Lys | Asp | Lys | Arg | Asn | Asn | Ala | Phe | Lys | Lys | Tyr | Ala | Asn | Leu | Pro | Leu |
| | | 140 | | | | 145 | | | | 150 | | | | | |

-continued

Asn Glu Gln Lys Val Lys Ile Thr Ala Glu Phe Thr Glu Gln Asp Tyr
    155                 160                 165
Ile Asp Leu Ala Val Leu Phe Asn Leu Ala Trp Ile Asp Tyr Asn Tyr
    170                 175                 180
Ile Ile Asn Thr Pro Glu Leu Lys Ala Leu Tyr Asp Lys Val Asp Val
185                 190                 195                 200
Gly Gly Tyr Thr Lys Glu Asp Val Ala Thr Val Leu Lys His Gln Met
                205                 210                 215
Trp Leu Leu Asn His Thr Phe Glu Glu His Glu Lys Ile Asn Tyr Leu
                220                 225                 230
Leu Gly Asn Gly Asn Val Glu Val Thr Val Val Pro Tyr Ala His Pro
            235                 240                 245
Ile Gly Pro Leu Leu Asn Asp Phe Gly Trp Tyr Glu Asp Phe Asp Ala
        250                 255                 260
His Val Lys Lys Ala His Glu Leu Tyr Lys Lys Tyr Leu Gly Asp Asn
265                 270                 275                 280
Arg Val Glu Pro Gln Gly Gly Trp Ala Ala Glu Ser Ala Leu Asn Asp
                285                 290                 295
Lys Thr Leu Glu Ile Leu Thr Asn Asn Gly Trp Lys Trp Val Met Thr
            300                 305                 310
Asp Gln Met Val Leu Asp Ile Leu Gly Ile Pro Asn Thr Val Glu Asn
        315                 320                 325
Tyr Tyr Lys Pro Trp Val Ala Glu Phe Asn Gly Lys Lys Ile Tyr Leu
    330                 335                 340
Phe Pro Arg Asn His Asp Leu Ser Asp Arg Val Gly Phe Arg Tyr Ser
345                 350                 355                 360
Gly Met Asn Gln Tyr Gln Ala Val Glu Asp Phe Val Asn Glu Leu Leu
                365                 370                 375
Lys Val Gln Lys Glu Asn Tyr Asp Gly Ser Leu Val Tyr Val Val Thr
            380                 385                 390
Leu Asp Gly Glu Asn Pro Trp Glu His Tyr Pro Phe Asp Gly Lys Ile
        395                 400                 405
Phe Leu Glu Glu Leu Tyr Lys Lys Leu Thr Glu Leu Gln Lys Gln Gly
    410                 415                 420
Leu Ile Arg Thr Val Thr Pro Ser Glu Tyr Ile Gln Met Tyr Gly Asp
425                 430                 435                 440
Lys Ala Asn Lys Leu Thr Pro Lys Leu Met Lys Arg Leu Asp Phe Thr
                445                 450                 455
Thr Glu Glu Arg Val Asn Ala Leu Leu Lys Ala Gln Ser Leu Gly Glu
            460                 465                 470
Leu Tyr Asp Met Ala Gly Val Glu Glu Asn Met Gln Trp Pro Glu Ser
        475                 480                 485
Ser Trp Val Asp Gly Thr Leu Ser Thr Trp Ile Gly Glu Pro Gln Glu
    490                 495                 500
Asn Leu Gly Trp Tyr Trp Leu Tyr Leu Gly Arg Lys Ala Leu Phe Glu
505                 510                 515                 520
Asn Lys Asn Lys Val Val Asp Trp Asn Thr Ala Tyr Glu Tyr Leu Leu
                525                 530                 535
Arg Ala Glu Ala Ser Asp Trp Phe Trp Trp Tyr Gly Ser Asp Gln Asp
            540                 545                 550
Ser Gly Gln Asp Tyr Thr Phe Asp Arg Tyr Leu Lys Thr Tyr Leu Tyr
        555                 560                 565
Glu Met Tyr Lys Phe Ala Gly Leu Glu Ile Pro Ser Tyr Leu Phe Gly
    570                 575                 580

```
Asn Tyr Phe Pro Asn Gly Glu Pro Tyr Ala Ile Arg Glu Leu Thr Gly
585                 590                 595                 600

Leu Pro Glu Gly Glu Lys Lys Ser Trp Ser Leu Ser Pro Ile Ala
            605                 610                 615

Glu Gly Val Glu Leu Tyr Phe Asp Glu Gln Gly Leu His Phe Val Val
            620                 625                 630

Lys Thr Thr Lys Glu Phe Glu Ile Ser Ile Phe Glu Pro Gly Lys Val
            635                 640                 645

Met Gly Asn Thr Phe Thr Leu Leu Gln Thr Lys Pro Ser Glu Leu Arg
650                 655                 660

Tyr Asp Ile Phe Pro Phe Ser Lys Asp Ser Val Gly Leu Met Ile Thr
665                 670                 675                 680

Lys His Ile Ile Val Lys Glu Gly Lys Ala Glu Val Tyr Lys Ala Thr
            685                 690                 695

Asp Tyr Glu Asn Ser Glu Lys Val Gly Glu Val Asp Val Lys Glu Thr
            700                 705                 710

Asp Gly Gly Val Glu Val Ile Val Pro Phe Asp Tyr Leu Asp Ser Pro
            715                 720                 725

Ser Asp Phe Tyr Phe Ala Val Ser Thr Val Asn Asp Gln Gly Glu Leu
730                 735                 740

Glu Ile Ile Thr Asn Pro Ile Glu Val Lys Leu Pro Lys Gln Val Glu
745                 750                 755                 760

Gly Ile Val Val Ala Glu Ile Lys Asp Ile Glu Trp Asp Asp His Gly
            765                 770                 775

Pro Gly Thr Tyr Thr Tyr Ala Thr Asn Lys Val Phe Val Pro Gly His
            780                 785                 790

Leu Asp Leu Leu Lys Val Arg Ile Leu Glu Lys Pro Ser Ser Tyr Val
            795                 800                 805

Phe Glu Tyr Tyr Phe Lys Asp Leu Gly Asp Asn Ser Trp Asn Gly Pro
810                 815                 820

Asn Gly Phe Ser Leu Gln Ile Ile Glu Ala Tyr Phe Asp Phe Lys Glu
825                 830                 835                 840

Gly Gly Asn Thr Ser Ala Ile Lys Met Phe Pro Asp Gly Pro Gly Ser
            845                 850                 855

Asn Val Asp Leu Asp Pro Glu His Pro Trp Asp Val Ala Leu Arg Ile
            860                 865                 870

Ala Gly Trp Asp Tyr Gly Asn Ile Ile Val Leu Pro Asp Gly Thr Ser
            875                 880                 885

Tyr Gln Gly Glu Met Lys Ile Ser Ala Asp Pro Val Lys Asn Ala Ile
890                 895                 900

Val Val Glu Val Pro Lys Lys Tyr Leu Glu Ile Ser Lys Asp Tyr Gly
905                 910                 915                 920

Leu Tyr Gly Ala Ile Leu Val Gly Ser Gln Asp Gly Tyr Glu Pro Asp
            925                 930                 935

Lys Trp Arg Pro Val Ala Val Asp Ala Glu Glu Trp Lys Gly Gly Gly
            940                 945                 950

Ala Asp Val Asn Ala Val Ile Ala Gly Val Ala Pro Arg Val Tyr Asp
            955                 960                 965

Leu Leu Val Pro Glu Asp Phe Lys Pro Thr Gln Glu Glu Gln Leu Ser
            970                 975                 980

Ser Tyr Asp Ala Glu Asn Gly Lys Arg Ala Ile Val Lys Met Ile Pro
985                 990                 995                 1000

Leu Phe Gly Val Glu  Glu Lys Pro Ser Glu  Thr Glu Thr Pro Thr
```

```
                                1005                 1010                1015
Glu Thr Glu Ser Pro  Thr Pro Ser Glu Thr  Ser Ser Thr Val Ser
                1020                 1025                1030

Pro Ser Ser Thr Ser  Ser Pro Ser Pro Thr  Glu Thr Gly Gly Ile
                1035                 1040                1045

Cys Gly Pro Ala Ala  Leu Val Gly Leu Ala  Leu Ile Pro Leu Leu
                1050                 1055                1060

Leu Arg Arg Arg Trp
                1065

<210> SEQ ID NO 5
<211> LENGTH: 59
<212> TYPE: PRT
<213> ORGANISM: Thermococcus hydrothermalis
<220> FEATURE:
<221> NAME/KEY: MISC_FEATURE
<222> LOCATION: (1)..(59)
<223> OTHER INFORMATION: Linker

<400> SEQUENCE: 5

Thr Pro Thr Glu Ser  Pro Thr Glu Thr Thr  Thr Thr Thr Pro Ser Glu
1               5                    10                  15

Thr Thr Thr Thr Thr  Ser Thr Thr Thr Gly  Pro Ser Ser Thr Thr Thr
            20                   25                  30

Ser Thr Pro Gly Gly  Gly Ile Cys Gly Pro  Gly Ile Ile Ala Gly Leu
        35                   40                  45

Ala Leu Ile Pro Leu  Leu Leu Lys Arg Arg  Asn
    50                   55

<210> SEQ ID NO 6
<211> LENGTH: 26
<212> TYPE: PRT
<213> ORGANISM: Thermococcus hydrothermalis
<220> FEATURE:
<221> NAME/KEY: SIGNAL
<222> LOCATION: (1)..(26)

<400> SEQUENCE: 6

Met Arg Arg Val Val  Ala Leu Phe Ile Ala  Ile Leu Met Leu Gly Ser
1               5                    10                  15

Ile Val Gly Ala Asn  Val Lys Ser Val Gly
            20                   25

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
cggcgtaagc ttgtttgcct                                                20

<210> SEQ ID NO 8
<211> LENGTH: 38
<212> TYPE: DNA
<213> ORGANISM: Artificial Sequence
<220> FEATURE:
<223> OTHER INFORMATION: Synthetic construct

<400> SEQUENCE: 8
aggcaaacaa gcttacgccg cgcatgatgg agcgcctt                            38
```

-continued

```
<210> SEQ ID NO 9
<211> LENGTH: 37
<212> TYPE: DNA
<213> ORGANISM: Artificial Sequence
<220> FEATURE:
<223> OTHER INFORMATION: Synthetic construct

<400> SEQUENCE: 9
tgattaacgc gtttaagtat agttgccagg gccatgg                              37

<210> SEQ ID NO 10
<211> LENGTH: 29
<212> TYPE: DNA
<213> ORGANISM: Artificial Sequence
<220> FEATURE:
<223> OTHER INFORMATION: Synthetic construct

<400> SEQUENCE: 10
tgattaacgc gtttaaggag gctcaacgc                                       29

<210> SEQ ID NO 11
<211> LENGTH: 34
<212> TYPE: DNA
<213> ORGANISM: Artificial Sequence
<220> FEATURE:
<223> OTHER INFORMATION: Synthetic construct

<400> SEQUENCE: 11
tgattaacgc gtttagtcgt atgatgaaag ttgc                                 34

<210> SEQ ID NO 12
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(14)
<223> OTHER INFORMATION: Putavite Linker

<400> SEQUENCE: 12

Glu Phe His Gln His Gln His Gln His Gln His Gln His Pro
1               5                   10

<210> SEQ ID NO 13
<211> LENGTH: 85
<212> TYPE: PRT
<213> ORGANISM: Artificial Sequence
<220> FEATURE:
<223> OTHER INFORMATION: Syntheric construct
<220> FEATURE:
<221> NAME/KEY: SIGNAL
<222> LOCATION: (1)..(85)

<400> SEQUENCE: 13

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80
```

<210> SEQ ID NO 14
<211> LENGTH: 3798
<212> TYPE: DNA
<213> ORGANISM: Artificial Sequence
<220> FEATURE:
<223> OTHER INFORMATION: Syntheric construct
<220> FEATURE:
<221> NAME/KEY: CDS
<222> LOCATION: (1)..(3798)
<223> OTHER INFORMATION: synthetic DNA from Thermococcus hydrothermalis for Pichia pastoris expression
<220> FEATURE:
<221> NAME/KEY: misc_feature
<222> LOCATION: (3760)..(3795)
<223> OTHER INFORMATION: HQ tag

<400> SEQUENCE: 14

```
gct gag cca aag cct ttg aac gtc atc atc gtt tgg cat cag cac caa      48
Ala Glu Pro Lys Pro Leu Asn Val Ile Ile Val Trp His Gln His Gln
1               5                   10                  15 cct tac tac tac gac cca gtt caa gac gtt tac act aga cct tgg gtc      96
Pro Tyr Tyr Tyr Asp Pro Val Gln Asp Val Tyr Thr Arg Pro Trp Val
            20                  25                  30 aga ttg cat gct gcc aac aac tac tgg aag atg gct cac tac ttg tct     144
Arg Leu His Ala Ala Asn Asn Tyr Trp Lys Met Ala His Tyr Leu Ser
        35                  40                  45 caa tac cct gag gtt cat gct acc atc gac ttg tct ggt tct ttg atc     192
Gln Tyr Pro Glu Val His Ala Thr Ile Asp Leu Ser Gly Ser Leu Ile
    50                  55                  60 gct caa ttg gcc gac tac atg aac ggt aag aag gac act tac caa atc     240
Ala Gln Leu Ala Asp Tyr Met Asn Gly Lys Lys Asp Thr Tyr Gln Ile
65                  70                  75                  80 atc act gag aag atc gcc aac ggt gag cct ttg act gtt gac gag aag     288
Ile Thr Glu Lys Ile Ala Asn Gly Glu Pro Leu Thr Val Asp Glu Lys
                85                  90                  95 tgg ttc atg ttg caa gcc cct gga ggt ttc ttc gac aac act atc cca     336
Trp Phe Met Leu Gln Ala Pro Gly Gly Phe Phe Asp Asn Thr Ile Pro
            100                 105                 110 tgg aac ggt gag cct atc acc gac cca aac gga aac cct atc aga gac     384
Trp Asn Gly Glu Pro Ile Thr Asp Pro Asn Gly Asn Pro Ile Arg Asp
        115                 120                 125 ttc tgg gac aga tac act gag ttg aag aac aag atg ttg tct gcc aag     432
Phe Trp Asp Arg Tyr Thr Glu Leu Lys Asn Lys Met Leu Ser Ala Lys
    130                 135                 140 gcc aag tac gcc aac ttc gtc acc gag tct caa aag gtt gcc gtt acc     480
Ala Lys Tyr Ala Asn Phe Val Thr Glu Ser Gln Lys Val Ala Val Thr
145                 150                 155                 160 aac gag ttc acc gag cag gac tac atc gac ttg gcc gtc ttg ttc aac     528
Asn Glu Phe Thr Glu Gln Asp Tyr Ile Asp Leu Ala Val Leu Phe Asn
                165                 170                 175 ttg gcc tgg atc gac tac aac tac atc acc tct act cca gag ttc aag     576
Leu Ala Trp Ile Asp Tyr Asn Tyr Ile Thr Ser Thr Pro Glu Phe Lys
            180                 185                 190 gca ttg tac gac aag gtt gac gag ggt gga tac aca aga gcc gac gtt     624
Ala Leu Tyr Asp Lys Val Asp Glu Gly Gly Tyr Thr Arg Ala Asp Val
        195                 200                 205 aag acc gtc ttg gac gcc caa atc tgg ttg ttg aac cac acc ttc gag     672
Lys Thr Val Leu Asp Ala Gln Ile Trp Leu Leu Asn His Thr Phe Glu
    210                 215                 220 gag cat gag aag atc aac ttg ttg ttg ggt aac ggt aac gtt gag gtc     720
Glu His Glu Lys Ile Asn Leu Leu Leu Gly Asn Gly Asn Val Glu Val
```

```
              225                 230                 235                 240
aca gtt gtt cct tac gct cac cca atc gga cct atc ttg aac gac ttc      768
Thr Val Val Pro Tyr Ala His Pro Ile Gly Pro Ile Leu Asn Asp Phe
                    245                 250                 255 ggt tgg gac tcc gac ttc aac gac cag gtc aag aag gcc gac gag ttg      816
Gly Trp Asp Ser Asp Phe Asn Asp Gln Val Lys Lys Ala Asp Glu Leu
            260                 265                 270 tac aag cct tac ttg gga gga ggt aca gcc gtt cca aag gga gga tgg      864
Tyr Lys Pro Tyr Leu Gly Gly Gly Thr Ala Val Pro Lys Gly Gly Trp
                275                 280                 285 gct gcc gag tct gct ttg aac gac aag act ttg gag atc ttg gct gag      912
Ala Ala Glu Ser Ala Leu Asn Asp Lys Thr Leu Glu Ile Leu Ala Glu
        290                 295                 300 aac gga tgg gag tgg gtt atg acc gac cag atg gtt ttg ggt aag ttg      960
Asn Gly Trp Glu Trp Val Met Thr Asp Gln Met Val Leu Gly Lys Leu
305                 310                 315                 320 ggt atc gag gga acc gtt gag aac tac cat aag cct tgg gtt gca gag     1008
Gly Ile Glu Gly Thr Val Glu Asn Tyr His Lys Pro Trp Val Ala Glu
                    325                 330                 335 ttc aac ggt aag aag atc tac ttg ttc cca aga aac cac gac ttg tca     1056
Phe Asn Gly Lys Lys Ile Tyr Leu Phe Pro Arg Asn His Asp Leu Ser
            340                 345                 350 gac aga gtt gga ttc act tac tct gga atg aac caa cag caa gct gtt     1104
Asp Arg Val Gly Phe Thr Tyr Ser Gly Met Asn Gln Gln Gln Ala Val
                355                 360                 365 gag gac ttc gtc aac gag ttg ttg aag ttg caa aag caa aac tac gac     1152
Glu Asp Phe Val Asn Glu Leu Leu Lys Leu Gln Lys Gln Asn Tyr Asp
        370                 375                 380 ggt tcc ttg gtt tac gtt gtt act ttg gac gga gag aac cca gtc gag     1200
Gly Ser Leu Val Tyr Val Val Thr Leu Asp Gly Glu Asn Pro Val Glu
385                 390                 395                 400 aac tac cct tac gac ggt gag ttg ttc ttg act gag ttg tac aag aag     1248
Asn Tyr Pro Tyr Asp Gly Glu Leu Phe Leu Thr Glu Leu Tyr Lys Lys
                    405                 410                 415 ttg aca gag ttg caa gag caa gga ttg atc aga act ttg acc cct tca     1296
Leu Thr Glu Leu Gln Glu Gln Gly Leu Ile Arg Thr Leu Thr Pro Ser
            420                 425                 430 gag tac atc cag ttg tac ggt gac aag gcc aac aag ttg act cct aga     1344
Glu Tyr Ile Gln Leu Tyr Gly Asp Lys Ala Asn Lys Leu Thr Pro Arg
                435                 440                 445 atg atg gag aga ttg gac ttg aca ggt gac aac gtc aac gct ttg ttg     1392
Met Met Glu Arg Leu Asp Leu Thr Gly Asp Asn Val Asn Ala Leu Leu
450                 455                 460 aag gcc cag tcc ttg ggt gag ttg tac gac atg acc gga gtc aag gag     1440
Lys Ala Gln Ser Leu Gly Glu Leu Tyr Asp Met Thr Gly Val Lys Glu
465                 470                 475                 480 gag atg caa tgg cca gag agt agt tgg atc gac ggt act ttg agt act     1488
Glu Met Gln Trp Pro Glu Ser Ser Trp Ile Asp Gly Thr Leu Ser Thr
                    485                 490                 495 tgg atc ggt gag cct cag gag aac tac ggt tgg tac tgg ttg tac atg     1536
Trp Ile Gly Glu Pro Gln Glu Asn Tyr Gly Trp Tyr Trp Leu Tyr Met
            500                 505                 510 gcc aga aag gcc ttg atg gag aac aag gac aag atg tca caa gcc gac     1584
Ala Arg Lys Ala Leu Met Glu Asn Lys Asp Lys Met Ser Gln Ala Asp
        515                 520                 525 tgg gag aag gcc tac gag tac ttg ttg aga gcc gag gct tcc gac tgg     1632
Trp Glu Lys Ala Tyr Glu Tyr Leu Leu Arg Ala Glu Ala Ser Asp Trp
    530                 535                 540 ttc tgg tgg tac ggt tcc gac caa gac tct ggt cag gac tac act ttc     1680
Phe Trp Trp Tyr Gly Ser Asp Gln Asp Ser Gly Gln Asp Tyr Thr Phe
```

-continued

```
               545                 550                 555                 560
gac aga tac ttg aag aca tac ttg tac gag atg tac aag ttg gct gga           1728
Asp Arg Tyr Leu Lys Thr Tyr Leu Tyr Glu Met Tyr Lys Leu Ala Gly
            565                 570                 575 gtt gag cct cca tcc tac ttg ttc gga aac tac ttc cca gac gga gag           1776
Val Glu Pro Pro Ser Tyr Leu Phe Gly Asn Tyr Phe Pro Asp Gly Glu
        580                 585                 590 cct tac aca act aga ggt ttg gtt ggt ttg aag gac gga gag atg aag           1824
Pro Tyr Thr Thr Arg Gly Leu Val Gly Leu Lys Asp Gly Glu Met Lys
    595                 600                 605 aac ttc tcc agt atg tca cca ttg gcc aag ggt gtc tct gtc tac ttc           1872
Asn Phe Ser Ser Met Ser Pro Leu Ala Lys Gly Val Ser Val Tyr Phe
610                 615                 620 gac ggt gag ggt atc cat ttc atc gtt aag gga aac ttg gac aga ttc           1920
Asp Gly Glu Gly Ile His Phe Ile Val Lys Gly Asn Leu Asp Arg Phe
625                 630                 635                 640 gag gtc tca atc tgg gag aag gac gag aga gtt ggt aac act ttc act           1968
Glu Val Ser Ile Trp Glu Lys Asp Glu Arg Val Gly Asn Thr Phe Thr
            645                 650                 655 aga ttg cag gag aag cca gac gag ttg tct tac ttc atg ttc cct ttc           2016
Arg Leu Gln Glu Lys Pro Asp Glu Leu Ser Tyr Phe Met Phe Pro Phe
        660                 665                 670 tcc aga gac tct gtt ggt ttg ttg atc aca aag cat gtt gtt tac gag           2064
Ser Arg Asp Ser Val Gly Leu Leu Ile Thr Lys His Val Val Tyr Glu
    675                 680                 685 aac ggt aag gcc gag atc tac ggt gct acc gac tac gag aag tcc gag           2112
Asn Gly Lys Ala Glu Ile Tyr Gly Ala Thr Asp Tyr Glu Lys Ser Glu
690                 695                 700 aag ttg gga gag gcc act gtc aag aac act agt gag gga atc gag gtc           2160
Lys Leu Gly Glu Ala Thr Val Lys Asn Thr Ser Glu Gly Ile Glu Val
705                 710                 715                 720 gtc ttg cct ttc gac tac atc gag aac cca tcc gac ttc tac ttc gcc           2208
Val Leu Pro Phe Asp Tyr Ile Glu Asn Pro Ser Asp Phe Tyr Phe Ala
            725                 730                 735 gtt tcc acc gtc aag gac ggt gac ttg gag gtt atc tcc aca cct gtt           2256
Val Ser Thr Val Lys Asp Gly Asp Leu Glu Val Ile Ser Thr Pro Val
        740                 745                 750 gag ttg aag ttg cct acc gag gtc aag ggt gtt gtt atc gcc gac atc           2304
Glu Leu Lys Leu Pro Thr Glu Val Lys Gly Val Val Ile Ala Asp Ile
    755                 760                 765 aca gac cca gag ggt gac gac cat ggt cca ggt aac tac aca tac cca           2352
Thr Asp Pro Glu Gly Asp Asp His Gly Pro Gly Asn Tyr Thr Tyr Pro
770                 775                 780 acc gac aag gtt ttc aag cca gga gtt ttc gac ttg ttg aga ttc aga           2400
Thr Asp Lys Val Phe Lys Pro Gly Val Phe Asp Leu Leu Arg Phe Arg
785                 790                 795                 800 atg ttg gag caa act gag agt tac gtt atg gag ttc tac ttc aag gac           2448
Met Leu Glu Gln Thr Glu Ser Tyr Val Met Glu Phe Tyr Phe Lys Asp
            805                 810                 815 ttg gga ggt aac cct tgg aac ggt cca aac gga ttc tcc ttg cag atc           2496
Leu Gly Gly Asn Pro Trp Asn Gly Pro Asn Gly Phe Ser Leu Gln Ile
        820                 825                 830 atc gag gtt tac ttg gac ttc aag gac gga gga aac tcc tca gcc atc           2544
Ile Glu Val Tyr Leu Asp Phe Lys Asp Gly Gly Asn Ser Ser Ala Ile
    835                 840                 845 aag atg ttc cca gac gga cct gga gcc aac gtt aac ttg gac cca gag           2592
Lys Met Phe Pro Asp Gly Pro Gly Ala Asn Val Asn Leu Asp Pro Glu
850                 855                 860 cac cca tgg gac gtt gcc ttc aga att gcc ggt tgg gac tac gga aac           2640
His Pro Trp Asp Val Ala Phe Arg Ile Ala Gly Trp Asp Tyr Gly Asn
```

-continued

| | | | | | | | | | | | | | | | |
|---|---|---|---|---|---|---|---|---|---|---|---|---|---|---|---|
| | 865 | | | 870 | | | | 875 | | | | 880 | | | |
| ttg | atc | atc | ttg | cca | aac | gga | act | gcc | atc | caa | ggt | gag | atg | caa | atc | 2688 |
| Leu | Ile | Ile | Leu | Pro | Asn | Gly | Thr | Ala | Ile | Gln | Gly | Glu | Met | Gln | Ile | |
| | | | | 885 | | | | | 890 | | | | | 895 | | |
| tct | gcc | gac | cct | gtc | aag | aac | gct | atc | atc | gtt | aag | gtt | cct | aag | aag | 2736 |
| Ser | Ala | Asp | Pro | Val | Lys | Asn | Ala | Ile | Ile | Val | Lys | Val | Pro | Lys | Lys | |
| | | 900 | | | | | 905 | | | | | 910 | | | | |
| tac | atc | gcc | atc | aac | gag | gac | tac | ggt | ttg | tgg | ggt | gac | gtc | ttg | gtt | 2784 |
| Tyr | Ile | Ala | Ile | Asn | Glu | Asp | Tyr | Gly | Leu | Trp | Gly | Asp | Val | Leu | Val | |
| | | | 915 | | | | | 920 | | | | | 925 | | | |
| gga | tca | cag | gac | ggt | tac | gga | cca | gac | aag | tgg | aga | aca | gct | gcc | gtc | 2832 |
| Gly | Ser | Gln | Asp | Gly | Tyr | Gly | Pro | Asp | Lys | Trp | Arg | Thr | Ala | Ala | Val | |
| | 930 | | | | | 935 | | | | | 940 | | | | | |
| gac | gcc | gag | caa | tgg | aag | ttg | gga | gga | gcc | gac | cca | caa | gct | gtt | atc | 2880 |
| Asp | Ala | Glu | Gln | Trp | Lys | Leu | Gly | Gly | Ala | Asp | Pro | Gln | Ala | Val | Ile | |
| 945 | | | | | 950 | | | | | 955 | | | | | 960 | |
| aac | gga | gtt | gct | cct | aga | gtt | atc | gac | gag | ttg | gtt | cca | cag | gga | ttc | 2928 |
| Asn | Gly | Val | Ala | Pro | Arg | Val | Ile | Asp | Glu | Leu | Val | Pro | Gln | Gly | Phe | |
| | | | | 965 | | | | | 970 | | | | | 975 | | |
| gag | cca | aca | cag | gag | gag | caa | ttg | tcc | tcc | tac | gac | gcc | aac | gac | atg | 2976 |
| Glu | Pro | Thr | Gln | Glu | Glu | Gln | Leu | Ser | Ser | Tyr | Asp | Ala | Asn | Asp | Met | |
| | | | 980 | | | | | 985 | | | | | 990 | | | |
| aag | ttg | gct | acc | gtc | aag | gca | ttg | ttg | ttg | ttg | aag | caa | ggt | atc | gtt | 3024 |
| Lys | Leu | Ala | Thr | Val | Lys | Ala | Leu | Leu | Leu | Leu | Lys | Gln | Gly | Ile | Val | |
| | | | 995 | | | | | 1000 | | | | | 1005 | | | |
| gtt | aca | gac | cct | gag | ggt | gac | gac | cat | gga | cca | gga | aca | tac | aca | | 3069 |
| Val | Thr | Asp | Pro | Glu | Gly | Asp | Asp | His | Gly | Pro | Gly | Thr | Tyr | Thr | | |
| | 1010 | | | | | 1015 | | | | | 1020 | | | | | |
| tac | cct | acc | gac | aag | gtt | ttc | aag | cca | ggt | gtt | ttc | gac | ttg | ttg | | 3114 |
| Tyr | Pro | Thr | Asp | Lys | Val | Phe | Lys | Pro | Gly | Val | Phe | Asp | Leu | Leu | | |
| | 1025 | | | | | 1030 | | | | | 1035 | | | | | |
| aag | ttc | aag | gtt | aca | gag | gga | agt | gac | gac | tgg | act | ttg | gag | ttc | | 3159 |
| Lys | Phe | Lys | Val | Thr | Glu | Gly | Ser | Asp | Asp | Trp | Thr | Leu | Glu | Phe | | |
| | 1040 | | | | | 1045 | | | | | 1050 | | | | | |
| cat | ttc | aag | gac | ttg | gga | ggt | aac | cct | tgg | aac | ggt | cca | aac | ggt | | 3204 |
| His | Phe | Lys | Asp | Leu | Gly | Gly | Asn | Pro | Trp | Asn | Gly | Pro | Asn | Gly | | |
| | 1055 | | | | | 1060 | | | | | 1065 | | | | | |
| ttc | tct | ttg | cag | atc | atc | gag | gtt | tac | ttc | gac | ttc | aag | gag | gga | | 3249 |
| Phe | Ser | Leu | Gln | Ile | Ile | Glu | Val | Tyr | Phe | Asp | Phe | Lys | Glu | Gly | | |
| | 1070 | | | | | 1075 | | | | | 1080 | | | | | |
| ggt | aac | gtc | tcc | gcc | atc | aag | atg | ttc | cca | gac | ggt | cct | gga | tca | | 3294 |
| Gly | Asn | Val | Ser | Ala | Ile | Lys | Met | Phe | Pro | Asp | Gly | Pro | Gly | Ser | | |
| | 1085 | | | | | 1090 | | | | | 1095 | | | | | |
| aac | gtt | aga | ttg | gac | cca | aat | cac | cca | tgg | gac | ttg | gcc | ttg | aga | | 3339 |
| Asn | Val | Arg | Leu | Asp | Pro | Asn | His | Pro | Trp | Asp | Leu | Ala | Leu | Arg | | |
| | 1100 | | | | | 1105 | | | | | 1110 | | | | | |
| att | gcc | ggt | tgg | gac | tac | ggt | aac | ttg | atc | atc | ttg | cca | gac | ggt | | 3384 |
| Ile | Ala | Gly | Trp | Asp | Tyr | Gly | Asn | Leu | Ile | Ile | Leu | Pro | Asp | Gly | | |
| | 1115 | | | | | 1120 | | | | | 1125 | | | | | |
| acc | gcc | tac | cag | ggt | gag | atg | caa | atc | tct | gcc | gac | cca | gtt | aag | | 3429 |
| Thr | Ala | Tyr | Gln | Gly | Glu | Met | Gln | Ile | Ser | Ala | Asp | Pro | Val | Lys | | |
| | 1130 | | | | | 1135 | | | | | 1140 | | | | | |
| aac | gcc | atc | atc | gtc | aag | gtt | cct | aag | aag | tac | ttg | aac | atc | tca | | 3474 |
| Asn | Ala | Ile | Ile | Val | Lys | Val | Pro | Lys | Lys | Tyr | Leu | Asn | Ile | Ser | | |
| | 1145 | | | | | 1150 | | | | | 1155 | | | | | |
| gac | tac | gga | ttg | tac | aca | gcc | gtc | atc | gtt | gga | tct | cag | gac | ggt | | 3519 |
| Asp | Tyr | Gly | Leu | Tyr | Thr | Ala | Val | Ile | Val | Gly | Ser | Gln | Asp | Gly | | |
| | 1160 | | | | | 1165 | | | | | 1170 | | | | | |
| tac | ggt | cca | gac | aag | tgg | aga | cct | gtt | gct | gcc | gag | gct | gag | caa | | 3564 |
| Tyr | Gly | Pro | Asp | Lys | Trp | Arg | Pro | Val | Ala | Ala | Glu | Ala | Glu | Gln | | |

| | | | | | | | | | | | | | |
|---|---|---|---|---|---|---|---|---|---|---|---|---|---|
| | | 1175 | | | | 1180 | | | | | 1185 | | |
| tgg | aag | ttg | ggt | ggt | gcc | gac | cca | caa | gct | gtt | atc | gac | aac ttg |
| Trp | Lys | Leu | Gly | Gly | Ala | Asp | Pro | Gln | Ala | Val | Ile | Asp | Asn Leu |
| | 1190 | | | | | 1195 | | | | | 1200 | | |
| gtt | cca | aga | gtt | gtt | gac | gag | ttg | gtt | cca | gag | gga | ttc | aag cca |
| Val | Pro | Arg | Val | Val | Asp | Glu | Leu | Val | Pro | Glu | Gly | Phe | Lys Pro |
| | 1205 | | | | | 1210 | | | | | 1215 | | |
| aca | cag | gag | gag | caa | ttg | tct | tca | tac | gac | ttg | gag | aag | aag act |
| Thr | Gln | Glu | Glu | Gln | Leu | Ser | Ser | Tyr | Asp | Leu | Glu | Lys | Lys Thr |
| | 1220 | | | | | 1225 | | | | | 1230 | | |
| ttg | gcc | act | gtt | ttg | atg | gtt | cca | ttg | gtt | aac | gga | act | ggt gga |
| Leu | Ala | Thr | Val | Leu | Met | Val | Pro | Leu | Val | Asn | Gly | Thr | Gly Gly |
| | 1235 | | | | | 1240 | | | | | 1245 | | |
| gag | gag | cca | gaa | ttc | cat | cag | cac | caa | cat | caa | cac | caa | cat cag |
| Glu | Glu | Pro | Glu | Phe | His | Gln | His | Gln | His | Gln | His | Gln | His Gln |
| | 1250 | | | | | 1255 | | | | | 1260 | | |
| cac | cca | taa | | | | | | | | | | | |
| His | Pro | | | | | | | | | | | | |
| | 1265 | | | | | | | | | | | | |

3609

3654

3699

3744

3789

3798

<210> SEQ ID NO 15
<211> LENGTH: 1265
<212> TYPE: PRT
<213> ORGANISM: Artificial Sequence
<220> FEATURE:
<223> OTHER INFORMATION: Synthetic Construct

<400> SEQUENCE: 15

Ala Glu Pro Lys Pro Leu Asn Val Ile Ile Val Trp His Gln His Gln
1               5                   10                  15

Pro Tyr Tyr Tyr Asp Pro Val Gln Asp Val Tyr Thr Arg Pro Trp Val
            20                  25                  30

Arg Leu His Ala Ala Asn Asn Tyr Trp Lys Met Ala His Tyr Leu Ser
        35                  40                  45

Gln Tyr Pro Glu Val His Ala Thr Ile Asp Leu Ser Gly Ser Leu Ile
    50                  55                  60

Ala Gln Leu Ala Asp Tyr Met Asn Gly Lys Lys Asp Thr Tyr Gln Ile
65                  70                  75                  80

Ile Thr Glu Lys Ile Ala Asn Gly Glu Pro Leu Thr Val Asp Glu Lys
                85                  90                  95

Trp Phe Met Leu Gln Ala Pro Gly Gly Phe Phe Asp Asn Thr Ile Pro
            100                 105                 110

Trp Asn Gly Glu Pro Ile Thr Asp Pro Asn Gly Asn Pro Ile Arg Asp
        115                 120                 125

Phe Trp Asp Arg Tyr Thr Glu Leu Lys Asn Lys Met Leu Ser Ala Lys
    130                 135                 140

Ala Lys Tyr Ala Asn Phe Val Thr Glu Ser Gln Lys Val Ala Val Thr
145                 150                 155                 160

Asn Glu Phe Thr Glu Gln Asp Tyr Ile Asp Leu Ala Val Leu Phe Asn
                165                 170                 175

Leu Ala Trp Ile Asp Tyr Asn Tyr Ile Thr Ser Thr Pro Glu Phe Lys
            180                 185                 190

Ala Leu Tyr Asp Lys Val Asp Glu Gly Gly Tyr Thr Arg Ala Asp Val
        195                 200                 205

Lys Thr Val Leu Asp Ala Gln Ile Trp Leu Leu Asn His Thr Phe Glu
    210                 215                 220

Glu His Glu Lys Ile Asn Leu Leu Leu Gly Asn Gly Asn Val Glu Val
225                 230                 235                 240

-continued

Thr Val Val Pro Tyr Ala His Pro Ile Gly Pro Ile Leu Asn Asp Phe
        245                 250                 255

Gly Trp Asp Ser Asp Phe Asn Asp Gln Val Lys Lys Ala Asp Glu Leu
            260                 265                 270

Tyr Lys Pro Tyr Leu Gly Gly Thr Ala Val Pro Lys Gly Gly Trp
        275                 280                 285

Ala Ala Glu Ser Ala Leu Asn Asp Lys Thr Leu Glu Ile Leu Ala Glu
    290                 295                 300

Asn Gly Trp Glu Trp Val Met Thr Asp Gln Met Val Leu Gly Lys Leu
305                 310                 315                 320

Gly Ile Glu Gly Thr Val Glu Asn Tyr His Lys Pro Trp Val Ala Glu
                325                 330                 335

Phe Asn Gly Lys Lys Ile Tyr Leu Phe Pro Arg Asn His Asp Leu Ser
            340                 345                 350

Asp Arg Val Gly Phe Thr Tyr Ser Gly Met Asn Gln Gln Ala Val
        355                 360                 365

Glu Asp Phe Val Asn Glu Leu Leu Lys Leu Gln Lys Gln Asn Tyr Asp
    370                 375                 380

Gly Ser Leu Val Tyr Val Val Thr Leu Asp Gly Glu Asn Pro Val Glu
385                 390                 395                 400

Asn Tyr Pro Tyr Asp Gly Glu Leu Phe Leu Thr Glu Leu Tyr Lys Lys
                405                 410                 415

Leu Thr Glu Leu Gln Glu Gln Gly Leu Ile Arg Thr Leu Thr Pro Ser
        420                 425                 430

Glu Tyr Ile Gln Leu Tyr Gly Asp Lys Ala Asn Lys Leu Thr Pro Arg
    435                 440                 445

Met Met Glu Arg Leu Asp Leu Thr Gly Asp Asn Val Asn Ala Leu Leu
450                 455                 460

Lys Ala Gln Ser Leu Gly Glu Leu Tyr Asp Met Thr Gly Val Lys Glu
465                 470                 475                 480

Glu Met Gln Trp Pro Glu Ser Ser Trp Ile Asp Gly Thr Leu Ser Thr
                485                 490                 495

Trp Ile Gly Glu Pro Gln Glu Asn Tyr Gly Trp Tyr Trp Leu Tyr Met
            500                 505                 510

Ala Arg Lys Ala Leu Met Glu Asn Lys Asp Lys Met Ser Gln Ala Asp
        515                 520                 525

Trp Glu Lys Ala Tyr Glu Tyr Leu Leu Arg Ala Glu Ala Ser Asp Trp
    530                 535                 540

Phe Trp Trp Tyr Gly Ser Asp Gln Asp Ser Gly Gln Asp Tyr Thr Phe
545                 550                 555                 560

Asp Arg Tyr Leu Lys Thr Tyr Leu Tyr Glu Met Tyr Lys Leu Ala Gly
                565                 570                 575

Val Glu Pro Pro Ser Tyr Leu Phe Gly Asn Tyr Phe Pro Asp Gly Glu
            580                 585                 590

Pro Tyr Thr Thr Arg Gly Leu Val Gly Leu Lys Asp Gly Glu Met Lys
        595                 600                 605

Asn Phe Ser Ser Met Ser Pro Leu Ala Lys Gly Val Ser Val Tyr Phe
    610                 615                 620

Asp Gly Glu Gly Ile His Phe Ile Val Lys Gly Asn Leu Asp Arg Phe
625                 630                 635                 640

Glu Val Ser Ile Trp Glu Lys Asp Glu Arg Val Gly Asn Thr Phe Thr
                645                 650                 655

Arg Leu Gln Glu Lys Pro Asp Glu Leu Ser Tyr Phe Met Phe Pro Phe

```
                       660                 665                 670
Ser Arg Asp Ser Val Gly Leu Leu Ile Thr Lys His Val Val Tyr Glu
            675                 680                 685
Asn Gly Lys Ala Glu Ile Tyr Gly Ala Thr Asp Tyr Glu Lys Ser Glu
            690                 695                 700
Lys Leu Gly Glu Ala Thr Val Lys Asn Thr Ser Glu Gly Ile Glu Val
705                 710                 715                 720
Val Leu Pro Phe Asp Tyr Ile Glu Asn Pro Ser Asp Phe Tyr Phe Ala
            725                 730                 735
Val Ser Thr Val Lys Asp Gly Asp Leu Glu Val Ile Ser Thr Pro Val
            740                 745                 750
Glu Leu Lys Leu Pro Thr Glu Val Lys Gly Val Val Ile Ala Asp Ile
            755                 760                 765
Thr Asp Pro Glu Gly Asp Asp His Gly Pro Gly Asn Tyr Thr Tyr Pro
            770                 775                 780
Thr Asp Lys Val Phe Lys Pro Gly Val Phe Asp Leu Leu Arg Phe Arg
785                 790                 795                 800
Met Leu Glu Gln Thr Glu Ser Tyr Val Met Glu Phe Tyr Phe Lys Asp
            805                 810                 815
Leu Gly Gly Asn Pro Trp Asn Gly Pro Asn Gly Phe Ser Leu Gln Ile
            820                 825                 830
Ile Glu Val Tyr Leu Asp Phe Lys Asp Gly Gly Asn Ser Ser Ala Ile
            835                 840                 845
Lys Met Phe Pro Asp Gly Pro Gly Ala Asn Val Asn Leu Asp Pro Glu
            850                 855                 860
His Pro Trp Asp Val Ala Phe Arg Ile Ala Gly Trp Asp Tyr Gly Asn
865                 870                 875                 880
Leu Ile Ile Leu Pro Asn Gly Thr Ala Ile Gln Gly Glu Met Gln Ile
            885                 890                 895
Ser Ala Asp Pro Val Lys Asn Ala Ile Ile Val Lys Val Pro Lys Lys
            900                 905                 910
Tyr Ile Ala Ile Asn Glu Asp Tyr Gly Leu Trp Gly Asp Val Leu Val
            915                 920                 925
Gly Ser Gln Asp Gly Tyr Gly Pro Asp Lys Trp Arg Thr Ala Ala Val
930                 935                 940
Asp Ala Glu Gln Trp Lys Leu Gly Gly Ala Asp Pro Gln Ala Val Ile
945                 950                 955                 960
Asn Gly Val Ala Pro Arg Val Ile Asp Glu Leu Val Pro Gln Gly Phe
            965                 970                 975
Glu Pro Thr Gln Glu Glu Gln Leu Ser Ser Tyr Asp Ala Asn Asp Met
            980                 985                 990
Lys Leu Ala Thr Val Lys Ala Leu Leu Leu Lys Gln Gly Ile Val
            995                 1000                1005
Val Thr Asp Pro Glu Gly Asp His Gly Pro Gly Thr Tyr Thr
            1010                1015                1020
Tyr Pro Thr Asp Lys Val Phe Lys Pro Gly Val Phe Asp Leu Leu
            1025                1030                1035
Lys Phe Lys Val Thr Glu Gly Ser Asp Asp Trp Thr Leu Glu Phe
            1040                1045                1050
His Phe Lys Asp Leu Gly Gly Asn Pro Trp Asn Gly Pro Asn Gly
            1055                1060                1065
Phe Ser Leu Gln Ile Ile Glu Val Tyr Phe Asp Phe Lys Glu Gly
            1070                1075                1080
```

```
Gly Asn Val Ser Ala Ile Lys Met Phe Pro Asp Gly Pro Gly Ser
    1085                1090                1095

Asn Val Arg Leu Asp Pro Asn His Pro Trp Asp Leu Ala Leu Arg
    1100                1105                1110

Ile Ala Gly Trp Asp Tyr Gly Asn Leu Ile Ile Leu Pro Asp Gly
    1115                1120                1125

Thr Ala Tyr Gln Gly Glu Met Gln Ile Ser Ala Asp Pro Val Lys
    1130                1135                1140

Asn Ala Ile Ile Val Lys Val Pro Lys Lys Tyr Leu Asn Ile Ser
    1145                1150                1155

Asp Tyr Gly Leu Tyr Thr Ala Val Ile Val Gly Ser Gln Asp Gly
    1160                1165                1170

Tyr Gly Pro Asp Lys Trp Arg Pro Val Ala Ala Glu Ala Glu Gln
    1175                1180                1185

Trp Lys Leu Gly Gly Ala Asp Pro Gln Ala Val Ile Asp Asn Leu
    1190                1195                1200

Val Pro Arg Val Val Asp Glu Leu Val Pro Glu Gly Phe Lys Pro
    1205                1210                1215

Thr Gln Glu Glu Gln Leu Ser Ser Tyr Asp Leu Glu Lys Lys Thr
    1220                1225                1230

Leu Ala Thr Val Leu Met Val Pro Leu Val Asn Gly Thr Gly Gly
    1235                1240                1245

Glu Glu Pro Glu Phe His Gln His Gln His Gln Gln His Gln
    1250                1255                1260

His Pro
    1265

<210> SEQ ID NO 16
<211> LENGTH: 44
<212> TYPE: DNA
<213> ORGANISM: Artificial Sequence
<220> FEATURE:
<223> OTHER INFORMATION: Synthetic construct

<400> SEQUENCE: 16
aggggtatct ctcgagaaaa gagctgagcc aaagcctttg aacg                          44

<210> SEQ ID NO 17
<211> LENGTH: 36
<212> TYPE: DNA
<213> ORGANISM: Artificial Sequence
<220> FEATURE:
<223> OTHER INFORMATION: Synthetic construct

<400> SEQUENCE: 17
ggtgctgatg gaattctggc tcctctccac cagttc                                  36

<210> SEQ ID NO 18
<211> LENGTH: 27
<212> TYPE: PRT
<213> ORGANISM: Thermococcus hydrothermalis
<220> FEATURE:
<221> NAME/KEY: SIGNAL
<222> LOCATION: (1)..(27)
<223> OTHER INFORMATION: aprH signal peptide

<400> SEQUENCE: 18

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```

<210> SEQ ID NO 19
<211> LENGTH: 36
<212> TYPE: PRT
<213> ORGANISM: Thermococcus hydrothermalis
<220> FEATURE:
<221> NAME/KEY: MISC_FEATURE
<222> LOCATION: (1)..(36)
<223> OTHER INFORMATION: aprH signal peptide incl HQ tag

<400> SEQUENCE: 19

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala His Gln His Gln His
            20                  25                  30

Gln His Pro Arg
        35
```

<210> SEQ ID NO 20
<211> LENGTH: 189
<212> TYPE: PRT
<213> ORGANISM: Thermococcus hydrothermalis
<220> FEATURE:
<221> NAME/KEY: DOMAIN
<222> LOCATION: (1)..(189)
<223> OTHER INFORMATION: X47 domain

<400> SEQUENCE: 20

```
Ser Tyr Leu Phe Gly Asn Tyr Phe Pro Asp Gly Glu Pro Tyr Thr Thr
1               5                   10                  15

Arg Gly Leu Val Gly Leu Lys Asp Gly Glu Met Lys Asn Phe Ser Ser
            20                  25                  30

Met Ser Pro Leu Ala Lys Gly Val Ser Val Tyr Phe Asp Gly Glu Gly
        35                  40                  45

Ile His Phe Ile Val Lys Gly Asn Leu Asp Arg Phe Glu Val Ser Ile
    50                  55                  60

Trp Glu Lys Asp Glu Arg Val Gly Asn Thr Phe Thr Arg Leu Gln Glu
65                  70                  75                  80

Lys Pro Asp Glu Leu Ser Tyr Phe Met Phe Pro Ser Arg Asp Ser
                85                  90                  95

Val Gly Leu Leu Ile Thr Lys His Val Val Tyr Glu Asn Gly Lys Ala
            100                 105                 110

Glu Ile Tyr Gly Ala Thr Asp Tyr Glu Lys Ser Glu Lys Leu Gly Glu
        115                 120                 125

Ala Thr Val Lys Asn Thr Ser Glu Gly Ile Glu Val Val Leu Pro Phe
    130                 135                 140

Asp Tyr Ile Glu Asn Pro Ser Asp Phe Tyr Phe Ala Val Ser Thr Val
145                 150                 155                 160

Lys Asp Gly Asp Leu Glu Val Ile Ser Thr Pro Val Glu Leu Lys Leu
                165                 170                 175

Pro Thr Glu Val Lys Gly Val Val Ile Ala Asp Ile Thr
            180                 185
```

<210> SEQ ID NO 21
<211> LENGTH: 189
<212> TYPE: PRT
<213> ORGANISM: Pyrococcus abyssi
<220> FEATURE:
<221> NAME/KEY: DOMAIN
<222> LOCATION: (1)..(189)
<223> OTHER INFORMATION: X47 domain

```
<400> SEQUENCE: 21

Ser Tyr Leu Phe Gly Asn Tyr Tyr Pro Asp Gly Glu Pro Tyr Ile Val
1               5                   10                  15

Arg Ala Leu Val Gly Leu Pro Glu Gly Val Lys Lys Asn Trp Ser Ser
            20                  25                  30

Leu Ser Pro Leu Ala Lys Gly Ile Glu Val Tyr Phe Asp Asp Glu Gly
        35                  40                  45

Leu His Phe Val Val Leu Thr Asn Arg Ser Phe Glu Ile Ser Ile Tyr
    50                  55                  60

Glu Pro Glu Lys Ile Ile Gly Asn Thr Phe Thr Val Leu Gln Lys Lys
65                  70                  75                  80

Pro Glu Glu Phe Arg Tyr Ser Glu Val Pro Phe Ser Lys Asp Ser Val
                85                  90                  95

Gly Leu Leu Ile Thr Thr His Ile Thr Val Lys Gly Glu Arg Gly Glu
            100                 105                 110

Val Phe Lys Ala Thr Ser Tyr Asp Asn Tyr Lys Lys Val Gly Glu Val
        115                 120                 125

Lys Val Asn Ala Ile Asn Gly Gly Tyr Glu Val Val Pro Phe Asp
130                 135                 140

Tyr Ile Glu Thr Pro Ser Asp Phe Tyr Phe Ala Val Ser Thr Ile Asn
145                 150                 155                 160

Asp Asn Gly Ser Leu Glu Ile Ile Thr Thr Pro Ile His Leu Lys Leu
                165                 170                 175

Pro Lys Glu Ile Glu Gly Thr Leu Ile Thr Glu Ile Lys
                180                 185

<210> SEQ ID NO 22
<211> LENGTH: 189
<212> TYPE: PRT
<213> ORGANISM: Thermococcus gammatolerans
<220> FEATURE:
<221> NAME/KEY: DOMAIN
<222> LOCATION: (1)..(189)
<223> OTHER INFORMATION: X47 domain

<400> SEQUENCE: 22

Asp Tyr Leu Tyr Gly Asn Tyr Tyr Pro Asp Gly Glu Pro Tyr Leu Arg
1               5                   10                  15

Arg Ala Leu Asp Gly Leu Lys Glu Gly Gln Val Arg Thr Tyr Ser Ser
            20                  25                  30

Leu Ser Pro Leu Ala Glu Asn Val Ser Val Tyr Phe Asp Gly Glu Gly
        35                  40                  45

Leu His Phe Val Leu Asn Gly Asn Leu Ser Glu Phe Glu Val Ser Leu
    50                  55                  60

Tyr Glu Val Asn Arg His Val Gly Asn Thr Phe Thr Leu Leu Gln Ser
65                  70                  75                  80

Arg Pro Asp Glu Leu Ser Tyr Ser Thr Trp Pro Phe Ser Lys Asp Ser
                85                  90                  95

Val Gly Leu Met Ile Thr Lys His Ile Val Tyr Arg Asn Gly Thr Ala
            100                 105                 110

Glu Leu Tyr Asn Ala Thr Asp Tyr Asp Asn Ser Thr Leu Leu Gly Asn
        115                 120                 125

Leu Thr Val Lys Lys Thr Glu Asp Ser Val Asp Ile Thr Val Pro Phe
130                 135                 140

Asp Asn Leu Glu Ser Pro Ser Asp Phe Tyr Phe Ala Val Ser Thr Val
145                 150                 155                 160
```

```
Arg Asn Gly Ser Leu Glu Val Ile Ser Thr Pro Val Glu Leu Lys Leu
                165                 170                 175

Pro Thr Gln Val Lys Gly Ala Ile Ile Ala Asp Ile Lys
            180                 185
```

<210> SEQ ID NO 23
<211> LENGTH: 189
<212> TYPE: PRT
<213> ORGANISM: Thermococcus sp.
<220> FEATURE:
<221> NAME/KEY: DOMAIN
<222> LOCATION: (1)..(189)
<223> OTHER INFORMATION: X47 domain

<400> SEQUENCE: 23

```
Asp Tyr Leu Tyr Gly Asn Tyr Tyr Pro Asp Gly Glu Pro Tyr Ile Arg
1               5                   10                  15

Arg Ser Leu Asp Gly Leu Lys Glu Gly Gln Val Arg Thr Tyr Ser Ser
                20                  25                  30

Leu Ser Pro Leu Ala Lys Asn Val Ser Val Tyr Phe Asp Gly Lys Gly
            35                  40                  45

Leu His Phe Val Leu Asn Gly Asn Leu Ser Glu Phe Glu Val Ser Leu
        50                  55                  60

Tyr Glu Val Asn Arg Arg Val Gly Asn Thr Phe Thr Leu Leu Gln Ser
65                  70                  75                  80

Arg Pro Asp Glu Leu Arg Tyr Ser Thr Trp Pro Phe Ser Lys Asp Ser
                85                  90                  95

Val Gly Leu Met Ile Thr Lys His Ile Leu Tyr Arg Asn Gly Thr Ala
            100                 105                 110

Glu Ile Tyr Asn Ala Thr Gly Tyr Asp Asn Ser Thr Leu Leu Gly Asn
        115                 120                 125

Leu Thr Val Glu Arg Thr Gly Asp Ser Val Glu Ile Thr Val Pro Phe
    130                 135                 140

Asp Tyr Ile Glu Ser Pro Ser Asp Phe Tyr Phe Ala Val Ser Thr Val
145                 150                 155                 160

Arg Asn Gly Ser Leu Glu Thr Ile Ser Thr Pro Val Glu Leu Lys Leu
                165                 170                 175

Pro Thr Gln Val Lys Gly Val Val Ile Ala Asp Ile Lys
            180                 185
```

<210> SEQ ID NO 24
<211> LENGTH: 190
<212> TYPE: PRT
<213> ORGANISM: Pyrococcus furiosus
<220> FEATURE:
<221> NAME/KEY: DOMAIN
<222> LOCATION: (1)..(190)
<223> OTHER INFORMATION: X47 domain

<400> SEQUENCE: 24

```
Ser Tyr Leu Tyr Gly Asn Tyr Phe Pro Asp Gly Ala Pro Tyr Thr Val
1               5                   10                  15

Arg Ala Leu Glu Gly Leu Lys Glu Gly Asp Val Lys Tyr Ser Ser
                20                  25                  30

Leu Ser Pro Val Ala Glu Gly Val Lys Val Phe Phe Asp Ser Gln Gly
            35                  40                  45

Leu His Phe Ile Ile Lys Gly Ser Leu Asp Lys Phe Glu Ile Ser Ile
        50                  55                  60

Tyr Glu Lys Asp Lys Arg Ile Gly Asn Thr Phe Thr Leu Leu Gln Lys
65                  70                  75                  80
```

```
Lys Pro Asp Lys Ile Arg Tyr Asp Val Phe Pro Phe Val Arg Asp Ser
                85                  90                  95

Val Gly Leu Met Ile Thr Lys His Ile Val Tyr Lys Asp Gly Lys Ala
            100                 105                 110

Glu Ile Tyr Asn Ala Thr Asp Tyr Glu Gly Tyr Glu Lys Ile Gly Glu
        115                 120                 125

Ala Gln Val Ser Val Asn Gly Asp Glu Ile Glu Val Ile Val Pro Phe
130                 135                 140

Glu Tyr Leu Glu Thr Pro Glu Asp Phe Tyr Phe Ala Val Ser Thr Val
145                 150                 155                 160

Asp Glu Leu Gly Met Leu Glu Val Ile Thr Thr Pro Val Asn Leu Lys
                165                 170                 175

Leu Pro Val Gln Val Lys Gly Val Val Leu Val Asp Ile Ala
            180                 185                 190
```

<210> SEQ ID NO 25
<211> LENGTH: 188
<212> TYPE: PRT
<213> ORGANISM: Thermococcus barophilus
<220> FEATURE:
<221> NAME/KEY: DOMAIN
<222> LOCATION: (1)..(188)
<223> OTHER INFORMATION: X47 domain

<400> SEQUENCE: 25

```
Ser Tyr Leu Tyr Gly Asn Tyr Phe Pro Asp Gly Gln Pro Tyr Arg Val
1               5                   10                  15

Arg Glu Leu Ser Gly Leu Gly Glu Gly Lys Lys Thr Tyr Ser Ser
            20                  25                  30

Leu Ser Ala Ser Ala Lys Glu Val Glu Val Tyr Phe Asp Lys Asp Gly
        35                  40                  45

Met His Phe Val Ile Lys Gly Ala Pro Glu Gln Phe Glu Ile Ser Ile
50                  55                  60

Tyr Glu Lys Gly Lys Ile Ile Gly Asn Thr Phe Thr Leu Leu Gln Gly
65                  70                  75                  80

Thr Pro Lys Tyr Glu Tyr Ser Leu Phe Pro Tyr Ile Arg Asp Ser Ile
                85                  90                  95

Gly Leu Met Ile Thr Lys His Val Tyr Lys Asp Gly Lys Ala Glu
            100                 105                 110

Ile Tyr Glu Ala Lys Asp Tyr Glu Thr Ser Glu Lys Val Gly Glu Ala
        115                 120                 125

Thr Val Glu Lys Leu Ser Asp Gly Val Glu Ile Ile Val Pro Phe Asp
130                 135                 140

Tyr Ile Glu Thr Pro Glu Asp Phe Tyr Phe Ala Val Ser Thr Val Lys
145                 150                 155                 160

Gly Gly Asn Leu Glu Val Ile Thr Thr Pro Val Glu Leu Arg Leu Pro
                165                 170                 175

Met Glu Val Lys Gly Val Pro Ile Val Asp Ile Thr
            180                 185
```

<210> SEQ ID NO 26
<211> LENGTH: 190
<212> TYPE: PRT
<213> ORGANISM: Thermococcus kodakaraensis
<220> FEATURE:
<221> NAME/KEY: DOMAIN
<222> LOCATION: (1)..(190)
<223> OTHER INFORMATION: X47 domain -continued

```
<400> SEQUENCE: 26

Ser Tyr Leu Tyr Gly Asn Tyr Phe Pro Asp Gly Gln Pro Tyr Ile Thr
1               5                   10                  15

Arg Ala Leu Asp Gly Leu Gly Glu Gly Asp Lys Lys Glu Tyr Ser Ser
            20                  25                  30

Glu Ser Ala Leu Ala Lys Gly Val Glu Val Tyr Phe Glu Gly Asp Gly
        35                  40                  45

Ile His Phe Leu Val Lys Gly Asp Leu Asn Glu Phe Glu Val Ser Leu
    50                  55                  60

Ser Ser Pro Asp Glu Arg Ile Gly Asn Thr Phe Thr Ile Leu Gln Lys
65                  70                  75                  80

Arg Pro Thr Glu Leu Arg Tyr Ser Leu Phe Pro Leu Ser Lys Asp Ser
            85                  90                  95

Val Gly Met Leu Ile Thr Thr His Val Val Tyr Lys Asp Gly Lys Ala
        100                 105                 110

Glu Val Tyr Lys Ala Lys Asp Tyr Glu Thr Ser Glu Lys Val Gly Asp
        115                 120                 125

Val Thr Ala Lys Lys Thr Asp Ala Gly Val Glu Val Val Pro Phe
130                 135                 140

Asp Tyr Leu Ser Asn Pro Ser Asp Phe Tyr Phe Ala Val Ser Thr Val
145                 150                 155                 160

Asn Glu Asn Gly Glu Leu Glu Val Ile Ser Ser Pro Val Glu Leu Lys
            165                 170                 175

Leu Pro Val Gln Val Lys Gly Ala Val Ile Ala Asp Ile Ala
            180                 185                 190

<210> SEQ ID NO 27
<211> LENGTH: 190
<212> TYPE: PRT
<213> ORGANISM: Pyrococcus furiosus
<220> FEATURE:
<221> NAME/KEY: DOMAIN
<222> LOCATION: (1)..(190)
<223> OTHER INFORMATION: X47 domain

<400> SEQUENCE: 27

Ser Tyr Leu Tyr Gly Asn Tyr Phe Pro Asp Gly Ala Pro Tyr Thr Val
1               5                   10                  15

Arg Ala Leu Glu Gly Leu Lys Glu Gly Asp Val Lys Glu Tyr Ser Ser
            20                  25                  30

Leu Ser Pro Val Ala Glu Gly Val Lys Val Phe Phe Asp Ser Gln Gly
        35                  40                  45

Leu His Phe Ile Ile Lys Gly Arg Ile Asp Lys Phe Glu Ile Ser Ile
    50                  55                  60

Tyr Glu Lys Asp Lys Arg Ile Gly Asn Thr Phe Thr Leu Leu Gln Lys
65                  70                  75                  80

Lys Pro Asp Lys Ile Arg Tyr Asp Val Phe Pro Phe Val Arg Asp Ser
            85                  90                  95

Val Gly Leu Met Ile Thr Lys His Ile Val Tyr Lys Asp Gly Lys Ala
        100                 105                 110

Glu Ile Tyr Asn Ala Thr Asp Tyr Glu Gly Tyr Glu Lys Ile Gly Glu
        115                 120                 125

Ala Gln Val Ser Val Asn Gly Asp Glu Ile Glu Val Ile Val Pro Phe
130                 135                 140

Glu Tyr Leu Glu Thr Pro Glu Asp Phe Tyr Phe Ala Val Ser Thr Val
145                 150                 155                 160
```

```
Asp Glu Leu Gly Met Leu Glu Val Ile Thr Thr Pro Val Asn Leu Lys
                165                 170                 175

Leu Pro Val Gln Val Lys Gly Val Val Leu Val Asp Ile Ala
            180                 185                 190

<210> SEQ ID NO 28
<211> LENGTH: 189
<212> TYPE: PRT
<213> ORGANISM: Thermococcus onnurieus
<220> FEATURE:
<221> NAME/KEY: DOMAIN
<222> LOCATION: (1)..(189)
<223> OTHER INFORMATION: X47 domain

<400> SEQUENCE: 28

Gly Tyr Leu Tyr Gly Asn Phe Phe Pro Asp Gly Glu Pro Tyr Thr Val
1               5                   10                  15

Arg Ala Leu Asp Gly Leu Gly Glu Gly Gln Val Lys Asn Tyr Ser Ser
            20                  25                  30

Met Ser Ser Leu Ala Glu Gly Val Ser Val Tyr Phe Asp Gly Asp Gly
        35                  40                  45

Ile His Phe Ile Val Lys Gly Glu Leu Asn Glu Phe Glu Ile Ser Ile
    50                  55                  60

Tyr Glu Lys Gly Glu Arg Val Gly Asn Thr Phe Thr Ile Leu Gln Asp
65                  70                  75                  80

Lys Pro Thr Glu Leu Arg Tyr Ser Met Phe Pro Phe Ser Lys Asp Ser
                85                  90                  95

Val Gly Leu Met Ile Thr Lys His Ile Val Tyr Lys Asp Asn Lys Ala
            100                 105                 110

Glu Val Tyr Gln Ala Thr Asn Tyr Glu Asp Ser Glu Lys Ile Gly Asp
        115                 120                 125

Ala Val Val Lys Thr Val Asn Gly Arg Val Glu Ile Val Pro Phe
    130                 135                 140

Glu Tyr Ile Lys Thr Pro Glu Asp Phe Tyr Phe Ala Val Ser Thr Val
145                 150                 155                 160

Lys Asp Gly Glu Leu Glu Val Ile Thr Thr Pro Ile Glu Leu Lys Leu
                165                 170                 175

Pro Thr Glu Val Lys Gly Val Thr Leu Val Asp Ile Ala
            180                 185

<210> SEQ ID NO 29
<211> LENGTH: 189
<212> TYPE: PRT
<213> ORGANISM: Thermococcus sp.
<220> FEATURE:
<221> NAME/KEY: DOMAIN
<222> LOCATION: (1)..(189)
<223> OTHER INFORMATION: X47 domain

<400> SEQUENCE: 29

Ser Tyr Leu Phe Gly Asn Tyr Phe Pro Asp Gly Glu Pro Tyr Val Thr
1               5                   10                  15

Arg Ala Leu Asp Gly Leu Lys Glu Gly Glu Met Lys Asn Tyr Ser Ser
            20                  25                  30

Met Ser Pro Leu Ala Glu Gly Val Ser Val Tyr Phe Asp Gly Glu Gly
        35                  40                  45

Leu His Phe Ile Val Arg Gly Asn Leu Ser Gln Phe Glu Val Ser Ile
    50                  55                  60

Trp Glu Lys Asp Glu Arg Val Gly Asn Thr Phe Thr Leu Leu Gln Gly
65                  70                  75                  80
```

```
Arg Pro Gly Glu Leu Arg Tyr Ser Met Phe Pro Phe Ser Ala Asp Ser
                85                  90                  95

Val Gly Leu Met Ile Thr Lys His Leu Val Tyr His Asp Gly Lys Ala
            100                 105                 110

Glu Val Tyr Lys Ala Thr Asp Tyr Glu Asn Ser Glu Lys Leu Gly Glu
        115                 120                 125

Ala Thr Val Arg Glu Thr Ser Glu Gly Ile Glu Val Val Pro Phe
130                 135                 140

Glu Tyr Ile Glu Asn Pro Ala Asp Phe Tyr Phe Ala Val Ser Thr Val
145                 150                 155                 160

Lys Asp Gly Arg Leu Glu Val Ile Ser Thr Pro Val Glu Leu Lys Leu
                165                 170                 175

Pro Thr Glu Val Lys Gly Val Val Ile Ala Asp Ile Ala
            180                 185

<210> SEQ ID NO 30
<211> LENGTH: 189
<212> TYPE: PRT
<213> ORGANISM: Thermococcus litoralis
<220> FEATURE:
<221> NAME/KEY: DOMAIN
<222> LOCATION: (1)..(189)
<223> OTHER INFORMATION: X47 domain

<400> SEQUENCE: 30

Ser Tyr Leu Phe Gly Asn Tyr Phe Pro Asn Gly Glu Pro Tyr Ala Ile
1               5                   10                  15

Arg Glu Leu Thr Gly Leu Pro Glu Gly Glu Lys Lys Ser Trp Ser Ser
                20                  25                  30

Leu Ser Pro Ile Ala Glu Gly Val Glu Leu Tyr Phe Asp Glu Gln Gly
            35                  40                  45

Leu His Phe Val Val Lys Thr Thr Lys Glu Phe Glu Ile Ser Ile Phe
        50                  55                  60

Glu Pro Gly Lys Val Met Gly Asn Thr Phe Thr Leu Leu Gln Thr Lys
65                  70                  75                  80

Pro Ser Glu Leu Arg Tyr Asp Ile Phe Pro Phe Ser Lys Asp Ser Val
                85                  90                  95

Gly Leu Met Ile Thr Lys His Ile Ile Val Lys Glu Gly Lys Ala Glu
            100                 105                 110

Val Tyr Lys Ala Thr Asp Tyr Glu Asn Ser Glu Lys Val Gly Glu Val
        115                 120                 125

Asp Val Lys Glu Thr Asp Gly Gly Val Glu Val Ile Val Pro Phe Asp
130                 135                 140

Tyr Leu Asp Ser Pro Ser Asp Phe Tyr Phe Ala Val Ser Thr Val Asn
145                 150                 155                 160

Asp Gln Gly Glu Leu Glu Ile Ile Thr Asn Pro Ile Glu Val Lys Leu
                165                 170                 175

Pro Lys Gln Val Glu Gly Ile Val Val Ala Glu Ile Lys
            180                 185

<210> SEQ ID NO 31
<211> LENGTH: 47
<212> TYPE: DNA
<213> ORGANISM: Artificial Sequence
<220> FEATURE:
<223> OTHER INFORMATION: Synthetic construct

<400> SEQUENCE: 31
```

```
gccaaggccg gttttttatg ttttacttaa ggattacgcg agcattg                    47
```

<210> SEQ ID NO 32
<211> LENGTH: 37
<212> TYPE: DNA
<213> ORGANISM: Artificial Sequence
<220> FEATURE:
<223> OTHER INFORMATION: Synthetic construct

<400> SEQUENCE: 32

```
tgattaacgc gtttaagtat agttgccagg gccatgg                               37
```

<210> SEQ ID NO 33
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(29)
<223> OTHER INFORMATION: Synthetic Construct

<400> SEQUENCE: 33

```
tgattaacgc gtttaaggag gctcaacgc                                        29
```

<210> SEQ ID NO 34
<211> LENGTH: 809
<212> TYPE: PRT
<213> ORGANISM: Artificial Sequence
<220> FEATURE:
<223> OTHER INFORMATION: Hybrid protein
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)
<223> OTHER INFORMATION: Hybrid pullulanase of Thermoccus hydrothermalis
      and Thermococcus litoralis

<400> SEQUENCE: 34

Met Lys Lys Pro Leu Gly Lys Ile Val Ala Ser Thr Ala Leu Leu Ile
    -25                 -20                 -15

Ser Val Ala Phe Ser Ser Ser Ile Ala Ser Ala Glu Glu Pro Lys Pro
    -10                  -5                  -1   1               5

Leu Asn Val Ile Ile Val Trp His Gln His Gln Pro Tyr Tyr Tyr Asp
                10                  15                  20

Pro Ile Gln Asp Ile Tyr Thr Arg Pro Trp Val Arg Leu His Ala Ala
            25                  30                  35

Asn Asn Tyr Trp Lys Met Ala Asn Tyr Leu Ser Lys Tyr Pro Asp Val
        40                  45                  50

His Val Ala Ile Asp Leu Ser Gly Ser Leu Ile Ala Gln Leu Ala Asp
    55                  60                  65

Tyr Met Asn Gly Lys Lys Asp Thr Tyr Gln Ile Val Thr Glu Lys Ile
70                  75                  80                  85

Ala Asn Gly Glu Pro Leu Thr Leu Glu Asp Lys Trp Phe Met Leu Gln
                90                  95                  100

Ala Pro Gly Gly Phe Phe Asp His Thr Ile Pro Trp Asn Gly Glu Pro
            105                 110                 115

Val Ala Asp Glu Asn Gly Asn Pro Tyr Arg Glu Gln Trp Asp Arg Tyr
        120                 125                 130

Ala Glu Leu Lys Asp Lys Arg Asn Asn Ala Phe Lys Lys Tyr Ala Asn
    135                 140                 145

```
Leu Pro Leu Asn Glu Gln Lys Val Lys Ile Thr Ala Glu Phe Thr Glu
150                 155                 160                 165

Gln Asp Tyr Ile Asp Leu Ala Val Leu Phe Asn Leu Ala Trp Ile Asp
                170                 175                 180

Tyr Asn Tyr Ile Ile Asn Thr Pro Glu Leu Lys Ala Leu Tyr Asp Lys
                185                 190                 195

Val Asp Val Gly Gly Tyr Thr Lys Glu Asp Val Ala Thr Val Leu Lys
                200                 205                 210

His Gln Met Trp Leu Leu Asn His Thr Phe Glu Glu His Glu Lys Ile
                215                 220                 225

Asn Tyr Leu Leu Gly Asn Gly Asn Val Glu Val Thr Val Val Pro Tyr
230                 235                 240                 245

Ala His Pro Ile Gly Pro Leu Leu Asn Asp Phe Gly Trp Tyr Glu Asp
                250                 255                 260

Phe Asp Ala His Val Lys Lys Ala His Glu Leu Tyr Lys Lys Tyr Leu
                265                 270                 275

Gly Asp Asn Arg Val Glu Pro Gln Gly Gly Trp Ala Ala Glu Ser Ala
                280                 285                 290

Leu Asn Asp Lys Thr Leu Glu Ile Leu Thr Asn Asn Gly Trp Lys Trp
295                 300                 305

Val Met Thr Asp Gln Met Val Leu Asp Ile Leu Gly Ile Pro Asn Thr
310                 315                 320                 325

Val Glu Asn Tyr Tyr Lys Pro Trp Val Ala Glu Phe Asn Gly Lys Lys
                330                 335                 340

Ile Tyr Leu Phe Pro Arg Asn His Asp Leu Ser Asp Arg Val Gly Phe
                345                 350                 355

Arg Tyr Ser Gly Met Asn Gln Tyr Gln Ala Val Glu Asp Phe Val Asn
                360                 365                 370

Glu Leu Leu Lys Val Gln Lys Glu Asn Tyr Asp Gly Ser Leu Val Tyr
                375                 380                 385

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
                425                 430                 435

Tyr Gly Asp Lys Ala Asn Lys Leu Thr Pro Arg Met Met Glu Arg Leu
                440                 445                 450

Asp Leu Thr Gly Asp Asn Val Asn Ala Leu Leu Lys Ala Gln Ser Leu
                455                 460                 465

Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
                505                 510                 515

Met Glu Asn Lys Asp Lys Met Ser Gln Ala Asp Trp Glu Lys Ala Tyr
                520                 525                 530

Glu Tyr Leu Leu Arg Ala Glu Ala Ser Asp Trp Phe Trp Trp Tyr Gly
                535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
```

| | | 570 | | | | 575 | | | | 580 | | |
|---|---|---|---|---|---|---|---|---|---|---|---|---|

Tyr Leu Phe Gly Asn Tyr Phe Pro Asp Gly Glu Pro Tyr Thr Thr Arg
                585                 590                 595

Gly Leu Val Gly Leu Lys Asp Gly Glu Met Lys Asn Phe Ser Ser Met
            600                 605                 610

Ser Pro Leu Ala Lys Gly Val Ser Val Tyr Phe Asp Gly Glu Gly Ile
        615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
        680                 685                 690

Ile Tyr Gly Ala Thr Asp Tyr Glu Lys Ser Glu Lys Leu Gly Glu Ala
    695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
        760                 765                 770

Asp Asp His Gly Pro Gly Asn Tyr Thr
775                 780

<210> SEQ ID NO 35
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(43)
<223> OTHER INFORMATION: C1QBX46-F Primer

<400> SEQUENCE: 35 agggggtatct ctcgagaaaa gaccatccta cttgttcgga aac           43

<210> SEQ ID NO 36
<211> LENGTH: 37
<212> TYPE: DNA
<213> ORGANISM: Artificial Sequence
<220> FEATURE:
<223> OTHER INFORMATION: Synthetic Construct

<400> SEQUENCE: 36
ggtgctgatg gaattcgatg tcggcgataa caacacc                   37

<210> SEQ ID NO 37
<211> LENGTH: 867
<212> TYPE: DNA
<213> ORGANISM: Thermococcus hydrothermalis
<220> FEATURE:
<221> NAME/KEY: misc_signal
<222> LOCATION: (1)..(255)
<220> FEATURE:
<221> NAME/KEY: CDS
<222> LOCATION: (1)..(867)

-continued

```
<220> FEATURE:
<221> NAME/KEY: misc_feature
<222> LOCATION: (256)..(822)
<223> OTHER INFORMATION: X47 Domain
<220> FEATURE:
<221> NAME/KEY: misc_feature
<222> LOCATION: (829)..(864)
<223> OTHER INFORMATION: Histidine affinity tag for purification

<400> SEQUENCE: 37 atg aga ttt cct tca att ttt act gca gtt tta ttc gca gca tcc tcc     48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa     96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc    144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg    192
Asp Val Ala Val Leu Pro Phe Ser Asn Ser Thr Asn Asn Gly Leu Leu
50                  55                  60 ttt ata aat act act att gcc agc att gct gct aaa gaa gaa ggg gta    240
Phe Ile Asn Thr Thr Ile Ala Ser Ile Ala Ala Lys Glu Glu Gly Val
65                  70                  75                  80 tct ctc gag aaa aga cca tcc tac ttg ttc gga aac tac ttc cca gac    288
Ser Leu Glu Lys Arg Pro Ser Tyr Leu Phe Gly Asn Tyr Phe Pro Asp
                85                  90                  95 gga gag cct tac aca act aga ggt ttg gtt ggt ttg aag gac gga gag    336
Gly Glu Pro Tyr Thr Thr Arg Gly Leu Val Gly Leu Lys Asp Gly Glu
            100                 105                 110 atg aag aac ttc tcc agt atg tca cca ttg gcc aag ggt gtc tct gtc    384
Met Lys Asn Phe Ser Ser Met Ser Pro Leu Ala Lys Gly Val Ser Val
        115                 120                 125 tac ttc gac ggt gag ggt atc cat ttc atc gtt aag gga aac ttg gac    432
Tyr Phe Asp Gly Glu Gly Ile His Phe Ile Val Lys Gly Asn Leu Asp
    130                 135                 140 aga ttc gag gtc tca atc tgg gag aag gac gag aga gtt ggt aac act    480
Arg Phe Glu Val Ser Ile Trp Glu Lys Asp Glu Arg Val Gly Asn Thr
145                 150                 155                 160 ttc act aga ttg cag gag aag cca gac gag ttg tct tac ttc atg ttc    528
Phe Thr Arg Leu Gln Glu Lys Pro Asp Glu Leu Ser Tyr Phe Met Phe
                165                 170                 175 cct ttc tcc aga gac tct gtt ggt ttg ttg atc aca aag cat gtt gtt    576
Pro Phe Ser Arg Asp Ser Val Gly Leu Leu Ile Thr Lys His Val Val
            180                 185                 190 tac gag aac ggt aag gcc gag atc tac ggt gct acc gac tac gag aag    624
Tyr Glu Asn Gly Lys Ala Glu Ile Tyr Gly Ala Thr Asp Tyr Glu Lys
        195                 200                 205 tcc gag aag ttg gga gag gcc act gtc aag aac act agt gag gga atc    672
Ser Glu Lys Leu Gly Glu Ala Thr Val Lys Asn Thr Ser Glu Gly Ile
    210                 215                 220 gag gtc gtc ttg cct ttc gac tac atc gag aac cca tcc gac ttc tac    720
Glu Val Val Leu Pro Phe Asp Tyr Ile Glu Asn Pro Ser Asp Phe Tyr
225                 230                 235                 240 ttc gcc gtt tcc acc gtc aag gac ggt gac ttg gag gtt atc tcc aca    768
Phe Ala Val Ser Thr Val Lys Asp Gly Asp Leu Glu Val Ile Ser Thr
                245                 250                 255 cct gtt gag ttg aag ttg cct acc gag gtc aag ggt gtt gtt atc gcc    816
Pro Val Glu Leu Lys Leu Pro Thr Glu Val Lys Gly Val Val Ile Ala
            260                 265                 270 gac atc gaa ttc cat cag cac caa cat caa cac caa cat cag cac cca    864
```

-continued

```
Asp Ile Glu Phe His Gln His Gln His Gln His Gln His Pro
            275                 280                 285
taa                                                                    867

<210> SEQ ID NO 38
<211> LENGTH: 288
<212> TYPE: PRT
<213> ORGANISM: Thermococcus hydrothermalis

<400> SEQUENCE: 38

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Pro Ser Tyr Leu Phe Gly Asn Tyr Phe Pro Asp
                85                  90                  95

Gly Glu Pro Tyr Thr Thr Arg Gly Leu Val Gly Leu Lys Asp Gly Glu
            100                 105                 110

Met Lys Asn Phe Ser Ser Met Ser Pro Leu Ala Lys Gly Val Ser Val
            115                 120                 125

Tyr Phe Asp Gly Glu Gly Ile His Phe Ile Val Lys Gly Asn Leu Asp
    130                 135                 140

Arg Phe Glu Val Ser Ile Trp Glu Lys Asp Glu Arg Val Gly Asn Thr
145                 150                 155                 160

Phe Thr Arg Leu Gln Glu Lys Pro Asp Glu Leu Ser Tyr Phe Met Phe
                165                 170                 175

Pro Phe Ser Arg Asp Ser Val Gly Leu Leu Ile Thr Lys His Val Val
            180                 185                 190

Tyr Glu Asn Gly Lys Ala Glu Ile Tyr Gly Ala Thr Asp Tyr Glu Lys
        195                 200                 205

Ser Glu Lys Leu Gly Glu Ala Thr Val Lys Asn Thr Ser Glu Gly Ile
    210                 215                 220

Glu Val Val Leu Pro Phe Asp Tyr Ile Glu Asn Pro Ser Asp Phe Tyr
225                 230                 235                 240

Phe Ala Val Ser Thr Val Lys Asp Gly Asp Leu Glu Val Ile Ser Thr
                245                 250                 255

Pro Val Glu Leu Lys Leu Pro Thr Glu Val Lys Gly Val Val Ile Ala
            260                 265                 270

Asp Ile Glu Phe His Gln His Gln His Gln His Gln His Pro
    275                 280                 285
```

PULLULANASE VARIANTS AND USES THEREOF

CROSS-REFERENCE TO RELATED APPLICATIONS

This application is a 35 U.S.C. 371 national application of PCT/US2010/061761 filed Dec. 22, 2010, which claims priority or the benefit under 35 U.S.C. 119 of U.S. provisional application No. 61/289,040 filed Dec. 22, 2009, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to pullulanase variant having pullulanase activity and isolated polynucleotides encoding said pullulanase variants. The invention also relates to nucleic acid constructs, vectors, and host cells comprising the polynucleotides as well as methods of producing and using the polypeptides. The invention also relates to the use of said pullulanase variants for starch convention processes include processes for producing a fermentation product, such as especially ethanol.

BACKGROUND OF THE INVENTION

A pullulanase is an enzyme which can degrade alpha-(1,6)-linkage of pullulan, amylopectin and other branched substrates. In the grain industry, bacterial pullulanases have been used for the purpose of removing alpha-1,6 bonds in starch, which may cause undesirable panose formation in the saccharification process.

Two different classes of pullulanases are known: EC 3.2.1.41 which include two types (type I and II) of pullulanases and EC 3.2.1.135 referred to as "neopullulanases".

WO 95/23852 discloses an amylopullulanase from *Thermococcus celer* and the use for producing 5 sweeteners and ethanol from starch.

A pullulanase type II (family GH57) from the hyperthermophile *Thermococcus hydrothermalis* is disclosed as UNIPROT: Q9Y8I8.

A pullulanase type II (family GH57) from *Thermococcus litoralis* is disclosed in UNIPROT: Q8NKS8.

WO 98/26058 concerns a pullulanase from *Thermococcus hydrothermalis* CNCM 1 having a temperature optimum of 110° C. at pH 5.5 and the use thereof in combination with an alpha-amylase and alpha-glucosidase for producing syrups.

The object of the present invention is to provide pullulanases expressed in increased yields and/or having higher thermostability, respectively, compared to a parent pullulanase in question.

SUMMARY OF THE INVENTION

The present invention provides pullulanase variants of parent pullulanases belonging to family GH57 pullulanases.

In the first aspect the invention relates to pullulanase variants of parent pullulanases belonging to family GH57 and comprises an X47 domain, wherein the pullulanase variant is truncated at a position after the X47 domain.

In a preferred embodiment the parent family GH57 pullulanase may be derived from any bacterium. In a preferred embodiment the parent pullulanase is derived from a strain of the genus *Thermococcus*, preferably a strain of *Thermococcus hydrothermalis*, especially the mature part of SEQ ID NO: 2, or a strain of *Thermococcus litoralis*, especially the mature part of SEQ ID NO: 4 herein or the parent pullulanase is a hybrid pullulanase, e.g., comprising a sequence from *Thermococcus hydrothermalis* pullulanase and a sequence from *Thermococcus litoralis* pullulanase. Examples of parent pullulanases can be found below in the "Parent Pullulanases"-section.

More specifically the invention relates to pullulanase variants prepared from parent pullulanases belonging to family GH57 which comprises an X47 domain, wherein the parent pullulanase is the one shown in SEQ ID NO: 2 or 4 or 34, or another parent pullulanase having at least 60% identity to SEQ ID NOs: 2, 4 or 34, wherein the pullulanase variant comprises or consists of:

a) an amino acid sequence having pullulanase activity
  i) having at least 60% identity to the sequence from amino acids 1-1009 of SEQ ID NO: 2, preferably to the sequence from amino acids 1-782 of SEQ ID NO: 2; or
  ii) having at least 60% identity to the sequence from amino acids 1-988 of SEQ ID NO: 4, preferably to the sequence from amino acids 1-781 of SEQ ID NO: 4;
  iii) having at least 60% identity to the sequence from amino acids 1-782 of SEQ ID NO: 34;
b) the parent pullulanase of SEQ ID NOs: 2, 4 or 34 is truncated at a position after the X47 domain;
c) another parent pullulanase having at least 60% identity to SEQ ID NOs: 2, 4 or 34 truncated in a position corresponding to the ones defined in a) or b);
d) a pullulanase variant defined in a), b) or c) having one or more (several) amino acids substituted, deleted, and/or inserted.

In another aspect the invention relates to an isolated polynucleotide encoding a pullulanase variant of the invention or an X47 domain of the invention selected from the group consisting of:

i) a polynucleotide having at least 60%, preferably at least 70%, more preferably at least 80%, more preferably at least 90%, more preferably at least 95%, at least 96%, preferably at least 97%, preferably at least 98%, preferably at least 99% identity with the pullulanase variant coding part of SEQ ID NOS: 1 or 3, or a complementary strand thereof;

ii) a polynucleotide having at least 60%, preferably at least 70%, more preferably at least 80%, more preferably at least 90%, more preferably at least 95%, at least 96%, preferably at least 97%, preferably at least 98%, preferably at least 99% identity with the X47 domain coding part of sequence SEQ ID NO: 1, 3, 37, or a complementary strand thereof; and iii) a polynucleotide which hybridizes under medium stringency, preferably high stringency conditions with the pullulanase variant or X47 domain coding part of SEQ ID NO: 1, 3, or 37, or a complementary strand thereof.

The invention also relates to recombinant expression vectors comprising the nucleic acid construct of the invention and recombinant host cells comprising the nucleic acid construct of the invention or the vector of the invention.

In another aspect the invention relates to processes for producing a fermentation product from starch-containing material comprising the steps of:

(a) liquefying starch-containing material in the presence of an alpha-amylase and a family GH57 pullulanase;
(b) saccharifying the liquefied material obtained in step (a) using a carbohydrate-source generating enzyme;

(c) fermenting using a fermenting organism.

In a preferred embodiment the family GH57 pullulanase is a pullulanase variant of the invention.

In a further aspect the invention relates to the use of a family GH57 pullulanase or variants of the invention in a process of producing sweeteners from starch.

The invention also relates to the use of a family GH57 pullulanases or pullulanase variants of the invention in a process of producing a fermentation product, such as ethanol, from gelatinized and/or un-gelatinized starch.

DETAILED DESCRIPTION OF THE INVENTION

Figure 1:
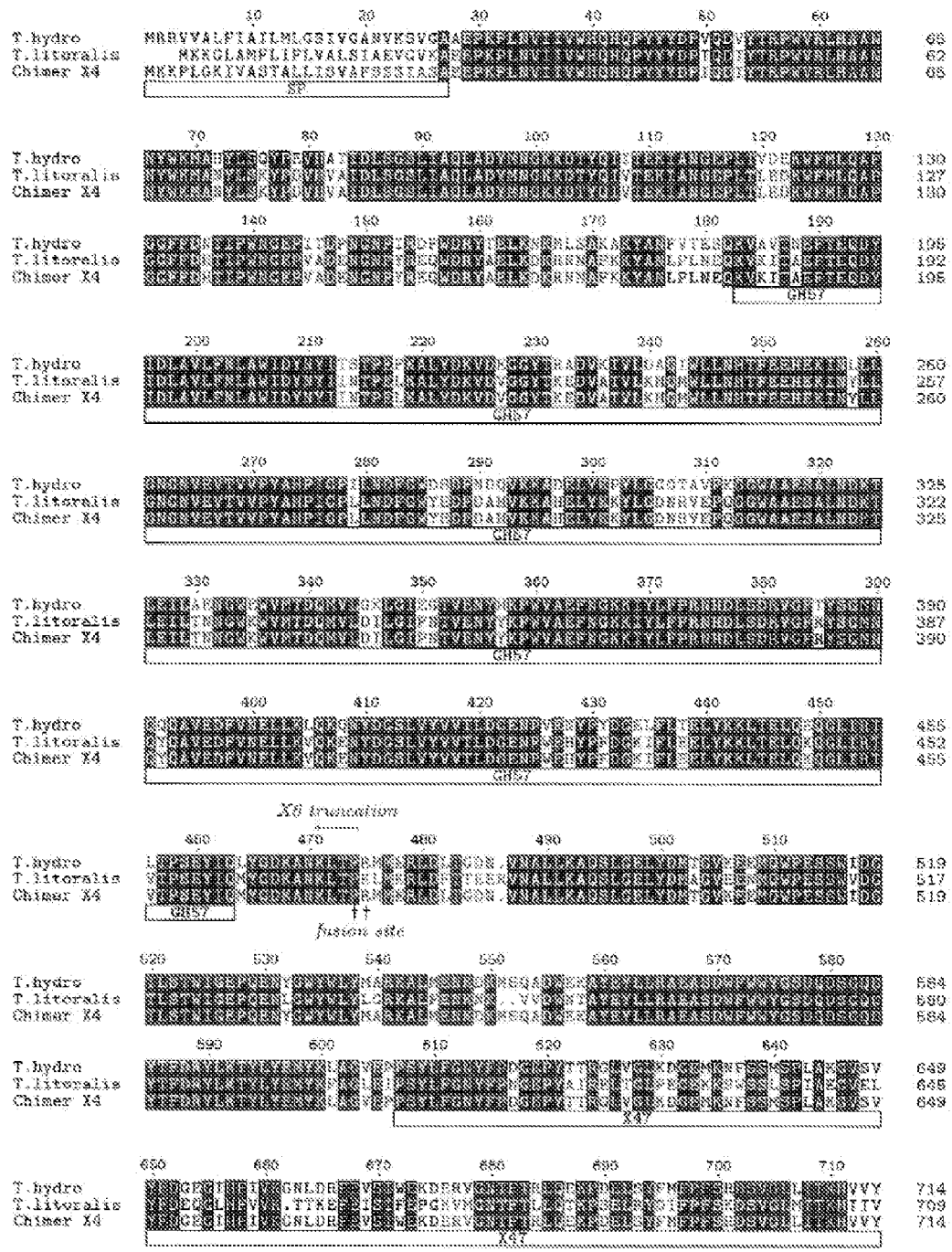
FIG. 1 shows an alignment of the mature part of the parent pullulanases from *Thermococcus hydrothermalis* (UNIPROT: Q9Y8I8) and *Thermococcus litoralis* (UNIPROT: Q8NKS8). Domains are annotated after CAZy (eFAM), GH57 (catalytic pullulanase domain), X47, DUF2223a and DUF2223b domains and linker (putative cell wall binding). Truncations X1, X4, X5 and X6 are indicated with left headed arrow.

The inventors have prepared pullulanase variants of parent pullulanases belonging to family GH57 (Glycoside Hydrolase Family 57) comprising an X47 domain. A collection of GH57 pullulanases are described in Zone et al., 2004, *Eur. J. Biochem.* 271: 2863-2872 (incorporated by reference). However, in context of the invention GH57 pullulanases are not limited to those described in there. Generally Family GH57 is defined and updated by the CAZy-team and can be found on the CAZy-server (see cazy.org).

A parent pullulanase according to the invention belongs to family GH57 and is, preferably a pullulanase type II classified under EC 3.2.1.41. The specific parent pullulanases (UNIPROT: Q9Y8I8) and UNIPROT: Q8NKS8 used by the inventors are derived from strains of the hyperthermophile bacteria *Thermococcus hydrothermalis* and *Thermococcus litoralis*, respectively and hybrids thereof Several pullulanase variants were expressed in *Bacillus subtilis* and *Pichia pastoria* in several C-terminal truncated forms. For instance, a pullulanase variant truncated just after the X47 domain (truncation between 782 and 783 in SEQ ID NO: 2) showed a significant increased expression level and at the same time maintained pullulanase activity compared to the parent pullulanase.

Pullulanase Activity: Pullulanase activity means the ability to hydrolyze glycosidic alpha-(1,6)-linkages. It may be determined with pullulan or amylopectin as substrate, e.g., by the NPUN assay described below in the "Materials & Methods"-section or the AZCL-pullulan plates assay described in Example 4.

Variant: The term "variant" is defined herein as a polypeptide having pullulanase activity comprising an alteration, such as a substitution, insertion, deletion, truncation, of one or more (several) amino acid residues at one or more (several) specific positions of the mature parent pullulanase, e.g., of SEQ ID NO: 2, 4 or 34. The altered polynucleotide is obtained through human intervention by modification of the polynucleotide sequence disclosed, e.g., in SEQ ID NO: 1 or 3; or a homologous sequence thereof.

The pullulanase variant of the present invention may have at least 20%, at least 40%, at least 50%, at least 60%, at least 70%, least 80%, at least 90%, at least 95%, or at least 100% of the pullulanase activity of the mature parent pullulanase, such as the parent pullulanase shown in SEQ ID NOS: 2, 4, or 34.

Wild-Type Enzyme: The term "wild-type" pullulanase denotes a pullulanase expressed by a naturally occurring microorganism, such as a bacterium, yeast, or filamentous fungus found in nature.

Parent Enzyme: The term "parent" pullulanase as used herein means a pullulanase to which a modification, e.g., substitution(s), insertion(s), deletion(s), and/or truncation(s), is made to produce the pullulanase variants of the present invention. This term also refers to the pullulanase with which a variant is compared and aligned. The parent may be a naturally occurring (wild-type) pullulanase or a variant. For instance, the parent pullulanase may be a variant of a naturally occurring pullulanase which has been modified or altered in the amino acid sequence. A parent may also be an allelic variant, which is a pullulanase encoded by any of two or more alternative forms of a gene occupying the same chromosomal locus.

Isolated variant or polypeptide: The term "isolated variant" or "isolated pullulanase" as used herein refers to a variant or a pullulanase that is isolated from a source. In one aspect, the pullulanase variant or pullulanase is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure variant or polypeptide: The term "substantially pure variant" or "substantially pure pullulanase" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure variant or polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The variants and polypeptides of the present invention are preferably in a substantially pure form. This can be accomplished, for example, by preparing the variant or polypeptide by well-known recombinant methods or by classical purification methods.

Mature polypeptide: The term "mature pullulanase" is defined herein as a polypeptide having pullulanase activity that is in its final form following translation and any post-translational modifications, such as N-terminal processing, C-terminal truncation, glycosylation, phosphorylation, etc. In one preferred embodiment, the mature pullulanase is amino acids 1 to 1310 of SEQ ID NO: 2 and amino acids 1-1065 for SEQ ID NO: 4. Amino acids −1 to −27 of SEQ ID NO: 2 and amino acids −1 to −24 of SEQ ID NO: 4 are signal peptides.

Mature polypeptide coding sequence: The term "mature polypeptide coding sequence" is defined herein as a nucleotide sequence that encodes a mature pullulanase. In one embodiment, the mature pullulanase coding sequence is nucleotides 82 to 4011 of SEQ ID NO: 1 and nucleotide 73-3267 of SEQ ID NO: 3. Nucleotides 1 to 81 of SEQ ID NO: 1 and nucleotides 1-72 of SEQ ID NO: 3 encode signal peptides.

Alignment: Alignment of two amino acid sequence in order to identify corresponding position is according to the invention done by using the MUSCLE (Multiple Sequence Comparison by Log-Expectation) alignment program (Edgar, Robert C. (2004), MUSCLE: multiple sequence alignment with high accuracy and high throughput, *Nucleic Acids Research* 32(5), 1792-97.) with 16 iterations of the protein sequence alignments.

Identity: The relatedness between two amino acid sequences or between two nucleotide sequences is described by the parameter "identity". For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In one aspect, the isolated polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered polypeptide production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Nucleic acid construct: The term "nucleic acid construct" as used herein refers to a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Hybridization: The polynucleotide may be able to hybridize with the mature polypeptide coding sequence of SEQ ID NOs: 1 or 3 or any other polynucleotide encoding a mature family GH57 pullulanase. The hybridization may be done by prehybridization and hybridization at 42° C. in 5×SSPE, 0.3% SDS, 200 μg/ml sheared and denatured salmon sperm DNA, and either 25% formamide (for very low and low stringencies), 35% formamide (for medium and medium-high stringencies), or 50% formamide (for high and very high stringencies), following standard Southern blotting procedures for 12 to 24 hours optimally. The carrier material is finally washed three times each for 15 minutes using 2×SSC, 0.2% SDS preferably at 45° C. (very low stringency), 50° C. (low stringency), 55° C. (medium stringency), 60° C. (medium-high stringency), 65° C. (high stringency), or 70° C. (very high stringency).

Parent Pullulanases

Parent pullulanases according to the invention are family GH57 pullulanases which having an X47 domain. The pullulanases are classified under EC 3.2.1.41 and are referred to as pullulanase type II or sometimes "amylopullulanases". Type II pullulanases are in contrast to type I pullulanases, which specifically attack alpha-1,6 linkages, also able to hydrolyze alpha-1,4 linkages.

In a preferred embodiment the parent pullulanase belongs to family GH57 and comprises an X47 domain and optional DUF2223a and/or DUF2223b domains. Domains and families can be found in the Pfam protein families database: Finn et al., 2008, *Nucleic Acids Research* Database Issue 36: D281-D288. The Pfam database is a collection of protein families, each represented by multiple sequence alignments and Hidden Markov Models (HMMs). The parent family GH57 pullulanase may be obtained from any source, such as a microorganism, preferably a bacterium or fungal organism, such as yeast and a filamentous fungus. In a preferred embodiment the parent pullulanase is a wild-type enzyme. In a preferred embodiment the parent pullulanase is derived from a bacterium, preferably of the genus *Thermococcus* or *Pyrococcus*, including the ones in the table below.

| | |
|---|---|
| *Thermococcus hydrothermalis.* | SWISSPROT: Q9Y8I8 |
| *Thermococcus* sp. HJ21. | SWISSPROT: B6SED6 |
| *Thermococcus onnurineus* (strain NA1). | SWISSPROT: B6YV54 |
| *Thermococcus kodakaraensis.* | SWISSPROT: Q5JJ55 |
| *Thermococcus* sp. AM4. | SWISSPROT: B7QZQ4 |
| *Pyrococcus furiosus.* | SWISSPROT: Q8TZQ1 |
| *Pyrococcus furiosus* DSM 3638. | SWISSPROT: Q3HUR3 |
| *Pyrococcus furiosus.* | SWISSPROT: O30772 |
| *Thermococcus gammatolerans* (strain DSM 15229/JCM 11827/EJ3). | SWISSPROT: C5A4E3 |
| *Thermococcus barophilus* MP. | SWISSPROT: B5IRL5 |
| *Thermococcus litoralis.* | SWISSPROT: Q8NKS8 |
| *Pyrococcus abyssi.* | SWISSPROT: Q9V294 |

In a preferred embodiment the parent pullulanase is derived from a strain from the genus *Thermococcus* or *Pyrococcus*, including *Thermococcus litoralis*, preferably the mature part of SEQ ID NO: 4 or *Thermococcus hydrothermalis*, preferably the mature part of SEQ ID NO: 2. A parent pullulanase may also be a hybrid (chimeric) enzyme, preferably between bacterial pullulanases, especially the catalytic domain from one pullulanase and the X47 domain from another pullulanase. In a preferred embodiment the parent pullulanase comprises two *Thermococcus pullulanases*, preferably the catalytic domain of *Thermococcus hydrothermalis* and the X47 domain of *Thermococcus litoralis*, especially the chimeric pullulanase shown in SEQ ID NO: 34. The parent pullulanase may have at least 85%, preferably at least 90%, at least 95%, at least 96%, at least 97%, at least 98%, at least 99% identity to the mature parent pullulanase of above mentioned pullulanase, preferably the mature part of the parent pullulanases shown in SEQ ID NO: 2, 4 or 34. The total number of different amino acids in the parent pullulanase shown in SEQ ID NO: 2, 4 or 34, or another parent pullulanase may be fifteen, more preferably fourteen, even more preferably thirteen, even more preferably twelve, even more preferably eleven, even more preferably ten, even more preferably nine, even more preferably eight, even more preferably seven, even more preferably six, even more preferably five, even more preferably four, even more preferably three, even more preferably two, and most preferably one.

The parent pullulanase is encoded by a nucleic acid sequence which may hybridize under medium, more preferably high stringency conditions, with the nucleic acid sequence of SEQ ID NO: 1 or 3, or its complementary strand.

Family GH57 Enzymes and GH57 Domains

Family GH57 enzymes, including Family GH57 pullulanases (EC 3.2.1.41), are defined by the CAZy-team headed by Bernard Henrissat (Architecture et Fonction des Macromolécules Biologiques UMR6098, CNRS/Université de Provence/Université de la Méditerranée, Parc Scientifique et Technologique de Luminy Case 932 163 Avenue de Luminy 13288 Marseille Cedex 09, France). An updated list of sequences belonging to the family GH57 can be found on the CAZy-server (cazy.org). Zone et al., 2004, *Eur. J. Biochem.* 271: 2863-2872 (incorporated by reference) collected 59 amino acid sequence belonging to family GH57 GH57 domains) from glycoside hydrolases using the CAZy server, Pfam database and BLAST tools including the *Thermococcus hydrothermalis* pullulanase sequence (Q9Y8I18_THEHY) and the *Thermococcus litoralis* pullulanase sequence (Q8NKS8). These family GH57 proteins/domains are incorporated by reference. Previous work by Erra-Pujada et al.

("The type II pullulanase of *Thermococcus hydrothermalis*: molecular characterization of the gene and expression of the catalytic domain". *J Bacteriology* 181(10): 3284-3287 (1999)) lead to the GH57 domain prediction as being the catalytic core of the enzyme. According to the invention the parent pullulanase belongs to the family GH57 (Glycoside Hydrolase Family 57). Examples of GH57 domains include the amino acid sequence from 156-436 of SEQ ID NO: 2, amino acid sequence 156-436 of SEQ ID NO: 4 and amino acid sequence 156-436 of SEQ ID NO: 34 (see also FIG. 1). The GH57 domain is located N-terminal to the X47 domain in the parent pullulanase. In an embodiment of the invention the family GH57 pullulanase comprises a GH57 domain and an X47 domain. The GH57 domain may be a domain having at least 60% identity, preferably at least 70%, preferably at least 80%, more preferably at least 85%, more preferably at least 90%, more preferably at least 95%, more preferably at least 96%, more preferably at least 97%, more preferably at least 98%, more preferably at least 99% identity to the amino acid sequences from 156-436 of SEQ ID NO: 2, amino acid sequence 156-436 of SEQ ID NO: 4, or amino acid sequence 156-436 of SEQ ID NO: 34.

X47 Domains

An X47 domain is a domain found downstream from the GH57 domain in a family GH57 pullulanase as defined above. X47 domain may be identified using a Hidden Markov Model (HMM). Examples of X47 domains are shown in SEQ ID NOs: 20-30. In an embodiment the X47 domain is a domain having at least 60% identity, preferably at least 70%, preferably at least 80%, more preferably at least 85%, more preferably at least 90%, more preferably at least 95%, more preferably at least 96%, more preferably at least 97%, more preferably at least 98%, more preferably at least 99% identity to the amino acid sequence from 580-768 of SEQ ID NO: 2 or the amino acid sequence 579-767 of SEQ ID NO: 4, or amino acids 86-274 in SEQ ID NO: 38, or to any of SEQ ID NOs: 20-30.

DUF2223a and DUF2223b Domains

As mentioned above the parent pullulanase may comprise DUF2223 domains which have no known function. The DUF2223a and DUF2223b domains are located C-terminal to the X47 domain (see FIG. 1). The DUF2223 members, as of release 24, 13. Oct. 2009, are found in various prokaryotic membrane-anchored proteins predicted to be involved in the regulation of pullulanases (pfam.sanger.ac.uk/family/DUF2223).

Pullulanase Variants of the Invention

In the first aspect the invention relates to a pullulanase variant of a parent pullulanase belonging to family GH57 (comprising a GH57 domain) comprising an X47 domain, wherein the pullulanase is truncated after the X47 domain. Examples of GH57 domains and X47 domains are mentioned above. The variant may be truncated after the X47 domain or just before the end of the X47 domain (such as 1-10 amino acids), i.e., in the X47 domain. However, it is preferred to truncate after the X47 domain. Examples of parent pullulanase are mentioned above in the "Parent Pullulanases"-section. A pullulanase variant of the invention may have one or more (several) amino acids substituted, deleted, and/or inserted compared to the parent pullulanase in SEQ ID NO: 2, 4 or 34, or another parent pullulanase. The pullulanase variant may be at least 60%, preferably at least 70%, preferably at least 80%, preferably at least 85%, more preferably 90%, more preferably 95%, more preferably 97%, at least 98%, at least 99% identical to the mature parent pullulanase, preferably the parent pullulanases shown in SEQ ID NOs: 2, 4, or 34. The total number of different amino acids in the pullulanase variant compared to the mature parent pullulanase may be fifteen, more preferably fourteen, even more preferably thirteen, even more preferably twelve, even more preferably eleven, even more preferably ten, even more preferably nine, even more preferably eight, even more preferably seven, even more preferably six, even more preferably five, even more preferably four, even more preferably three, even more preferably two, and most preferably one. It is to be understood that a pullulanase variant of the invention has pullulanase activity. In an embodiment the truncation is in the DUF2223a domain or DUF223b domain. According to the invention the truncation is within 100 amino acids, preferably 50 amino acids, preferably 20 amino acids after the end of the X47 domain.

In a specific and preferred embodiment the pullulanase variant of the invention is a variant prepared from a parent pullulanase belonging to family GH57 which comprises an X47 domain, wherein the parent pullulanase is the one shown in SEQ ID NO: 2, 4 or 34, or another parent pullulanase having at least 60% identity to SEQ ID NO: 2, 4, or 34, wherein the pullulanase variant comprises or consists of:

a) An Amino Acid Sequence having Pullulanase Activity;
  i) having at least 60% identity to the sequence from amino acids 1-1009 of SEQ ID NO: 2, preferably to the sequence from amino acids 1-782 of SEQ ID NO: 2; or
  ii) having at least 60% identity to the sequence from amino acids 1-988 of SEQ ID NO: 4, preferably to the sequence from amino acids 1-781 of SEQ ID NO: 4;
  iii) having at least 60% identity to the sequence from amino acids 1-782 of SEQ ID NO: 34;
b) the parent pullulanase of SEQ ID NOS: 2, 4, or 34 is truncated at a position after the X47 domain;
c) another parent pullulanase having at least 60% identity to SEQ ID NOs: 2, 4 or 34 which is truncated in a position corresponding to the ones defined in a) or b);
d) a pullulanase variant defined in a), b) or c) having one or more (several) amino acids substituted, deleted, and/or inserted.

In a preferred embodiment the pullulanase variant has at least 70%, preferably at least 80%, preferably at least 85%, preferably at least 90%, at least 95%, at least 96%, at least 97%, at least 98%, at least 99% identity to the mature part of the pullulanases in SEQ ID NOS: 2, 4 or 34, preferably the sequence from amino acids 1-1009 of SEQ ID NO: 2 or from amino acids 1-987 in SEQ ID NO: 4 (X2 truncation), preferably to the sequence from amino acids 1-782 (X4 truncation) of SEQ ID NOS: 2 or from the sequence from amino acids 1-781 of SEQ ID NO: 4 (X4 truncation) or amino acids 1-782 SEQ ID NO: 34 (X4 truncation). In an embodiment the parent pullulanase is a wild-type pullulanase. In an embodiment the truncation is in the DUF2223a domain located from positions 769-1009 in SEQ ID NO: 2, which corresponds to positions 768-988 in SEQ ID NO: 4, or in a corresponding positions in another parent pullulanase. In a preferred embodiment the truncation is between amino acids in positions 782-783 in SEQ ID NO: 2 (X4 truncation), which corresponds to positions between positions 781-782 in SEQ ID NO: 4, or in corresponding positions in another parent pullulanase. According to the invention the truncation is typically within 100 amino acids, preferably 50 amino acids, preferably 20 amino acids of the end of the X47 domain, which ends at position 768 in SEQ ID NO: 2 and position 767 in SEQ ID NO: 4 and 768 in SEQ ID NO: 34, or a corresponding position in another parent pullulanase. A variant of the invention may have higher pullulanase activity compared to the parent pullulanase. In an embodiment the variant has improved thermostability compared to the corresponding parent pullulanase, especially the parent pullulanase shown in SEQ ID NOS: 2, 4 or 34. The pullulanase variant may have a temperature optimum in the range between 65-100° C., preferably 70-90° C., especially 75-85° C.; and/or may have a pH optimum in the range between pH 40-6.

X47 Domain of the Invention

The present invention also relates to X47 domains. The X47 may be obtainable from a parent pullulanase as exemplified above including from a strain from the genus *Thermococcus*, including *Thermococcus* sp. AM4, *Thermococcus* sp. HJ21, *Thermococcus barophilus*, *Thermococcus gammatolerans*, *Thermococcus kodakarensis*, *Thermococcus litoralis*; *Thermococcus hydrothermalis*; *Thermococcus onnurineus*; or obtained from a strain of the genus *Pyrococcus*, such as *Pyrococcus abyssi* and *Pyrococcus furiosus*. In an embodiment the X47 domain comprising or consisting of the amino acid sequence 580-768 in SEQ ID NO: 2 or amino acid sequence 579-767 in SEQ ID NO: 4 or amino acids 580-768 in SEQ ID NO: 34, or amino acids 86-274 in SEQ ID NO: 38, or a corresponding position in another parent pullulanases. In an embodiment an X47 domain of the invention comprising or consisting of the amino acid sequence 580-768 in SEQ ID NO: 2 or amino acid sequence 579-767 in SEQ ID NO: 4 or amino acids 580-768 in SEQ ID NO: 34, or the amino acid sequence 86-274 in SEQ ID NO: 38, or a corresponding positions in another parent pullulanases determined by Hidden Markov Model (hmm) having a score of at least 300, preferably a score of 350, preferably a score of 400, preferably between 300-500, such as between 380-450. In an embodiment the X47 domain is an amino acid sequence having at least 60% identity to amino acid sequence 580-768 in SEQ ID NO: 2 or to amino acid sequence 579-767 in SEQ ID NO: 4 or amino acid sequence 580-768 in SEQ ID NO: 34, or the amino acid sequence 86-274 in SEQ ID NO: 38. In a preferred embodiment the X47 has at least 70%, preferably at least 80%, preferably at least 85%, preferably at least 90%, at least 95%, at least 96%, at least 97%, at least 98%, at least 99% identity to the amino acid sequence 580-768 in SEQ ID NO: 2 or to amino acid sequence 579-767 in SEQ ID NO: 4 or amino acid sequence 580-768 in SEQ ID NO: 34, or the amino acid sequence 86-274 in SEQ ID NO: 38.

An Isolated Polynucleotide Encoding a Pullulanase Variant or X47 Domain

In an embodiment the invention related to an isolated polynucleotide encoding a pullulanase variant of the invention or an X47 domain of the invention selected from the group consisting of:

i) a polynucleotide having at least 60%, preferably at least 70%, more preferably at least 80%, more preferably at least 90%, more preferably at least 95%, at least 96%, preferably at least 97%, preferably at least 98%, preferably at least 99% identity with the pullulanase variant coding part of SEQ ID NOS: 1 or 3, or a complementary strand thereof;

ii) a polynucleotide having at least 60%, preferably at least 70%, more preferably at least 80%, more preferably at least 90%, more preferably at least 95%, at least 96%, preferably at least 97%, preferably at least 98%, preferably at least 99% identity with the X47 domain coding part of sequence SEQ ID NO: 1, 3, or 37, or a complementary strand thereof; and iii) a polynucleotide which hybridizes under medium stringency, preferably high stringency conditions with the pullulanase variant or X47 domain coding part of SEQ ID NO: 1, 3, or 37, or a complementary strand thereof.

Nucleic Acid Constructs

The present invention also relates to nucleic acid constructs comprising the polynucleotide described above, operably linked to one or more (several) control sequences that direct the expression of the coding sequence in a suitable host cell under conditions compatible with the control sequences. The control sequence may include an appropriate promoter sequence, a nucleotide sequence that is recognized by a host cell for expression of a polynucleotide encoding a pullulanase variant or X47 domain of the present invention. The promoter sequence contains transcriptional control sequences that mediate the expression of the pullulanase variant or X47 domain. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The control sequence may also include a suitable transcription terminator sequence, a sequence recognized by a host cell to terminate transcription. The terminator sequence is operably linked to the 3' terminus of the nucleotide sequence encoding the pullulanase variant or X47 domain in question. Any terminator that is functional in the host cell of choice may be used in the present invention. The control sequence may also include a suitable leader sequence, a non-translated region of an mRNA that is important for translation by the host cell. The leader sequence is operably linked to the 5' terminus of the nucleotide sequence encoding the pullulanase variant or X47 domain of the invention. Any leader sequence that is functional in the host cell of choice may be used in the present invention. The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention. The control sequence may also include a signal peptide coding sequence that codes for an amino acid sequence linked to the amino terminus of a pullulanase variant or X47 domain and directs the encoded pullulanase variant or X47 domain into the cell's secretory pathway. The 5' end of the coding sequence of the nucleotide sequence may inherently contain a signal peptide coding sequence naturally linked in translation reading frame with the segment of the coding sequence that encodes the secreted polypeptide in question. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide in question. However, any signal peptide coding sequence that directs the expressed polypeptide into the secretory pathway of a host cell of choice, i.e., secreted into a culture medium, may be used in the present invention. The control sequence may also include a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide in question. It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Examples of useful control sequences are described in WO 2007/090402.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression. Examples of vector systems are described in WO 2007/090402.

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. Examples of host cells are described in WO 2007/090402.

Methods of Production

The present invention also relates to methods of producing a pullulanase variants or X47 domain of the present invention, comprising: (a) cultivating a cell, which in its wild-type form produces the polypeptide in question, under conditions conducive for production of the polypeptide in question; and (b) recovering the polypeptide in question. The present invention also relates to methods of producing a pullulanase variant or X47 domain of the present invention, comprising: (a) cultivating a recombinant host cell, as described herein, under conditions conducive for production of the polypeptide in question; and (b) recovering the polypeptide in question. The expression level of a pullulanase variant of the invention may according to the invention be the same or higher compared to the corresponding parent pullulanase under the same conditions. The production may be carried out as described in WO 2007/090402.

Processes for Producing Fermentation Products from Un-Gelatinized Starch-Containing Material In this aspect the invention relates to processes for producing fermentation products from starch-containing material without gelatinization (i.e., without cooking) of the starch-containing material. According to the invention the desired fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the desired fermentation product by a suitable fermenting organism. In this embodiment the desired fermentation product, preferably ethanol, is produced from un-gelatinized (i.e., uncooked), preferably milled, cereal grains, such as corn. Accordingly, in the first aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material in the presence of a pullulanase variant of the invention. In an embodiment a protease is also present. The protease may be any acid fungal amylase or metallo protease. Examples are listed below in the "Protease" section. The fermentation product, such as especially ethanol, may optionally be recovered after fermentation, e.g., by distillation. Suitable starch-containing starting materials are listed in the "Starch-Containing Materials"-section below. Contemplated enzymes are listed in the "Enzymes"-section below. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes can be found below and includes raw starch hydrolyzing glucoamylases. Examples of alpha-amylase(s) include acid alpha-amylases, preferably acid fungal alpha-amylases. Examples of fermenting organisms include yeast, preferably a strain of *Saccharomyces cerevisiae*. Other suitable fermenting organisms are listed in the "Fermenting Organisms"-section above. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In context of this invention the initial gelatinization temperature of a given starch-containing material may be determined as the temperature at which birefringence is lost in 5% of the starch granules using the method described by Gorinstein et al., 1992, *Starch/Stärke* 44(12): 461-466. Before initiating the process a slurry of starch-containing material, such as granular starch, having 10-55 w/w-% dry solids (DS), preferably 25-45 w/w-% dry solids, more preferably 30-40 w/w-% dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol.-%, preferably 15-60 vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w-%, such as below about 3 w/w-%, such as below about 2 w/w-%, such as below about 1 w/w-%., such as below about 0.5 w/w-%, or below 0.25 w/w-%, such as below about 0.1 w/w-%. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w-%, such as below about 0.2 w/w-%. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase and a family GH57 pullulanase or;

(b) saccharifying the liquefied material obtained in step (a) using a carbohydrate-source generating enzyme;

(c) fermenting using a fermenting organism.

Examples of family GH57 pullulanasess can be found above. In a preferred embodiment the pullulanase is a pullulanase variant of the invention.

In an embodiment a protease, such as an acid fungal protease or a metallo protease is added before, during and/or after liquefaction. The protease may be any of the ones mentioned below in the "Protease"-section. In a preferred embodiment the metallo protease is derived from a strain of the genus *Thermoascus*, preferably a strain of *Thermoascus aurantiacus*, especially *Thermoascus aurantiacus* CGMCC No. 0670. The alpha-amylase may be any of the ones mentioned in the "Alpha-Amylase"-section below. In a preferred embodiment the alpha-amylase is a fungal alpha-amylase, preferably derived from the genus *Aspergillus*, especially a strain of *A. niger, A. oryzae, A. awamori*, or *A. kawachii*, or of the genus *Rhizomucor*, preferably a strain the *Rhizomucor pusillus*, or the genus *Meripilus*, preferably a strain of *Meripilus giganteus* or the alpha-amylase disclosed in Richardson et al., 2002, *The Journal of Biological Chemistry* 277(29): 267501-26507 (Issue 19 July), referred to as BD5088. The carbohydrate-source generating enzymes may be any of the ones mentioned below in the Carbohydrate-Source Generating Enzyme"-section. In a preferred embodiment the carbohydrate-source generating enzyme is a glucoamylase derived from a strain of *Aspergillus*, preferably *Aspergillus niger* or *Aspergillus awamori*, a strain of *Talaromyces*, especially *Talaromyces emersonii*; or a strain of *Athelia*, especially *Athelia rolfsii*; a strain of *Trametes*, preferably *Trametes cingulata*; a strain of the genus *Pachykytospora*, preferably a strain of *Pachykytospora papyracea*; or a strain of the genus *Leucopaxillus*, preferably *Leucopaxillus giganteus*; or a strain of the genus *Peniophora*, preferably a strain of the species *Peniophora rufomarginata*; or a mixture thereof. Saccharification step (b) and fermentation step (c) may be carried out either sequentially or simultaneously. The pullulanase variant and/or metallo protease may be added during saccharification and/or fermentation when the process is carried out as a sequential saccharification and fermentation process and before or during fermentation when steps (b) and (c) are carried out simultaneously (SSF process). The pullulanase variant and/or metallo protease may also advantageously be added before liquefaction (pre-liquefaction treatment), i.e., before or during step (a), and/or after liquefaction (post liquefaction treatment), i.e., after step (a). The pullulanase variant is most advantageously added before or during liquefaction, i.e., before or during step (a). The fermentation product, such as especially ethanol, may optionally be recovered after fermentation, e.g., by distillation. Suitable starch-containing starting materials are listed in the section "Starch-Containing Materials"-section below. Contemplated enzymes are listed in the "Enzymes"-section below. The liquefaction is preferably carried out in the presence of at least an alpha-amylase, preferably a bacterial alpha-amylase or acid fungal alpha-amylase. The fermenting organism is preferably yeast, preferably a strain of *Saccharomyces cerevisiae*. Suitable fermenting organisms are listed in the "Fermenting Organisms"-section below.

In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In a preferred embodiment the particle size is smaller than a #7 screen, preferably a #6 screen. A #7 screen is usually used in conventional prior art processes. The aqueous slurry may contain from 10-55 w/w-% dry solids (DS), preferably 25-45 w/w-% dry solids (DS), more preferably 30-40 w/w-% dry solids (DS) of starch-containing material. The slurry is heated to above the gelatinization temperature and alpha-amylase, preferably bacterial and/or acid fungal alpha-amylase may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase, together with pullulanase variant and/or protease, preferably metallo protease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase variant and/or protease, preferably metallo protease, is(are) added to finalize hydrolysis (secondary liquefaction). The liquefaction process is usually carried out at pH 4.0-6, in particular at a pH from 4.5 to 5.5. Saccharification step (b) may be carried out using conditions well-known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process in fermentation product, especially ethanol, production is the simultaneous saccharification and fermentation (SSF) process, in which there is no holding stage for the saccharification, meaning that fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Fermentation Medium

"Fermentation media" or "fermentation medium" refers to the environment in which fermentation is carried out and which includes the fermentation substrate, that is, the carbohydrate source that is metabolized by the fermenting organism. The fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, suitable for use in a fermentation process and capable of producing the desired fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$. Commercially available yeast includes, e.g., RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley. The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing and is equally contemplated for a process of the invention. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may preferably be used as fuel. However, in the case of ethanol it may also be used as potable ethanol.

Recovery

Subsequent to fermentation the fermentation product may be separated from the fermentation medium. The slurry may be distilled to extract the desired fermentation product or the desired fermentation product may be extracted from the fermentation medium by micro or membrane filtration techniques. Alternatively the fermentation product may be recovered by stripping. Methods for recovery are well known in the art.

Use of Pullulanase Variants

A pullulanase variant of the invention may be used in the conversion of starch for the production of dextrose, syrup (such as high-fructose syrup), edible products (such as snack pellets), ethanol or beer, e.g., as described in WO 2000/001796, WO 2001/051620, WO 2006/213132, or WO 2003/024242. Thus, it may be used in the liquefaction of starch (WO 2006/028897), in beer brewing (WO 2007/144393), or for saccharification in combination with a glucoamylase (EP 63909).

Enzymes

Proteases

According to the present invention the protease used may be of any origin. In a preferred embodiment the protease may be an acid fungal protease or a metallo protease. In a preferred embodiment the protease is a metalloprotease derived from a strain of the genus *Thermoascus*, preferably a strain of *Thermoascus aurantiacus*, especially *Thermoascus aurantiacus* CGMCC No. 0670 disclosed in WO 2003/048353 (Novozymes). According to the invention a peptidase and other protein degrading enzymes are referred to as proteases. In a preferred embodiment the protease is an endo-protease and/or an exo-protease. Suitable proteases may be of fungal, bacterial, including filamentous fungi and yeast, and plant origin. In an embodiment the protease is an acidic protease, i.e., a protease characterized by the ability to hydrolyze proteins under acidic conditions below pH 7, e.g., at a pH between 2-7. In an embodiment the acidic protease has an optimum pH in the range from 2.5 and 3.5 (determined on high nitrogen casein substrate at 0.7% w/v at 37° C.) and a temperature optimum between 5 to 50° C. at an enzyme concentration of 10 mg/mL at 30° C. for one hour in 0.1 M piperazine/acetate/glycine buffer). In another embodiment the protease is an alkaline protease, i.e., a protease characterized by the ability to hydrolyze proteins under alkaline conditions above pH 7, e.g., at a pH between 7 and 11. In an embodiment the alkaline protease is derived from a strain of *Bacillus*, preferably *Bacillus licheniformis*. In an embodiment the alkaline protease has an optimum temperature in the range from 7 and 11 and a temperature optimum around 70° C. determined at pH 9. In another embodiment the protease is a neutral protease, i.e., a protease characterized by the ability to hydrolyze proteins under conditions between pH 5 and 8. In an embodiment the alkaline protease is derived from a strain of *Bacillus*, preferably *Bacillus amyloliguefaciens*. In an embodiment the alkaline protease has an optimum pH in the range between 7 and 11 (determined at 25° C., 10 minutes reaction time with an enzyme concentration of 0.01-0.2 AU/L) and a temperature optimum between 50° C. and 70° C. (determined at pH 8.5, 10 minutes reaction time and 0.03-0.3 AU/L enzyme concentration. In an embodiment the protease is a metallo protease. In a preferred embodiment the protease is derived from a strain of the genus *Thermoascus*, preferably a strain of *Thermoascus aurantiacus*, especially *Thermoaccus aurantiacus* CGMCC No. 0670 having the sequence shown in the mature part of SEQ ID NO: 2 in WO 2003/048353 hereby incorporated by reference. The *Thermoaccus aurantiacus* protease is active from 20-90° C., with an optimum temperature around 70° C. Further, the enzyme is activity between pH 5-10 with an optimum around pH 6. Suitable plant proteases may be derived from barley. Suitable bacterial proteases include *Bacillus* proteases derived from *Bacillus amyloliguefaciens* and *Bacillus licheniformis*. Suitable filamentous bacterial proteases may be derived from a strain of *Nocardiopsis*, preferably *Nocardiopsis prasina* NRRL 18262 protease (or *Nocardiopsis* sp. 10R) and *Nocardiopsis dassonavilla* NRRL 18133 (*Nocardiopsis dassonavilla* M58-1) both described in WO 88/03947 (Novozymes). Suitable acid fungal proteases include fungal proteases derived from *Aspergillus, Mucor, Rhizomucor, Rhizopus, Candida, Coriolus, Endothia, Enthomophtra, Irpex, Penicillium, Sclerotium, Thermoaccus*, and *Torulopsis*. Especially contemplated are proteases derived from *Aspergillus niger* (see, e.g., Koaze et al., 1964, *Agr. Biol. Chem. Japan* 28, 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42(5): 927-933, *Aspergillus aculeatus* (WO 95/02044), or *Aspergillus oryzae*; proteases from *Mucor pusillus* or *Mucor miehei* disclosed in U.S. Pat. No. 4,357,357 and U.S. Pat. No. 3,988,207; and *Rhizomucor mehei* or *Rhizomucor pusillus* disclosed in, e.g., WO 94/24880 (hereby incorporated by reference). Aspartic acid proteases are described in, for example, Hand-book of Proteolytic Enzymes, Edited by A. J. Barrett, N. D. Rawlings and J. F. Woessner, Aca-demic Press, San Diego, 1998, Chapter 270). Suitable examples of aspartic acid protease include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference. Commercially available products include ALCALASE®, ESPERASE™, NEUTRASE®, RENILASE®, NOVOZYM™ FM 2.0L, and NOVOZYM™ 50006 (available from Novozymes A/S, Denmark) and GC106™ and SPEZYME™ FAN from Genencor Int., Inc., USA. The protease may be present in concentrations in the range from 0.0001 to 1.0 wt.-% of TS, preferably 0.001 to 0.1 wt.-% of TS.

Alpha-Amylase

According to the invention any alpha-amylase may be used, such as of fungal, bacterial or plant origin. In a preferred embodiment the alpha-amylase is an acid alpha-amylase, e.g., acid fungal alpha-amylase or acid bacterial alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylase

According to the invention a bacterial alpha-amylase is preferably derived from the genus *Bacillus*. In a preferred embodiment the *Bacillus* alpha-amylase is derived from a strain of *Bacillus licheniformis, Bacillus amyloliguefaciens, Bacillus subtilis* or *Bacillus stearothermophilus*, but may also be derived from other *Bacillus* sp. Specific examples of contemplated alpha-amylases include the *Bacillus licheniformis* alpha-amylase shown in SEQ ID NO: 4 in WO 99/19467, the *Bacillus amyloliguefaciens* alpha-amylase SEQ ID NO: 5 in WO 99/19467 and the *Bacillus stearothermophilus* alpha-amylase shown in SEQ ID NO: 3 in WO 99/19467 (all sequences hereby incorporated by reference). In an embodiment the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in SEQ ID NOS: 1, 2 or 3, respectively, in WO 99/19467. The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093, 562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 96/23873—see, e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted I181*+G182*+N193F) compared to the wild-type BSG alpha-amylase amino acid sequence set forth in SEQ ID NO:3 disclosed in WO 99/19467.

Bacterial Hybrid Alpha-Amylase

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliguefaciens*

(shown in SEQ ID NO: 5 of WO 99/19467), with one or more, especially all, of the following substitution:

G48A+T49I+G107A+H156Y+A181T+N190F+I201F+
A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467). In an embodiment the bacterial alpha-amylase is dosed in an amount of 0.0005-5 KNU per g DS, preferably 0.001-1 KNU per g DS, such as around 0.050 KNU per g DS.

Fungal Alpha-Amylase

Fungal Alpha-Amylases Include Alpha-Amylases Derived from a Strain of the Genus *Aspergillus*, such as *Aspergillus oryzae, Aspergillus niger* and *Aspergillis kawachii* Alpha-Amylases.

A preferred acidic fungal alpha-amylase is a Fungamyl-like alpha-amylase which is derived from a strain of *Aspergillus oryzae*. According to the present invention, the term "Fungamyl-like alpha-amylase" indicates an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874. Another preferred acid alpha-amylase is derived from a strain *Aspergillus niger*. In a preferred embodiment the acid fungal alpha-amylase is the one from *Aspergillus niger* disclosed as "AMYA_ASPNG" in the Swiss-prot/TeEMBL database under the primary accession no. P56271 and described in WO 89/01969 (Example 3—incorporated by reference). A commercially available acid fungal alpha-amylase derived from *Aspergillus niger* is SP288 (available from Novozymes NS, Denmark). Other contemplated wild-type alpha-amylases include those derived from a strain of the genera *Rhizomucor* and *Meripilus*, preferably a strain of *Rhizomucor pusillus* (WO 2004/055178 incorporated by reference) or *Meripilus giganteus*. In a preferred embodiment the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*, and further as EMBL: #AB008370. The fungal alpha-amylase may also be a wild-type enzyme comprising a starch-binding domain (SBD) and an alpha-amylase catalytic domain (i.e., non-hybrid), or a variant thereof. In an embodiment the wild-type alpha-amylase is derived from a strain of *Aspergillus kawachii*.

Fungal Hybrid Alpha-Amylase

In a preferred embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker. Specific examples of contemplated hybrid alpha-amylases include those disclosed in Table 1 to 5 of the examples in U.S. patent application No. 60/638,614, including Fungamyl variant with catalytic domain JA118 and *Athelia rolfsii* SBD (SEQ ID NO:100 in U.S. 60/638,614), *Rhizomucor pusillus* alpha-amylase with *Athelia rolfsii* AMG linker and SBD (SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO:102 in U.S. 60/638,614). Other specifically contemplated hybrid alpha-amylases are any of the ones listed in Tables 3, 4, 5, and 6 in Example 4 in U.S. application Ser. No. 11/316,535 and WO 2006/069290 (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain. Contemplated are also alpha-amylases which exhibit a high identity to any of above mention alpha-amylases, i.e., at least 70%, at least 75%, at least 80%, at least 85%, at least 90%, at least 95%, at least 96%, at least 97%, at least 98%, at least 99% or even 100% identity to the mature enzyme sequences. An acid alpha-amylases may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

Commercial Alpha-Amylase Products

Preferred commercial compositions comprising alpha-amylase include MYCOLASE™ from DSM (Gist Brocades), BAN™, TERMAMYL™ SC, FUNGAMYL™, LIQUOZYME™ X, LIQUOZYME™ SC and SAN™ SUPER, SAN™ EXTRA L (Novozymes NS) and CLARASE™ L-40,000, DEX-LO™, SPEZYME™ FRED, SPEZYME™ AA, and SPEZYME™ DELTA AA, SPEZYME™ XTRA, GC358 (Genencor Int.), FUELZYME™-LF (Verenium Inc), and the acid fungal alpha-amylase sold under the trade name SP288 (available from Novozymes NS, Denmark).

Carbohydrate-Source Generating Enzyme

The term "carbohydrate-source generating enzyme" includes glucoamylase (being glucose generators), beta-amylase and maltogenic amylase (being maltose generators) and also alpha-glucosidase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated blends are mixtures comprising at least a glucoamylase and an alpha-amylase, especially an acid amylase, even more preferred an acid fungal alpha-amylase. The ratio between glucoamylase activity (AGU) and fungal alpha-amylase activity (FAU-F) (i.e., AGU per FAU-F) may in a preferred embodiment of the invention be between 0.1 and 100 AGU/FAU-F, in particular between 2 and 50 AGU/FAU-F, such as in the range from 10-40 AGU/FAU-F, especially when doing one-step fermentation (Raw Starch Hydrolysis—RSH), i.e., when saccharification and fermentation are carried out simultaneously (i.e., without a liquefaction step). In a conventional starch-to-ethanol process (i.e., including a liquefaction step (a)) the ratio may preferably be as defined in EP 140,410-B1, especially when saccharification in step (b) and fermentation in step (c) are carried out simultaneously.

Glucoamylase

A glucoamylase used according to the invention may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, EMBO J. 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (*Agric. Biol. Chem.* 55(4): 941-949 (1991)), or variants or fragments thereof. Other *Aspergillus glucoamylase* variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in position A435 and S436 (Li et al., 1997, *Protein Eng.* 10: 1199-1204. Other glucoamylases include *Athelia rolfsii* (previously denoted *Corticium rolfsii*) glucoamylase (see U.S. Pat. No. 4,727,026 and (Nagasaka et al., 1998, "Purification and properties of the raw-starch-degrading glucoamylases from *Corticium rolfsii*, *Appl Microbiol Biotechnol.* 50:323-330), *Talaromyces glucoamylases*, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Bacterial glucoamylases contemplated include glucoamylases from the genus *Clostridium*, in particular *C. thermoamylolyticum* (EP 135, 138), and *C. thermohydrosulfuricum* (WO 86/01831) and *Trametes cingulata, Pachykytospora papyracea*; and *Leucopaxillus giganteus* all disclosed in WO 2006/069289; or *Peniophora rufomarginata* disclosed in WO 2007/124285; or a mixture thereof. Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference). Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above. Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Genencor Int.). Glucoamylases may in an embodiment be added in an amount of 0.0001-20 AGU/g DS, preferably 0.001-10 AGU/g DS, especially between 0.01-5 AGU/g DS, such as 0.1-2 AGU/g DS.

Beta-Amylase

A beta-amylase (E.C3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase. Beta-amylases have been isolated from various plants and microorganisms (Fogarty et al., 1979, *Progress in Industrial Microbiology* 15: 112-115). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylase

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598, 048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Materials & Methods

Materials:

Parent Pullulanase H: *Thermococcus hydrothermalis* pullulanase (Uniprot: Q9Y8I8) disclosed in SEQ ID NO: 2.

Parent Pullulanase L: *Thermococcus litoralis* pullulanase (UNIPROT: Q8NKS8 and disclosed in SEQ ID NO: 4.

Alpha-Amylase FZ: Alpha-amylase as disclosed in Richardson et al., 2002, *The Journal of Biological Chemistry* 277 (29): 267501-26507 (Issue 19 July), referred to as BD5088. This alpha-amylase is the same as the one shown in SEQ ID NO: 4 herein. The mature enzyme sequence starts after the initial "Met" amino acid in position 1. The enzyme is available from Verenium (USA).

Alpha-Amylase SC: *Bacillus stearothermophilus* alpha-amylase, which has a double deletion corresponding to delta (181-182) and further comprise a N193F substitution.

Protease A: Metallo protease derived from *Thermoascus aurantiacus* CGMCC No. 0670 disclosed as amino acids 1-177 in SEQ ID NO: 1 herein and amino acids 1-177 in SEQ ID NO: 2 in WO 2003/048353.

Glucoamylase SF: Blend of *Tamaromyces emersonii* glucoamylase disclosed in WO 99/28448 as SEQ ID NO: 7 and *Trametes cingulata* glucoamylase disclosed in WO06/ 069289 in a ratio of about 9:1.

BMSY medium: (1% yeast extract, 2% peptone, 100 mM potassium phosphate buffer, pH 6.0, 1.34% YNB, 4×10-5% biotin, 2% sorbitol)

Methods:

Hidden Markov Model (HMM):

The strategy for creating the Hidden Markov Model is as indicated below. The model is constructed using a multiple alignment of X47 domain sequences shown in SEQ ID NO: 20-30 as the only input:

1) Extract sequences which are used for the model (Cazy/ eFAM)
2) Make a multiple alignment of those sequences
3) Using 'hmmbuild' (part of hmmer package v. 2.3.2) for constructing the model
4) The model is calibrated using random sequences, using hmmcalibrate
5) The program 'hmmsearch' can then be used to query any database using the model.

Tasks 2-4 are repeated on all sequences that identified using the first model. This provides more diversity to the model, going from 5 to 11 sequences included.

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile. A folder EB-SM-0009.02/01 describing this analytical method in more detail is available upon request to Novozymes NS, Denmark, which folder is hereby included by reference.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| | |
|---|---|
| Substrate | Soluble starch |
| Temperature | 37° C. |
| pH | 4.7 |
| Reaction time | 7-20 minutes |

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, Denmark, glucoamylase wild-type Aspergillus niger G1, also disclosed in Boel et al., 1984, *EMBO J.* 3(5): 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions Iodine forms a blue complex with starch but not with its degradation products. The intensity of color is therefore directly proportional to the concentration of starch. Amylase activity is determined using reverse colorimetry as a reduction in the concentration of starch under specified analytic conditions.

| | Alpha-amylase | |
|---|---|---|
| Starch + Iodine | → | Dextrins + Oligosaccharides |
| | 40° C., pH 2.5 | |
| Blue/violet | t = 23 sec. | Decoloration |

Standard conditions/reaction conditions: (per minute)
Substrate: Starch, approx. 0.17 g/L
Buffer: Citate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: lambda=590 nm
Enzyme concentration: 0.025 AFAU/mL
Enzyme working range: 0.01-0.04 AFAU/mL If further details are preferred these can be found in EB-SM-0259.02/01 available on request from Novozymes A/S, Denmark, and incorporated by reference.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes. An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Protease Assays

The following assays for protease activity were used:

AZCL-Casein Assay

A solution of 0.2% of the blue substrate AZCL-casein is suspended in Borax/$NaH_2PO_4$ buffer pH9 while stirring. (For pH profile the buffer system pH 3 to pH 11 is used instead). The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease sample is added to a microtiter plate and the assay is started by adding 100 microL 1 mM pNA substrate (5 mg dissolved in 100 microL DMSO and further diluted to 10 mL with Borax/$NaH_2PO_4$ buffer pH9.0). The increase in $OD_{405}$ at room temperature is monitored as a measure of the protease activity.

Determination of Maltogenic Amylase activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

Protein Concentration Determination

The protein concentration of the enzyme preparation is determined initially by measuring the absorbance of triplicate samples at 280 nm and then calculating the protein concentration using Lambert-Beers law and a conversion factor (E) of 2.20. The conversion factor is based on the theoretical molar extinction coefficient which in turn is obtained from the sequence. In addition to the absorbance measurement, samples are sent to amino acid analysis by acid hydrolysis to obtain a more accurate measure of the enzyme concentration. In the time between sampling and receiving the data from the amino acid analysis the enzyme concentration estimate from the absorbance measurement is used for subsequent experiments.

Determination of pH optimum of Pullulanases

The pH optima for the enzymes are measured at 6 pHs (3, 4, 5, 6, 7 and 8) and at different dilutions of protein as required. All data points are results of duplicate measurements. Substrate solutions are prepared containing 0.2% AZCL-pullulan in Britton Robinson buffer (50 mM phosphate, 50 mM Succinate, 50 mM Borate) which provides buffering capacity in the interval between pH 2 and 11. 270 microliters substrate solution is then transferred to a 96-well micro-titer plate and 18 microliters enzyme solution added. After addition of enzyme, the plates are incubated at 40° C. in a thermo-block with shaking for 15 minutes and then centrifuged using a centrifuge rotor specially adapted for micro-titer plates. After centrifugation 150 microliters of the supernatant is transferred to a new micro-titer plate and the absorbance at 595 nm measured.

Determination of Temperature Optimum of Pullulanases

The temperature optima for the enzymes are measured using a slightly modified version of the AZCL-pullulan protocol. Triplicate samples containing 750 microliters substrate solution (0.2% AZCL pullulan in 25 mM Na Acetate, pH 4.5) are prepared for each temperature. The samples are then pre-warmed to the desired temperatures for 5 minutes. After warming 50 microliters enzyme solution is added. The tubes are then directly put in thermo-blocks set at the desired temperatures and incubated with shaking for 20 minutes. After incubation the samples are put on ice for 2 minutes and then centrifuged in a bench-top centrifuge to pellet the un-degraded substrate. A volume of the supernatant is then withdrawn from each sample and added to a well in a 96-well micro-titer plate and diluted with substrate solution without AZCL-pullulan as necessary. The absorbance of each sample is then measured at 650 nm and the standard deviation of the triplicate samples calculated for each temperature.

Determination of Inactivation Temperature

Inactivation of pullulanase is tested by incubating a 1 ml 0.29 mg/ml sample at 85° C. for 1.5 hours. After incubation the sample is put on ice for 5 minutes to cool down and then centrifuged at maximum speed at 4° C. in a bench top centrifuge for 5 minutes. 600 microliters of the supernatant is then carefully removed and transferred to a new tube. 5×50 microliters supernatant is then added to five tubes containing 750 microliters AZCL-pullulan in 50 mM Na Acetate, pH 4.5. The samples are then incubated at 60° C. for 20 minutes in a thermo-block with constant shaking. In parallel to the heat inactivated sample a non-heat incubated sample is treated and assayed exactly like the heat treated sample to serve as a negative control and for normalization of the data.

Determination of Temperature Stability (DSC)

The temperature stability of the enzyme is determined by differential scanning calorimetry (DSC). Briefly, a 2.5 ml 1 mg/ml enzyme sample is prepared by diluting 431 microliters of the *T. litoralis—T. hydrothermalis* pullulanase chimera with DSC buffer (10 mM NaAc, 50 mM NaCl, pH 5.0) to the desired volume. The enzyme sample is then applied to a PD10 desalting column pre equilibrated with 25 of the DSC buffer and eluted with an additional 3.5 mL of the same buffer. The enzyme sample and a reference sample consisting of the DSC buffer without enzyme is then degassed for 45 minutes to remove dissolved air which could interfere with the experiment. After degassing, 512 microliters of the enzyme solution and of the DSC buffer are loaded into the sample cell and the reference cell respectively. Scanning is then done once between 20° and 120° with a heating rate of 90° per hour. The maximum of the resulting peak in the thermo gram is taken to be the denaturation temperature or Td.

EXAMPLES

Example 1

Cloning and Expression of *Thermococcus hydrothermalis* DSM 14834 Pullulanase in *Bacillus subtilis*

A synthetic gene based on the protein sequence of *Thermococcus hydrothermalis* DSM 14834 Apu (Uniprot: Q9Y8I8) was designed and the gene was codon optimized for *Bacillus subtilis*. The C-terminal sequence (including the part of the putative linker, indicated in the alignment—FIG. 1) TPTESPTETTTTP-SETTTTTSTTTGPSSTTTSTPGGGICG-PGIIAGLALIPLLLKRRN (SEQ ID NO: 5) and the native signal peptide (MRRVVALFIAILMLGSIVGANVKSVG—SEQ ID NO: 6) was not part of the designed synthetic gene (SEQ ID NO: 1 (DNA) and SEQ ID NO: 2 (protein)). The synthetic gene was extracted by double-digestion according to the manufacturer's manual (FastDigest®, Fermentas, Germany) from a plasmid carrying the synthetic gene. The synthetic gene was cloned in an expression vector comprising the genetic elements as described in WO 99/43835 (hereby incorporated by reference). By doing so, the signal peptide from the alkaline protease from *Bacillus clausii* (aprH) was fused to the synthetic gene as described in WO 99/43835 in frame to the DNA encoding the truncated apu gene. Alternatively, the aprH signal peptide was extended N-terminally by the amino acids HQHQHQHPR which enabled us to purify the mature peptide by affinity chromatography.

```
aprH signal peptide:
                                    (SEQ ID NO: 18)
MKKPLGKIVASTALLISVAFSSSIASA aprH signal peptide including HQ tag:
                                    (SEQ ID NO: 19)
MKKPLGKIVASTALLISVAFSSSIASAHQHQHQHPR
```

Figure 2:
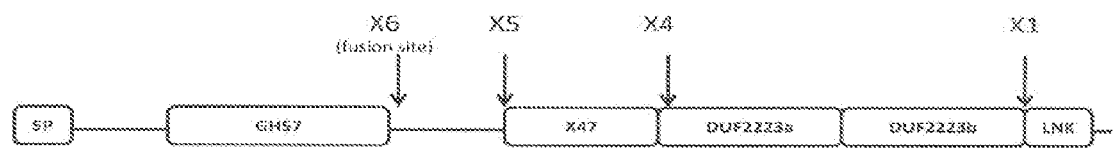
FIG. 2 shows the truncation points X1, X4, X5 and X6 in the parent pullulanase derived from *Thermococcus hydrothermalis* (UNIPROT:Q9Y8I8).
Figure 3:
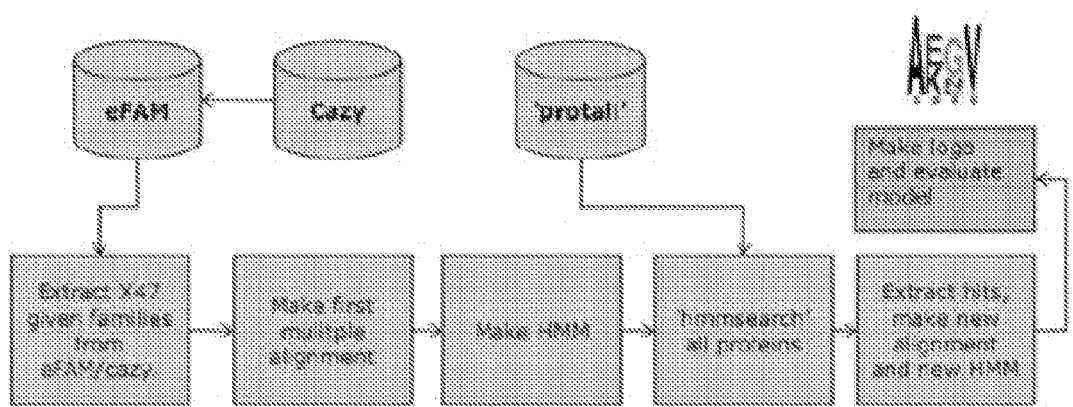
FIG. 3 shows the HMM process used for identifying X47 domains.

The derived expression plasmidC1MW containing the apu coding sequence with aprH signal plus HQ affinity tag was integrated by homologous recombination into a *Bacillus subtilis* host cell genome. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315). This cloning work resulted in truncation site X1 of *T. hydrothermalis* pullulanase (FIG. 2).

Chloramphenicol resistant clones were analyzed by DNA sequencing to verify the correct DNA sequence of the construct. One expression clone was selected and was cultivated on a rotary shaking table in 500 ml baffled Erlenmeyer flasks each containing 100 ml casein based media supplemented with 6 mg/l chloramphenicol. The clone was cultivated for 3-5 days at 37° C. Pullulanase activity in the culture broth was determined as described in Example 4.

Example 2

Cloning and Expression of Variants of *Thermococcus hydrothermalis* DSM 14834 Pullulanase in *Bacillus subtilis*

In order to increase the recombinant expression yield of Apu and to identify which domains are necessary for the pullulanase activity, we have made truncations of the enzyme. The expression plasmid containing the synthetic gene described in Example 1 was used as template for a PCR(1). PCR(1) was performed in a total volume of 26 microliters, the following reagents were added, 1 microliter of vector DNA preparation (template), 50 pmol of each of the primer pairs below, 5 microliters dNTPs and 0.5 microliter Phusion® polymerase (Finnzymes, Finland) in Phusion HF buffer. The PCR conditions were 98° C. for 2 min; 9 cycles of 98° C. for 15 sec; 65° C. for 45 sec; 72° C. for 4 min; followed by 72° C. for 10 min; 4° C. for 20 min and 15° C. until the end of the PCR program. The primer pairs used were:

```
For X4 truncation:
1354
                                    (SEQ ID NO: 31)
5'- GCCAAGGCCGGTTTTTTATGTTTTACTTAAGGATTACGCGAGCAT
TG
and C52X4r
                                    (SEQ ID NO: 9)
5'- TGATTAACGCGTTTAAGTATAGTTGCCAGGGCCATGG For X5 truncation:
1354
                                    (SEQ ID NO: 31)
5'- GCCAAGGCCGGTTTTTTATGTTTTACTTAAGGATTACGCGAGCAT
TG
and C52X5r
                                    (SEQ ID NO: 10)
5'- TGATTAACGCGTTTAAGGAGGCTCAACGC
```

The obtained PCR products were each cloned into an expression vector as described in Example 1. The DNA sequences of the derived expression vectors were verified by Sanger sequencing which is within the general knowledge of one skilled in the art.

The plasmids were each integrated by homologous recombination into the *Bacillus subtilis* host cell genome leading to truncations X4 and X5. Genomic DNA from each of the cultivated clones was prepared and used to transform a protease weak *Bacillus subtilis* host strain. Selection of one clone and pullulanase activity determination was performed as described in Example 1.

Example 3

Cloning and Expression of a Truncated Pullulanase Fusion of *Thermococcus litoralis* DSM 5473 and *Thermococcus hydrothermalis* DSM 14834 in *Bacillus subtilis*

A truncated synthetic gene based on the protein sequence of *Thermococcus litoralis* DSM 5473 was designed and the gene was codon optimized for *Bacillus subtilis*. In the synthetic gene, the C-terminal sequence after amino acid 474 in SEQ ID NO: 4 was deleted as indicated in the alignment FIG. 2 ("X6 truncation").

Cloning of the synthetic gene into *Bacillis subtilis* the selection of correct clones and the cultivation of the clones was performed as described in Example 1. The X6 truncation of *T. litoralis* did not display any pullulanase activity (see table in Example 4). The derived expression plasmid C526A was used in a following PCR amplification as template.

Fusion of *Thermococcus litoralis* and *Thermococcus hydrothermalis* DNA

Using the expression plasmid C526A carrying the apu gene from *Thermococcus litoralis* as template, a PCR was performed in a total volume of 50 microliters. The following reagents were added, 1 microL of the template DNA, 50 pmol of each of the primers (SEQ ID NOS: 19 and 8), dNTPs and Phusion® polymerase (Finnzymes, Finland) in Phusion HF buffer. The PCR conditions were 98° C. for 30 sec; 36 cycles of 98° C. for 10 sec; 65° C. for 20 sec; 72° C. for 90 sec; followed by 72° C. for 10 min; and 4° C. until the end of the PCR program.

The primers used were:
Tlito.r 5'-CGGCGTAAGCTTGTTTGCCT (SEQ ID NO: 7)
1354 5'-GCCAAGGCCGGTTTTTTATGTTTTACT-TAAGGATTACGCGAGCATTG (SEQ ID NO: 31) where SEQ ID NO: 31 binds in a genetic element of *Bacillus subtilis* as referenced in Example 1 and SEQ ID NO: 7 binds on the reverse strand of the apu synthetic gene from *Thermococcus litoralis*.

The expression plasmid containing the *Thermococcus hydrothermalis* synthetic gene described in Example 1 was used as template for another PCR reaction which was performed under the same conditions as described above with the exception that the primers used were:

```
C52X4r
                                    (SEQ ID NO: 32)
5'-TGATTAACGCGTTTAAGTATAGTTGCCAGGGCCATGG

Fusion.f
                                    (SEQ ID NO: 8)
5'-aggcaaacaagcttacgccgcgcatgatggagcgcctt
```

The obtained PCR products from both PCR reactions from Example 3 were purified under recommended conditions from the manufacturer (GFX DNA purification kit, GE Healthcare). The purified PCR products where used as template in a fusion PCR which was performed in a total volume of 50 microliters, the following reagents were added, 1 microliter of a 5 times dilution of each PCR fragments in water, 50 pmol of each of the primers SEQ ID NOs: 31 and 32, dNTPs and Phusion® polymerase (Finnzymes, Finland) in Phusion HF buffer. The PCR conditions were 98° C. for 30 sec; 36 cycles of 98° C. for 10 sec; 65° C. for 20 sec; 72° C. for 150 sec; followed by 72° C. for 10 min; and 4° C. until the end of the PCR program.

The fusion PCR reaction product of approx. 3 kb was purified and integrated by homologous recombination into the *Bacillus subtilis* host cell genome leading to a *T. hydrothermalis/T. litoralis* hybrid enzyme with truncation site X4 (see FIG. 2), i.e., the hybrid has an amino acid sequence from 1-782 in SEQ ID NO: 34. Genomic DNA of one correct clone was prepared and used to transform a protease weak *Bacillus subtilis* host strain. Selection of one clone and pullulanase activity determination was performed as described in Example 1. Likewise, another hybrid was produced by using primer SEQ ID NO: 33 instead of SEQ ID NO: 32 which yielded in a *T. hydrothermalis/T. litoralis* hybrid enzyme with truncation site X5 (FIG. 2), i.e., the hybrid has the amino acid sequence from position 1-581 in SEQ ID NO: 34.

Example 4

Determination of Pullulanase Activity

AZCL-pullulan plates with different pH were prepared as follows: 115.2 ml Britton-Robinson buffer and 284.8 ml deionized water were mixed and pH was adjusted to 4.5 or 7.0 by adding 2 N NaOH. Subsequently 4 g Agarose type II (Sigma A6877) was added and the solution was heated with stirring until the agarose was dissolved. After cooling down (to around 55° C.) with stirring, approx. 0.025% AZCL-Pullulan (Megazyme) was added and 70 ml was poured in a 14 cm plate. Wells with 4 mm diameter were punched out.

Amylopectin plates were prepared as follows. 400 ml BT-agar (6.25 g/L Tryptone, 6.25 g/L Amylopectin Hydrate, 25 g/L granulated agar in 'ionbytte' water) at 55° C. was mixed with 100 ml Ba2 (1 g/L (NH$_4$)$_2$SO$_4$, 2.5 g/L MgSO$_4$.7H$_2$O, 1.25 g/L CaCl$_2$.2H$_2$O, 15 g/L KH$_2$PO$_4$ in 'ionbyttet' water) and 70 ml was poured in a 14 cm plate. 500 microliters samples were taken from the cultures described in the previous examples and centrifuged at 10.000 rpm for 10 min at 12° C. 10 µl of the supernatant was spotted on the different activity plates and incubated at 70° C. or 80° C. After approx. 16 hrs, activity of the different clones was scored by measuring the diameter of the halos (see Table below, numbers are halo diameter in mm, 0 indicates no observed activity).

| Construct no. | Donor | Truncation site | AZCL pullulan pH 4.5 | AZCL pullulan pH 7.0 | ATBa2 pH 5.5 |
|---|---|---|---|---|---|
| B. subtilis host strain | Negative control | — | 0 | 0 | 0 |
| C1MW | T. hydrothermalis | X1 | 4 | 2 | 3 |
| C52X4 | T. hydrothermalis | X4 | 5 | 7 | 6 |
| C52X5 | T. hydrothermalis | X5 | 0 | 0 | 0 |
| C526A | T. litoralis | X6 | 0 | 0 | 0 |
| C629Z | T. litoralis + hydrothermalis fusion site at X6 | X4 | 9 | 8 | 3 |
| C629Y | T. litoralis + hydrothermalis fusion site at X6 | X5 | 2 | 0 | 8 |

Truncation X4 showed increased activity over a broad pH range compared to the longest X1 truncation construct. The X4 hybrid showed overall greater activity than the *Thermococcus hydrothermalis* X4 truncation. Truncations X5 and X6 completely lost their pullulanase activity, only minimal activity was observed for the X5 hybrid at pH 4.5. This indicates the importance of the X47 domain for enzyme activity, which is missing in X5 and X6 truncated constructs.

Example 5

Cloning and Expression of *Thermococcus hydrothermalis* DSM14834 Pullulanase in *Pichia pastoris*

A synthetic gene based on the mature form of protein *Thermococcus hydrothermalis* DSM 14834 Apu (Uniprot: Q9Y8I8) was designed and the gene was codon optimized for *Pichia pastoris*. The C-terminal sequence (putative linker) EFHQHQHQHQHQHP (SEQ ID NO: 12) and the Signal peptide: (MRFPSIFTAVLFAASSALAAPVNTTTE-DETAQIPAEAVIGYSDLEGDFDVAVLPFSNSTNNGLLF INTTIASIAAKEEGVSLEKR—SEQ ID NO: 13) was not part of the designed synthetic gene (SEQ ID NO: 14 (DNA) and SEQ ID NO: 15 (mature protein sequence).

The synthetic gene was amplified from a plasmid carrying the synthetic gene by Phusion polymerase with

```
forward primer:
                                        (SEQ ID NO: 16)
(AGGGGTATCTCTCGAGAAAAGAGCTGAGCCAAAGCCTTTGAACG
and reverse primer:
                                        (SEQ ID NO: 17)
GGTGCTGATGGAATTCTGGCTCCTCTCCACCAGTTC.
```

The amplification is under recommended conditions from the manufacturer. The resulting PCR fragment was purified by gel extraction kit, and subcloned into a *pichia* expression vector pLIZG8HQ at XhoI and EcoRI sites, according to the standard procedure of Infusion kit. By doing so, the synthetic gene was fused in-frame with alpha-factor signal peptide at the 5'-end, as well as HQ tag at the 3'-end. The screening for the plasmid DNA is also within the general knowledge of one skilled in the art.

The resulting expression construct was sequence confirmed and named pC1QB. The plasmid was transformed into *Pichia pastoris* using standard electroporation protocol (cf. WO 2004/069872-A1). The resulting transformants were grown in BMSY media for 2 days at 28° C. with vigorous shaking. Then cells were induced for 3 days with a daily supplement of 0.5% methanol. The culture supernatant was screened for pullulanase expression using blue substrate AZCL-HE-pullulan (Megazyme) by microtiter plate assay. The absorbance is measured by BioRad Microplate Reader at 595 nm. For checking of purity and determining the molecular weight of purified pullulanase, the culture supernatant was applied to invitrogen SDS-polyacrylamide gel electrophoresis. The transformant both giving the highest OD595 and the strongest band was chosen for further fermentation and subsequent purification of the pullulanase.

Example 6

Characterization of Pullulanase Variants Expressed in *Pichia pastoris*

Differing from the methods described in the method section, the pullulanases expressed in *P. pastoris* were purified and characterized as follows:
Purification of Pullulanase
The supernatant of a *Pichia pastoris* clone corresponding to truncation site X1 was filtered through a 0.45 micro m filter. The solution was applied to a 40 mL Ni-sepharose column (GE healthcare) equilibrated with 20 mM PBS, 0.3 M NaCl, pH 7.0, and the protein was eluted with a linear increase of imidazole concentration. Fractions from the column were analyzed for pullulanase activity and SDS-PAGE.
Temperature Profile
100 microL 0.4% AZCL-HE-pullulan and 150 µl buffer at pH 4.5 were pre-incubated at 50-95° C. in 1.5 mL tubes for 5 mins before adding 10 microL pullulanase sample. The reactions were performed at corresponding temperature for 30 min with shaking at 1000 rpm for 30 mins. The tubes were put on ice after reaction and 100 microliters supernatant was transferred to a microtiter plate. OD595 was read as a measure of pullulanase. For each enzyme the reaction was performed triplicate.

|  | Temperature | | | | | | |
| --- | --- | --- | --- | --- | --- | --- | --- |
|  | 50 | 60 | 70 | 80 | 85 | 90 | 95 |
| Relative activity (%) | 50.9 | 42.9 | 72.1 | 100 | 57.4 | 40.1 | 62.4 |

Temperature Stability 10 microL pullulanase samples and 150 microL buffer at pH 4.5 were incubated at 80° C. for 0, 5, 10, 30, 60 and 120 min. After incubation, 100 microL 0.4% AZCL-HE—pullulan was added to the plate. The reactions were performed at 50° C. for 30 min. 100 microliters supernatant was transferred to a micro-titer plate for reading at OD595.

|  | Incubation time (min) | | | | | |
| --- | --- | --- | --- | --- | --- | --- |
|  | 0 | 5 | 10 | 30 | 60 | 120 |
| Relative activity (%) | 100 | 196.6 | 149.2 | 163.2 | 185.9 | 140.8 | pH Profile pH buffers: 100 mM Succinic acid, HEPES, CHES, CAPSO, 1 mM $CaCl_2$, 150 mM KCl, 0.01% Triton X-100, pH adjusted to 3.5, 4.0, 4.5, 5.0, 6.0 7.0, 8.0, and 9.0 with HCl and NaOH.

5 microL pullulanase sample, 100 microL 0.4% AZCL-HE—pullulan (in MilliQ) and 150 microL 50 mM pH buffer (3.5-9) were mixed in a microtiter plate and placed on ice before reaction. The reactions were performed at 70° C., for 30 min. 100 microL supernatant was transferred to a new microtiter plate. OD595 was read as a measure of pullulanase activity. For each enzyme the reaction was performed in triplicate.

|  | pH | | | | | | | |
| --- | --- | --- | --- | --- | --- | --- | --- | --- |
|  | 3.5 | 4 | 4.5 | 5 | 6 | 7 | 8 | 9 |
| Relative activity (%) | 14.8 | 47.5 | 76.9 | 100 | 76.7 | 67.4 | 72.9 | 66.6 | pH Stability 10 microL sample and 150 buffer at pH4.5 were incubated for 0, 5, 10, 30, 60 and 120 min at 80° C. 100 MicroL supernatant was transferred to a new microtiter plate and 50 microL 0.4% AZCL-HE-pullulan was added. OD595 was read as a measure of pullulanase activity. For each enzyme the reaction was performed in triplicate.

|  | Incubation time (min) | | | | | |
| --- | --- | --- | --- | --- | --- | --- |
|  | 0 | 5 | 10 | 30 | 60 | 120 |
| Relative activity (%) | 17.9 | 69.2 | 100 | 57.9 | 65.6 | 32.9 |

Example 7

Purification of *Thermococcus litoralis*—*Thermococcus hydrothermalis* Chimeric Pullulanase The *Bacillus subtilis* clone culture supernatant was heat treated at 80° C. for 15 min and then adjusted in pH to 8.0 by addition of NaOH and subsequently centrifuged at 7000 rpm for 20 minutes and filtered through a 0.22 micro-m PES bottle top filter. Purification was done by immobilized metal ion affinity chromatography (IMAC) using an Äkta purifier FPLC system and a Ni-NTA Sepharose FF column. After equilibration of the column with 5 column volumes of Buffer A1 (25 mM Tris/HCl, pH 8.0) the sample was applied. Then the column was washed with 5 column volumes of buffer A1 and finally the protein was eluted by a gradient of 0-100% Buffer B1 (25 mM Tris/HCl, 500 mM imidazole, pH 8.0). Fractions were collected throughout the gradient and assayed for pullulanase activity on AZCL-pullulan and protein content by SDS-PAGE. The fractions displaying the highest activity and with protein bands of the correct size in an SDS-PAGE were pooled and buffer shifted by a 1 L G25 desalting column into Buffer A2 (25 mM MES, pH 6.5). The buffer shifted enzyme solution was then applied to a Source 15Q anion exchange column pre-equilibrated with 5 column volumes of Buffer A2. After loading the sample, the column was washed with 5 column volumes of buffer A2 and finally the protein was eluted by a gradient of 0-100% Buffer B2 (25 mM MES, 500 mM NaCl, pH 6.5). Fractions were collected throughout the gradient and assayed for pullulanase activity on AZCL-pullulan and protein content by SDS-PAGE. The fractions with highest activity and purity were pooled and concentrated using Amicon centrifugal filters with a cut off of 30 kDa.

Example 8

Temperature and pH Optimum and Temperature Stability of Pullulanases

Figure 4:
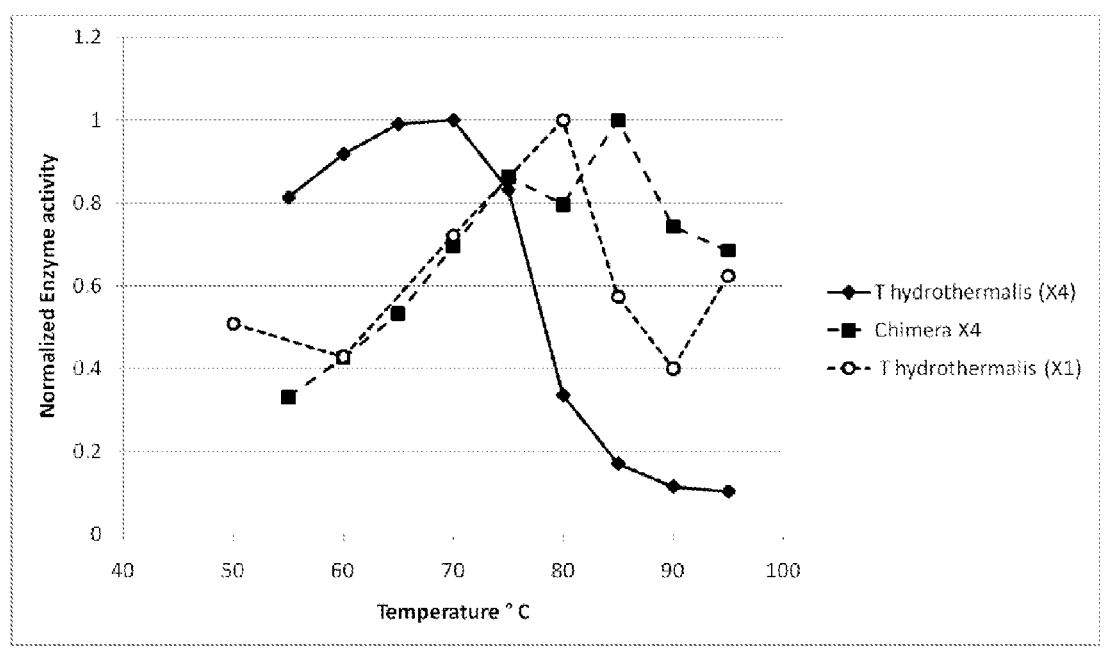
FIG. 4 shows the temperature profiles of the purified pullulanase *Thermococcus hydrothermalis* (X1 truncation, expressed in *Pichia pastoris*), the truncation X4 of *Thermococcus hydrothermalis* and the hybrid (chimer) of *Thermococcus hydrothermalis* and *Thermococcus litoralis* (truncation site X4).

The relative temperature optima of the purified pullulanases *Thermococcus hydrothermalis* (X1 truncation, expressed in *Pichia pastoris*), the truncation X4 of *Thermococcus hydrothermalis* and the hybrid (chimer) of *Thermococcus hydrothermalis* and *Thermococcus litoralis* (truncation site X4) were determined as described in the method section. FIG. 4 shows the relative activity profiles. The X4 hybrid had the highest temperature optimum of all three pullulanases with 85° C. at pH 4.5.

The temperature stability was measured by DSC determined as described in the Method section. The denaturation temperature for the X4 chimer was 98.5° C. and 86° C. for X4 *Thermococcus hydrothermalis*.

Figure 5:
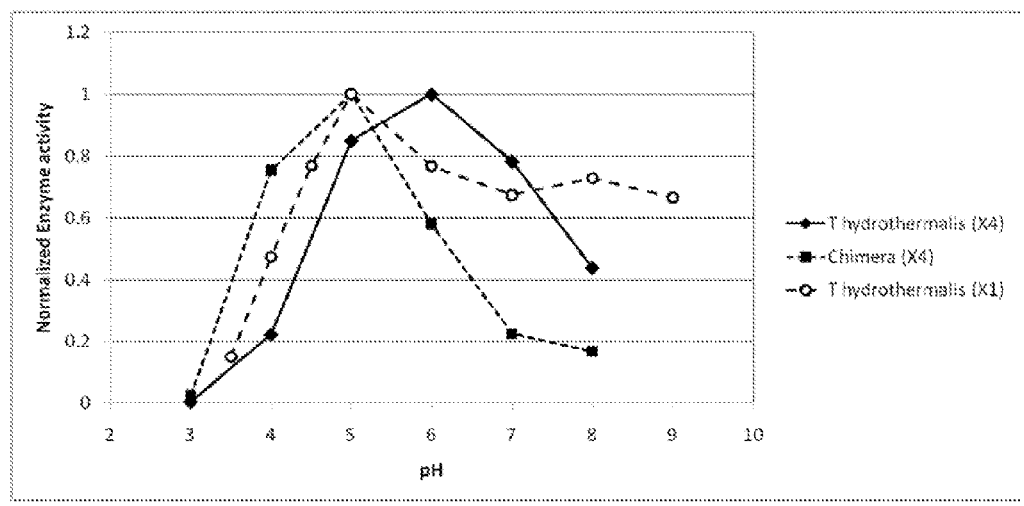
FIG. 5 shows the pH profiles of the purified pullulanases *Thermococcus hydrothermalis* (X1 truncation, expressed in *Pichia pastoris*), the truncation X4 of *Thermococcus hydrothermalis* and the hybrid (chimer) of *Thermococcus hydrothermalis* and *Thermococcus litoralis* (truncation site X4).

The pH optimum was determined as described in the Method section. FIG. 5 shows the pH profile of the three pullulanases mentioned above in this example. Truncation X1 and the X4 chimer had the same pH optimum at around pH 5, whereas the truncation X4 of *Thermococcus hydrothermalis* had a pH optimum that shifted one pH unit higher (pH 6).

Example 9

Liquefaction and Fermentation of Starch-Containing Material

The pullulanase isolated from *Thermococcus hydrothermalis* and expressed in *Pichia pastoris* was first application tested in corn slurry liquefaction using a Rapid Visco-Analyzer (RVA). The slurry was made using Corn LP ground corn, backset and tap water. The slurry was made at 32% dry solids (DS), mixed well and then pH adjusted to 5.4 using 50% (w/v) NaOH. The pullulanase was added to the slurry at doses of 1, 5 and 50 micrograms enzyme protein (EP)/g DS from a diluted stock solution made with de-ionized water. Pullulanase was not added to the control mash. Alpha-Amylase SC was used at 0.02% w/w ground corn. The RVA temperature profile was as follows: 5 minute ramp from 65 to 85° C., held at 85° C. for 90 minutes, 10 minute ramp to 32° C. There was continuous mixing at 210 RPM for the entire liquefaction. After liquefaction, the mash weights were adjusted back to the initial weight with tap water to ensure the % dry solids remained approximately the same. The pH of the mashes was adjusted to 5.0 with 40% w/v $H_2SO_4$. Urea and penicillin were added to the mashes at 700 and 3 ppm, respectively. Small scale (4-5 grams mash per fermentation tube) simultaneous saccharification and fermentations (SSF) were run with 5 replicates per mash using Fermentis RedStar® yeast (100 μL inoculum for each replicate; 2.75 g yeast rehydrated in 50 mL tap water for 30 minutes at 32° C.). The Glucoamylase SF dosage (0.5 AGU/g DS) was calculated using the following equation:

$$Enz. \text{ dose (ml)} = \frac{\text{Final } enz. \text{ dose } (AGU/g\ DS) \times \text{Mash weight (g)} \times \text{Solid content } (\%\ DS/100)}{(Conc. \text{ enzyme } AGU/\text{ml})}$$

Fermentation progress was measured using $CO_2$ weight loss over time. The amount of ethanol was calculated using the following equation:

$$g\ \text{ethanol}/g\ DS = \frac{g\ CO_2\ \text{weight loss} \times \frac{1\ \text{mol } CO_2}{44.0098\ g\ CO_2} \times \frac{1\ \text{mol ethanol}}{1\ \text{mol } CO_2} \times \frac{46.094\ g\ \text{ethanol}}{1\ \text{mol ethanol}}}{(g\ \text{mash in tube} \times \%\ DS\ \text{of mash})}$$

After 24 hours, one of the replicate tubes for each treatment was sacrificed for HPLC analysis by the addition of 10 microliters/g mash of 40% $H_2SO_4$, clarified by centrifugation (Beckman Allegra 6R centrifuge with a GH3.8 rotor at 3000 RPM for 10 minutes) and the supernatants filtered through Whatman 0.45 μm syringe filters. The 24 hours samples were diluted 1:5 (v/v) with 5 mM $H_2SO_4$ buffer prior to HPLC analysis. After 54 hours of fermentation, the remaining 4 tubes for each treatment were stopped as just described. HPLC analysis of ethanol, dextrins and organic acids was on an Agilent 1100/1200 series running a BioRad ion exclusion column with 5 mM $H_2SO_4$ as the mobile phase and the analytes were detected by a refractive index detector. Analytes were quantified using commercially available standards.

Example 10

Liquefaction and Fermentation of Starch Material using a Pullulanase

Figure 6:
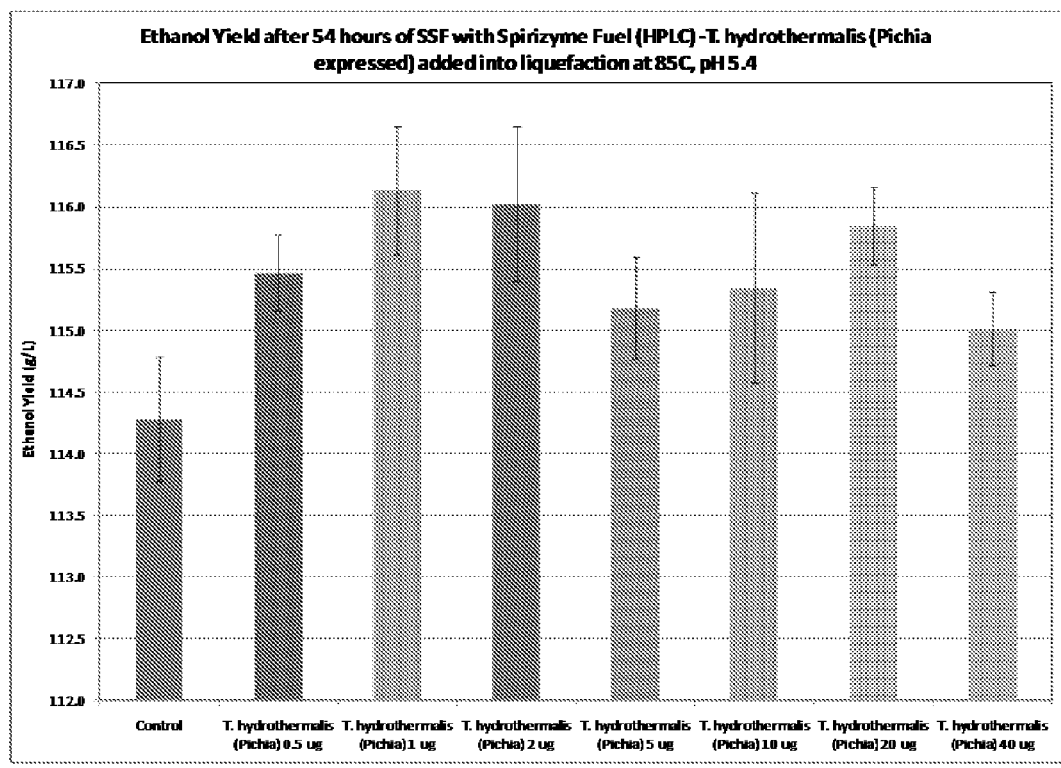
FIG. 6 shows HPLC quantification of ethanol titer (g/L) after 54 hours of SSF of mashes treated with increasing doses of *Thermococcus hydrothermalis* pullulanase at pH 5.4. The control did not have any pullulanase added during liquefaction. The columns represent the average of 5 replicate tubes while the error bars are the standard deviations of each treatment. The scale was 120 grams of total mash.

The pullulanase from *Thermococcus hydrothermalis* truncation X2 was added to starch liquefaction at different concentrations as described in Example 9. The 0.5, 1, 2 and 20 micro g EP/g DS doses produced statistically significantly more ethanol than the control (see FIG. 6) using the Student's t-test at the p<0.01 confidence interval. The 5, 10 and 40 micro g EP/g DS doses produced statistically more ethanol that the control at the p<0.05 confidence interval.

Example 11

Identifying X47 Domains using Hidden Markov Model (HMM)

The HMM model was made as described in the "Materials & Method"-section with 11 known family GH57 pullulanase sequences (see point 2) having X47 domains corresponding to positions 580-768 in SEQ ID NO: 2 (pullulanase from *Thermococcus hydrothermalis*). The program 'hmmsearch' was used with the derived HMM model to search the Uniprot database. The individual scores of the pullulanases having X47 domains are shown here:

| Organism | Accession number | HMMscore |
| --- | --- | --- |
| *Thermococcus hydrothermalis* | SWISSPROT: Q9Y8I8 | 427.4 |
| *Thermococcus* sp. HJ21. | SWISSPROT: B6SED6 | 439.3 |
| *Thermococcus kodakaraensis* | SWISSPROT: Q5JJ55 | 416.9 |
| *Thermococcus* sp. AM4. | SWISSPROT: B7QZQ4 | 418.1 |
| *Pyrococcus furiosus*. | SWISSPROT: Q8TZQ1 | 422.2 |
| *Pyrococcus furiosus* DSM 3638. | SWISSPROT: Q3HUR3 | 422.2 |
| *Pyrococcus furiosus*. | SWISSPROT: O30772 | 421.7 |
| *Thermococcus gammatolerans* DSM 15229 | SWISSPROT: C5A4E3 | 416.2 |
| *Thermococcus barophilus* MP. | SWISSPROT: B5IRL5 | 410.5 |
| *Thermococcus litoralis*. | SWISSPROT: Q8NKS8 | 414.2 |
| *Pyrococcus abyssi*. | SWISSPROT: Q9V294 | 394.7 |

Example 12

Cloning and Expression of Isolated X47 Domain from Amylpullulanase of *Thermococcus hydrothermalis* DSM 14834

| Oligo name | Oligo seq |
| --- | --- |
| C1QBX46-F (SEQ ID NO: 35) | AGGGGTATCTCTCGAGAAAAGACCATCCTACTT GTTCGGAAAC |
| C1QBX46-R (SEQ ID NO: 36) | GGTGCTGATGGAATTCGATGTCGGCGATAACAAC ACC |

The synthetic gene shown in SEQ ID NO: 14 herein was used as template to amplify the isolated domain of the amylopullulanase from *T. hydrothermalis*. The X47 domain was amplified with Phusion polymerase using oligo pairs mentioned in above table and cloned in *Pichia pastoris* as described in Example 5.

The sequences of the resulting expression constructs (the coding region of the expressed X47 domain and alpha signal peptide is shown in SEQ ID NO: 37 (DNA) and SEQ ID NO: 38 (Peptide) were confirmed by Sanger sequencing and named pX47. The plasmids were transformed into *Pichia pastoris* using a standard electroporation protocol (as described in Example 5). The complete CDS of the X47 domain was expressed in *Pichia pastoris* using the same method as also described in Example 5."

Purification

The pH of the *P. pastoris* culture expressing the X47 domain was adjusted to 7.0 with NaOH then filtered through a 0.45 micro-m filter. The solution was applied to a 30 mL Ni-sepharose High Performance column (GE Healthcare) which was equilibrated with 20 mM Tris-HCl containing 0.3 M NaCl at pH 7.0. The protein was eluted with a linear imidazole gradient (0-500 mM). Fractions from the column were analyzed by SDS-PAGE.

Characterization of X47 Domain
Amylopullulanase and Isolated X47 Domain
Ratio Profile 10 micro g pullulanase from *Thermococcus hydrothermalis* (P6VK), different amount of X47, 100 microL 0.4% AZCL-HE-pullulan (Megazyme International Ireland Ltd.) and 150 microL buffer at pH 4.5, and different amount of milliQ water (to give the same final volume for different ratio) were mixed and incubated at corresponding temperature for 50 min with shaking at 900 rpm. The tubes were put on ice after reaction and 100 microL supernatant was transferred to a microtiter plate. OD595 was read as a measure of pullulanase. For each sample the reaction was performed triplicate.

Results for different ratio (the amount of amylopullulanase was kept at 10 micro g for each reaction). The activity of the 10 micro g amylopullulanase alone was set to 100%.

Ratio profile for 50° C.

| Sample ratio | X47 domain | 1 | 1 | 1 | 1 | 2 | 5 | 10 |
|---|---|---|---|---|---|---|---|---|
| | *Thermococcus hydrothermalis* amylopullulanase | 10 | 5 | 2 | 1 | 1 | 1 | 1 |
| Relative activity (%) | | 95 | 102 | 152 | 105 | 120 | 134 | 100 |

Ratio profile for 75° C.

| Sample ratio | X47 domain | 1 | 1 | 1 | 1 | 2 | 5 | 10 |
|---|---|---|---|---|---|---|---|---|
| | *Thermococcus hydrothermalis* amylopullulanase | 10 | 5 | 2 | 1 | 1 | 1 | 1 |
| Relative activity (%) | | 97 | 90 | 89 | 127 | 133 | 109 | 89 |

Temperature Profile 10 micro g pullulanase from *Thermococcus hydrothermalis* (P6VK), 20 micro g X47, 100 microL 0.4% AZCL-HE-pullulan and 150 microL buffer at pH 4.5 were mixed and incubated at corresponding temperature for 50 min with shaking at 900 rpm. The tubes were put on ice after reaction and 100 microL supernatant was transferred to a microtiter plate. OD595 was read as a measure of pullulanase. For each sample the reaction was performed triplicate.

| | Temperature | | | |
|---|---|---|---|---|
| | 50° C. | 60° C. | 70° C. | 80° C. |
| Relative activity (%) | 16 | 20 | 33 | 100 | pH Profile pH buffers: 100 mM Succinic acid, HEPES, CHES, CAPSO, 1 mM $CaCl_2$, 150 mM KCl, 0.01% Triton X-100, pH adjusted to 3.5, 4.0, 4.5, 5.0, 6.0 7.0, and 8.0 with HCl and NaOH.

10 micro g pullulanase from *Thermococcus hydrothermalis* (P6VK), 20 micro g X47, 100 microL 0.4% AZCL-HE-pullulan (in MilliQ) and 150 microL 50 mM pH buffer (3.5-8) were mixed and incubated at 50° C. for 30 min with shaking at 900 rpm. 100 microL supernatant was transferred to a new microtiter plate. OD595 was read as a measure of pullulanase activity. For each enzyme the reaction was performed triplicate.

| | pH | | | | | | |
|---|---|---|---|---|---|---|---|
| | 3.5 | 4 | 4.5 | 5 | 6 | 7 | 8 |
| Relative activity (%) | 13 | 36 | 100 | 66 | 55 | 57 | 57 |

Boosting Test with Alpha-Amylase 1 micro g of *Subulispora* alpha-amylase disclosed as SEQ ID NO: 2 in WO 2009/140504 (Novozymes); different amounts of X47, 100 microL 0.4% AZCL-HE-amylose (Megazyme International Ireland Ltd.) at pH 4.5, and different amount of milliQ water (to give the same final volume for different ratio) were mixed and incubated at 37° C. for 30 min with shaking at 900 rpm. The tubes were put on ice after reaction and 100 microL supernatant was transferred to a microtiter plate. OD595 was read as a measure of pullulanase. For each sample the reaction was performed triplicate.

Results for different ratio (the amount of alpha-amylase was kept at 1 micro g for each reaction).

The activity of the 1 micro g alpha-amylase alone was set to 100%.

| Sample ratio | X47 Domain | 1 | 1 | 1 | 1 | 2 | 5 | 10 |
|---|---|---|---|---|---|---|---|---|
| | Amylase | 10 | 5 | 2 | 1 | 1 | 1 | 1 |
| Relative activity (%) | | 99 | 98 | 95 | 125 | 89 | 83 | 127 |

Example 13

Ethanol Production During Pullulanase in Combination with Protease

The full length pullulanase from *Thermococcus hydrothermalis* (Pullulanase H expressed in *Pichia pastoris*) was added into the liquefaction of corn in combination with Protease A and the Alpha-Amylase SC. The liquefactions were done at either pH 5.4, 30-32% dry solids, 85° C. in a water bath for two hours. The enzyme doses were 1, 5 or 50 micro g enzyme protein/gram dry solids for the pullulanase, 50 micro g enzyme protein/gram dry solids for the protease and 0.02% w/w corn for the Alpha-Amylase SC. The liquefied mashes were fermented with Glucoamyalase SF at a dose of 0.5 AGU/gram dry solids for 54 hours at 32° C. Table 1 present the average ethanol yields (in grams per liter) and standard deviations as quantified by HPLC.

The dose of Protease A in all cases was 50 micro g EP/g DS. The Pullulanase H dose was 1, 5 and 50 micro g EP/g DS. The control is the Alpha-Amylase SC alone without further enzyme additions. The pH of this liquefaction was 5.4 for all samples.

TABLE 1

Average ethanol yields (grams/liter) with standard deviations.

| Treatment | Ethanol (Average ± standard deviation) Grams/Liter |
|---|---|
| pH 5.4 | |
| Alpha-Amylase SC (control) | 121.30 ± 0.22 |
| Pullulanase H (1 micro g EP/g DS) + Protease A (50 micro g EP/g DS) | 121.52 ± 0.02 |
| Pullulanase H (5 micro g EP/g DS) + Metalloprotease A (50 micro g EP/g DS) | 122.30 ± 0.25 |
| Pullulanase H (50 micro g EP/g DS) + Protease A (50 micro g EP/g DS) | 122.65 ± 0.60 |

The present invention is further described in the following numbered paragraphs:

[1] A pullulanase variant of a parent pullulanase belonging to family GH57 and comprising an X47 domain, wherein the pullulanase variant is truncated after the X47 domain.

[2] The pullulanase variant of paragraph 2, wherein the parent pullulanase is obtained from a strain from the genus *Thermococcus*, including *Thermococcus* sp. AM4, *Thermococcus* sp. HJ21, *Thermococcus barophilus; Thermococcus gammatolerans; Thermococcus kodakarensis; Thermococcus litoralis*, preferably the one shown in SEQ ID NO: 4; *Thermococcus hydrothermalis*, preferably the one shown in SEQ ID NO: 2; *Thermococcus onnurineus*; or is obtained from a strain of the genus *Pyrococcus*, such as *Pyrococcus abyssi* and *Pyrococcus furiosus*.

[3] The pullulanase variant of paragraph 1 or 2, wherein the parent pullulanase is one of the pullulanases shown in SEQ ID NO: 2 (*T. hydrothermalis*), SEQ ID NO: 4 (*T. litoralis*), or the hybrid shown in SEQ ID NO: 34, or a sequence having pullulanase activity being at least 60% identical to SEQ ID NOs: 2, 4, or 34.

[4] The pullulanase variant of any of paragraphs 1-3, wherein the parent pullulanase has one or more (several) amino acids substituted, deleted, and/or inserted compared to SEQ ID NOS: 2, 4 or 34, or in another parent pullulanase.

[5] The pullulanase variant of any of paragraphs 1-4, wherein the parent pullulanase has at least 70%, preferably at least 80% preferably at least 85%, preferably at least 90%, at least 95%, at least 96%, at least 97%, at least 98%, at least 99% identity to the mature parent pullulanase of SEQ ID NOS: 2, 4, or 34.

[6] The pullulanase variant of any of paragraphs 1-5, wherein the pullulanase variant is at least 70%, preferably at least 80%, preferably at least 85%, more preferably 90%, more preferably 95%, more preferably 97%, at least 98%, at least 99% identical to the mature parent pullulanase of SEQ ID NOS 2, 4, or 34.

[7] The pullulanase variant of any of paragraphs 1-6, wherein the pullulanase variant has pullulanase activity.

[8] The pullulanase variant of any of paragraphs 1-7, further wherein the total number of different amino acids in the parent pullulanase or the pullulanase variant is fifteen, more preferably fourteen, even more preferably thirteen, even more preferably twelve, even more preferably eleven, even more preferably ten, even more preferably nine, even more preferably eight, even more preferably seven, even more preferably six, even more preferably five, even more preferably four, even more preferably three, even more preferably two, and most preferably one.

[9] The pullulanase variant of any of paragraphs 1-8, wherein the truncation is in the DUF2223a domain or DUF2223b domain.

[10] The pullulanase variant of any of paragraphs 1-8, wherein the truncation is within 100 amino acids, preferably within 50 amino acids, preferably within 20 amino acids after the end of the X47 domain.

[11] The pullulanase variant of any of paragraphs 1-10, wherein the variant is prepared from a parent pullulanase belonging to family GH57 which comprises an X47 domain, wherein the parent pullulanase is one shown in SEQ ID NO: 2, 4 or 34, or another parent pullulanase having at least 60% identity to SEQ ID NO: 2, 4 or 34, wherein the pullulanase variant comprises or consists of:
  a) an amino acid sequence having pullulanase activity;
    i) having at least 60% identity to the sequence from amino acids 1-1009 of SEQ ID NO: 2, preferably to the sequence from amino acids 1-782 of SEQ ID NO: 2; or
    ii) having at least 60% identity to the sequence from amino acids 1-988 of SEQ ID NO: 4, preferably to the sequence from amino acids 1-781 of SEQ ID NO: 4;
    iii) having at least 60% identity to the sequence from amino acids 1-782 of SEQ ID NO: 34;
  b) the parent pullulanase of SEQ ID NOs: 2, 4 or 34 truncated at a position after the X47 domain;
  c) another parent pullulanase having at least 60% identity to SEQ ID NOs: 2 4, or 34 truncated in a position corresponding to the ones defined in a) or b);
  d) a pullulanase variant defined in a), b) or c) having one or more (several) amino acids substituted, deleted, and/or inserted.

[12] The pullulanase variant of paragraph 11, wherein the parent pullulanase is obtained from a strain from the genus *Thermococcus*, including *Thermococcus* sp. AM4, *Thermococcus* sp. HJ21, *Thermococcus barophilus, Thermococcus gammatolerans, Thermococcus kodakarensis, Thermococcus litoralis*, preferably the one shown in SEQ ID NO: 4; *Thermococcus hydrothermalis; Thermococcus onnurineus*; or obtained from a strain of the genus *Pyrococcus*, such as *Pyrococcus abyssi* and *Pyrococcus furiosus*.

[13] The pullulanase variant of paragraph 11 or 12, wherein the parent pullulanase has at least 70%, preferably at least 80%, preferably at least 85%, preferably at least 90%, at least 95%, at least 96%, at least 97%, at least 98%, at least 99% identity to the mature pullulanase of SEQ ID NOs: 2 4, or 34.

[14] The pullulanase variant of any of paragraphs 11-13, wherein the pullulanase variant has at least 70%, preferably at least 80%, preferably at least 85%, preferably at least 90%, at least 95%, at least 96%, at least 97%, at least 98%, at least 99% identity to the mature part of any of the pullulanases in SEQ ID NOs: 2, 4, or 34, preferably the sequence from amino acids 1-1009 of SEQ ID NO: 2 or from amino acids 1-988 in SEQ ID NO: 4 or the sequence from amino acids 1-782 of SEQ ID NO: 34, preferably to the sequence from amino acids 1-782 of SEQ ID NOS: 2 or from the sequence from amino acids 1-781 of SEQ ID NO: 4.

[15] The pullulanase variant of any of paragraphs 1-14, wherein the parent pullulanase is a wild-type pullulanase.

[16] The pullulanase variant of any of paragraphs 11-15, wherein the truncation is in the DUF2223a domain, such as the DUF2223a domain located from positions 769-1009 in SEQ ID NO: 2, or positions 768-988 in SEQ ID NO: 4, or 769-782 in SEQ ID NO: 34, or in a corresponding positions in another parent pullulanase.

[17] The pullulanase variant of any of paragraphs 11-16, wherein the truncation is between amino acids in positions 782-783 in SEQ ID NO: 2, which corresponds to positions between positions 781-782 in SEQ ID NO: 4, or in corresponding positions in another parent pullulanase.

[18] The pullulanase variant of any of paragraphs 11-17, wherein the truncation is within 100 amino acids, preferably 50 amino acids, preferably 20 amino acids of the end of the X47 domain which ends at position 768 in SEQ ID NO: 2, position 767 in SEQ ID NO: 4, and position 768 in SEQ ID NO: 34, or a corresponding position in another parent pullulanase.

[19] The pullulanase variant of any of paragraphs 11-18, further wherein the total number of different amino acids in the parent pullulanase or the pullulanase variant is fifteen, more preferably fourteen, even more preferably thirteen, even more preferably twelve, even more preferably eleven, even more preferably ten, even more preferably nine, even more preferably eight, even more preferably seven, even more preferably six, even more preferably five, even more preferably four, even more preferably three, even more preferably two, and most preferably one.

[20] The pullulanse variant of any of paragraphs 1-19, which pullulanase variant has higher activity compared to the parent pullulanase.

[21] The pullulanase variant of any of paragraphs 15-20, wherein the parent pullulanase is encoded by a nucleic acid sequence which hybridizes under medium, more preferably high stringency conditions, with the nucleic acid sequence of SEQ ID NOs: 1 or 3, or its complementary strand.

[22] An X47 domain.

[23] The X47 domain of paragraph 22, wherein the domain is obtainable from a strain of the genus *Thermococcus*, including *Thermococcus* sp. AM4, *Thermococcus* sp. HJ21, *Thermococcus barophilus, Thermococcus gammatolerans, Thermococcus kodakarensis, Thermococcus litoralis; Thermococcus hydrothermalis; Thermococcus onnurineus*; or obtained from a strain of the genus *Pyrococcus*, such as *Pyrococcus abyssi* and *Pyrococcus furiosus*.

[24] The X47 domain of paragraph 22 or 23 comprising or consisting of the amino acid sequence 580-768 in SEQ ID NO: 2, amino acid sequence 579-767 in SEQ ID NO: 4 or the amino acid sequence 580-768 in SEQ ID NO: 34, or the amino acid sequence 86-274 shown in SEQ ID NO: 38, or corresponding position in another parent pullulanases.

[25] The X47 domain of any of paragraphs 22-24 comprising or consisting of the amino acid sequence 580-768 in SEQ ID NO: 2 or amino acid sequence 579-767 in SEQ ID NO: 4 or the amino acid sequence 580-768 in SEQ ID NO: 34, or the amino acid sequence 86-274 shown in SEQ ID NO: 38, or a corresponding positions in another parent pullulanases determined by Hidden Markov Model (HMM) having a score of at least 300, preferably a score of at least 350, preferably a score of at least 400, preferably between 300-500, such as between 380-450.

[26] The X47 domain of any of paragraphs 22-25, having at least 60% identity to amino acid sequence 580-768 in SEQ ID NO: 2 or amino acid sequence 579-767 in SEQ ID NO: 4 or amino acid sequence 580-768 in SEQ ID NO: 34 or amino acid sequence 86-274 in SEQ ID NO: 38.

[27] The X47 domain of any of paragraphs 22-26, wherein the X47 has at least 70%, preferably at least 80%, preferably at least 85%, preferably at least 90%, at least 95%, at least 96%, at least 97%, at least 98%, at least 99% identity to amino acid sequence 580-768 in SEQ ID NO: 2 or to amino acid sequence 579-767 in SEQ ID NO: 4 or amino acid sequence 580-768 in SEQ ID NO: 34.

[28] An isolated polynucleotide comprising a nucleotide sequence which encodes the pullulanase variant of any of paragraphs 1-21 or X47 domain of paragraphs 22-27.

[29] An isolated polynucleotide encoding a pullulanase variant of any of paragraphs 1-21, or an X47 domain of paragraphs 22-27, selected from the group consisting of:
  i) a polynucleotide having at least 60%, preferably at least 70%, more preferably at least 80%, more preferably at least 90%, more preferably at least 95%, at least 96%, preferably at least 97%, preferably at least 98%, preferably at least 99% identity with the pullulanase variant coding part of SEQ ID NOS: 1 or 3, or a complementary strand thereof;
  ii) a polynucleotide having at least 60%, preferably at least 70%, more preferably at least 80%, more preferably at least 90%, more preferably at least 95%, at least 96%, preferably at least 97%, preferably at least 98%, preferably at least 99% identity with the X47 domain coding part of sequence SEQ ID NO: 1, 3, or 37, or a complementary strand thereof; and
  iii) a polynucleotide which hybridizes under medium stringency, preferably high stringency conditions with the pullulanase variant or X47 domain coding part of SEQ ID NO: 1, 3, or 37, or a complementary strand thereof.

[30] A nucleic acid construct comprising the polynucleotide of paragraphs 28 or 29 operably linked to one or more (several) control sequences which direct the production of the polypeptide in an expression host.

[31] A recombinant expression vector comprising the nucleic acid construct of paragraph 30.

[32] A recombinant host cell comprising the nucleic acid construct of paragraph 30 or the vector of paragraph 31.

[33] A method for producing the pullulanase variant of any of paragraphs 1-25 or an X47 domain of any of claims 7-10 comprising (a) cultivating the recombinant host cell of paragraph 32 under conditions conducive for production of the pullulanase variant or X47 domain; and (b) recovering the pullulanase variant and/or X47 domain.

[34] The method of paragraph 33, wherein the expression level of the variant is the same or higher compared to the corresponding parent pullulanase under the same conditions.

[35] A preparation comprising a pullulanase variant having:
  (a) a temperature optimum in the range between 65-100° C., preferably 70-90° C., especially 75-85° C.;
  (b) a pH optimum in the range between pH 4-6, preferably 4.5-5.5 with AZCL-pullulan as substrate.

[36] A process for producing a fermentation product from starch-containing material comprising the steps of:
  (a) liquefying starch-containing material in the presence of an alpha-amylase and a family GH57 pullulanase;
  (b) saccharifying the liquefied material obtained in step (a) using a carbohydrate-source generating enzyme;
  (c) fermenting using a fermenting organism.

[37] The process of paragraph 36, wherein the GH57 pullulanase is obtained from a strain from the genus *Thermococcus*, including *Thermococcus* sp. AM4, *Thermococcus* sp. HJ21, *Thermococcus barophilus, Thermococcus gammatolerans, Thermococcus kodakarensis, Thermococcus*

*litoralis*, preferably the one shown in SEQ ID NO: 4; *Thermococcus hydrothermalis; Thermococcus onnurineus*; or obtained from a strain of the genus *Pyrococcus*, such as *Pyrococcus abyssi* and *Pyrococcus furiosus* or the pullulanase in SEQ ID NO: 34.

[38] The process of paragraph 36 or 37, wherein the pullulanase has at least 70%, preferably at least 80%, preferably at least 85%, preferably at least 90%, at least 95%, at least 96%, at least 97%, at least 98%, at least 99% identity to the mature parent pullulanase, preferably the parent pullulanase shown in SEQ ID NOs: 2, 4 or 34.

[39] The process of paragraph 37, wherein the family GH57 pullulanase is a pullulanase variant of any of paragraphs 1-21

[40] The process of any of paragraphs 36-39, further wherein a protease, such as an acid fungal protease or a metalloprotease is added before, during and/or after liquefaction.

[41] The process of paragraph 40, wherein the metallo protease is derived from a strain of the genus *Thermoascus*, preferably a strain of *Thermoascus aurantiacus*, especially *Thermoascus aurantiacus* CGMCC No. 0670.

[42] The process of any of paragraphs 36-41, wherein the alpha-amylase is a fungal alpha-amylase, preferably an acid fungal alpha-amylase or a bacterial alpha-amylase.

[43] The process of any of paragraphs 36-42, wherein the alpha-amylase is a fungal alpha-amylase, preferably derived from the genus *Aspergillus*, especially a strain of *A. niger, A. oryzae, A. awamori*, or *Aspergillus kawachii*, or of the genus *Rhizomucor*, preferably a strain the *Rhizomucor pusillus*, or the genus *Meripilus*, preferably a strain of *Meripilus giganteus*.

[44] The process of any of paragraphs 36-43, wherein the alpha-amylase is one disclosed in Richardson et al., 2002, *The Journal of Biological Chemistry* 277(29): 267501-26507 (Issue 19 July), preferably the one referred to as "BD5088".

[45] The process of any of paragraphs 36-44, wherein the alpha-amylase is present in an amount of 0.001 to 10 AFAU/g DS, preferably 0.01 to 5 AFAU/g DS, especially 0.3 to 2 AFAU/g DS or 0.001 to 1 FAU-F/g DS, preferably 0.01 to 1 FAU-F/g DS.

[46] The process of any of paragraphs 36-45, wherein the alpha-amylase is a bacterial alpha-amylase derived from a strain of *Bacillus*, such as *Bacillus stearothermophilus*, in particular the *Bacillus stearothermophilus* as disclosed in WO99/019467 as SEQ ID No: 3 with the double deletion I181+G182 and substitution N193F and/or a hybrid alpha-amylase comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+A181T+N190F+I201F+A209V+Q264S (using the *Bacillus licheniformis* numbering in SEQ ID NO: 4 of WO 99/19467).

[47] The process of any of paragraphs 36-46, wherein the alpha-amylase is dosed in an amount of 0.0005-5 KNU per g DS, preferably 0.001-1 KNU per g DS, such as around 0.050 KNU per g DS.

[48] The process of any of paragraphs 36-47, wherein the carbohydrate-source generating enzyme is selected from the group consisting of glucoamylase, alpha-glucosidase, maltogenic amylase, and beta-amylase.

[49] The process of any of paragraphs 36-48, wherein the carbohydrase-source generating enzyme is glucoamylase and is present in an amount of 0.001 to 10 AGU/g DS, preferably from 0.01 to 5 AGU/g DS, especially 0.1 to 0.5 AGU/g DS.

[50] The process of any of paragraphs 36-49, wherein the glucoamylase is derived from a strain of *Aspergillus*, preferably *Aspergillus niger* or *Aspergillus awamori*, a strain of *Talaromyces*, especially *Talaromyces emersonii*; or a strain of *Athelia*, especially *Athelia rolfsii*; a strain of *Trametes*, preferably *Trametes cingulata*; a strain of the genus *Pachykytospora*, preferably a strain of *Pachykytospora papyracea*; or a strain of the genus *Leucopaxillus*, preferably *Leucopaxillus giganteus*; or a strain of the genus *Peniophora*, preferably a strain of the species *Peniophora rufomarginata*; or a mixture thereof.

[51] The process of any of paragraphs 36-50, wherein step (a) is carried out at pH 4.-6, preferably at a pH from 4.5 to 5.5.

[52] The process of any of paragraphs 36-51, wherein the fermentation product is recovered after fermentation, preferably by distillation.

[53] The process of any of paragraphs 36-52, wherein the step (b) and (c) are carried out sequentially or simultaneously (i.e., SSF process).

[54] The process of any of paragraphs 36-53, wherein the fermentation product is an alcohol, preferably ethanol, especially fuel ethanol, potable ethanol and/or industrial ethanol.

[55] The process of any of paragraphs 36-54, wherein the starch-containing starting material is whole grains.

[56] The process of any of paragraphs 36-55, wherein the starch-containing material is derived from corn, wheat, barley, rye, milo, sago, cassava, manioc, tapioca, sorghum, rice or potatoes.

[57] The process of any of paragraphs 36-56, wherein the fermenting organism is a strain of *Saccharomyces*, preferably a strain of *Saccharomyces cerevisae*.

[58] The process of any of paragraphs 36-57, further comprising, prior to the step (a), the steps of:

x) reducing the particle size of starch-containing material, preferably to a particle size to between 0.05 to 3.0 mm, preferably 0.1-0.5 mm, so at least 30%, preferably at least 50%, more preferably at least 70%, even more preferably at least 90% of the starch-containing material fit through a sieve with a 0.05 to 3.0 mm screen, preferably 0.1-0.5 mm screen;

y) forming a slurry comprising the starch-containing material and water.

[59] The process of paragraph 58, wherein the slurry is heated to above the gelatinization temperature.

[60] The process of paragraph 55 or 56, wherein the slurry is jet-cooked at a temperature between 95-140° C., preferably 105-125° C., for 1-15 minutes, preferably for 3-10 minutes, especially around 5 minutes.

[61] The use of a pullulanase variant or X47 domain of any one of paragraphs 1-27 or preparation of paragraph 35, in a process of producing sweeteners from starch. λ[62] The use of a pullulanase variant or X47 domain of any one of paragraphs 1-27 or preparation of paragraph 35, in a process of producing a fermentation product, such as ethanol, from gelatinized and/or un-gelatinized starch.

The invention claimed is:

1. A pullulanase variant of a parent pullulanase belonging to family GH57 and comprising an X47 domain, wherein the pullulanase variant is truncated after the X47 domain, wherein the truncation is within 20 amino acids after the end of the X47 domain, which ends at position 768 in SEQ ID NO: 34, and wherein the variant has 90% identity to the pullulanase shown in SEQ ID NO: 34.

2. The pullulanase variant of claim 1, wherein the parent pullulanase is a SEQ ID NO: 34.

3. The pullulanase variant of claim 1, wherein the parent pullulanase has at least 90% sequence identity to the mature parent pullulanase of SEQ ID NO: 34.

4. The pullulanase variant of claim 1, wherein the pullulanase variant has at least 90% sequence identity to the mature parent pullulanase of SEQ ID NO: 34.

5. An isolated pullulanase variant of a parent pullulanase belonging to family GH57 and comprising an X47 domain, wherein the pullulanase variant is truncated after the X47 domain, wherein the parent pullulanase has at least 95% sequence identity to SEQ ID NO: 34, and wherein the truncation is within 20 amino acids after the end of the X47 domain, which ends at position 768 in SEQ ID NO: 34, and wherein the variant has 95% identity to the pullulanase shown in SEQ ID NO: 34.

6. The isolated pullulanase of claim 5, wherein the X47 domain has at least 99% sequence identity to amino acid sequence 580-768 in SEQ ID NO: 34.

7. An isolated pullulanase variant of a parent pullulanase belonging to family GH57 and comprising an X47 domain, wherein the pullulanase variant is truncated after the X47 domain, wherein the truncation is within 20 amino acids after the end of the X47 domain, which ends at position 768 in SEQ ID NO: 34, and wherein the variant has 99% sequence identity to the pullulanase shown in SEQ ID NO: 34.

* * * * *